(12) United States Patent
Schroeder et al.

(10) Patent No.: US 9,512,457 B2
(45) Date of Patent: Dec. 6, 2016

(54) SERUM-FREE STABLE TRANSFECTION AND PRODUCTION OF RECOMBINANT HUMAN PROTEINS IN HUMAN CELL LINES

(71) Applicants: Carola Schroeder, Heidelberg (DE); Haiyan Ding, Munich (DE); Cathleen Wegmann, Munich (DE)

(72) Inventors: Carola Schroeder, Heidelberg (DE); Haiyan Ding, Munich (DE); Cathleen Wegmann, Munich (DE)

(73) Assignee: OCTAPHARMA AG, Lachen (CH)

( * ) Notice: Subject to any disclaimer, the term of this patent is extended or adjusted under 35 U.S.C. 154(b) by 0 days.

(21) Appl. No.: 15/011,760

(22) Filed: Feb. 1, 2016

(65) Prior Publication Data

US 2016/0177362 A1    Jun. 23, 2016

Related U.S. Application Data

(62) Division of application No. 14/506,107, filed on Oct. 3, 2014, now Pat. No. 9,273,325, which is a division of application No. 11/993,604, filed as application No. PCT/EP2006/063705 on Jun. 29, 2006, now Pat. No. 8,871,439.

(30) Foreign Application Priority Data

Jun. 30, 2005 (EP) .................... 05105965

(51) Int. Cl.
| | |
|---|---|
| C12P 21/02 | (2006.01) |
| C12P 21/00 | (2006.01) |
| C07K 14/535 | (2006.01) |
| C07K 14/755 | (2006.01) |
| C07K 14/81 | (2006.01) |
| C12N 9/64 | (2006.01) |
| C12N 15/85 | (2006.01) |
| C07K 14/505 | (2006.01) |
| C07K 14/54 | (2006.01) |

(52) U.S. Cl.
CPC .............. *C12P 21/00* (2013.01); *C07K 14/505* (2013.01); *C07K 14/535* (2013.01); *C07K 14/54* (2013.01); *C07K 14/755* (2013.01); *C07K 14/8125* (2013.01); *C12N 9/644* (2013.01); *C12N 15/85* (2013.01); *C12P 21/02* (2013.01); *C12Y 304/21022* (2013.01)

(58) Field of Classification Search
None
See application file for complete search history.

(56) References Cited

U.S. PATENT DOCUMENTS

| 5,112,950 A | 5/1992 | Meulien et al. |
| 5,712,119 A | 1/1998 | Oppermann et al. |
| 6,528,246 B2 | 3/2003 | Stadler et al. |
| 8,299,042 B2 | 10/2012 | Pachuk |
| 2005/0124067 A1 | 6/2005 | Cates et al. |

FOREIGN PATENT DOCUMENTS

| EP | 0103409 | 3/1984 |
| EP | 0131740 | 1/1985 |
| EP | 0150735 | 8/1985 |
| EP | 0160457 | 11/1985 |
| EP | 0195821 | 10/1986 |
| EP | 0232112 | 8/1987 |
| EP | 0251843 | 1/1988 |
| EP | 0253455 | 1/1988 |
| EP | 0254076 | 1/1988 |
| EP | 0265778 | 5/1988 |
| EP | 0294910 | 12/1988 |
| EP | 0303540 | 2/1989 |
| EP | 0500734 | 5/1991 |
| EP | 2252972 | 11/1998 |
| EP | 1010762 | 6/2000 |
| EP | 1 533 380 | 5/2005 |
| WO | 86/01961 | 3/1986 |
| WO | 86/06101 | 10/1986 |
| WO | 87/01132 | 2/1987 |
| WO | 87/04187 | 7/1987 |
| WO | 87/07144 | 12/1987 |
| WO | 88/00381 | 1/1988 |
| WO | 91/07490 | 5/1991 |
| WO | 91/09122 | 6/1991 |
| WO | 93/15105 | 8/1993 |
| WO | 94/17834 | 8/1994 |
| WO | 95/13300 | 5/1995 |
| WO | 96/36369 | 11/1996 |
| WO | 99/29848 | 6/1999 |
| WO | 00/63403 | 10/2000 |
| WO | 01/14529 | 3/2001 |
| WO | 01/70968 | 9/2001 |
| WO | 02/08221 | 1/2002 |
| WO | 2004/095027 | 11/2004 |

OTHER PUBLICATIONS

International Search Report for PCT/EP2006/063705. International Publication No. WO 2007/003582 A3. Published May 18, 2007.
Durocher Y et al: "High-level and high-throughput recombinant protein production by transient transfection of suspension-growing human 293-EBNA1 cells" Nucleic Acids Research, vol. 30, No. 2; Jan. 15, 2002 (Jan. 15, 2002); pp. E9-E1.
Zaworski P Et Al; "Serum-Free Transfection and Selection in Chinese Hamster Ovary (Cho) Cells" Biotechniques, Informa Life Sciences Publishing, Westborough, MA, US; vol. 15, No. 5, 1993, pp. 863-864, 866.
Goodwin E C Et Al: "The 3'-Flanking Sequence of the Bovine Growth Hormone Gene Contains Novel Elements Required for Efficient and Accurate Polyadenylation" Journal of Biological Chemistry, vol. 267, No. 23, 1992; pp. 16330-16334.

(Continued)

*Primary Examiner* — Jim Ketter
(74) *Attorney, Agent, or Firm* — Thompson Hine LLP

(57) ABSTRACT

The present invention relates to an improved method for the serum-free production of an immortalized human cell line stably transfected under serum-free conditions with a specific vector carrying the gene coding for the protein of interest. Furthermore the invention relates to a production cell line obtained by said method, a production method for said protein of interest utilizing said production cell line, and the specific vector carrying the gene of interest itself.

24 Claims, 14 Drawing Sheets

(56) References Cited

OTHER PUBLICATIONS

Berg D T Et Al: "High-Level Expression of Secreted Proteins From Cells Adapted to Serum-Free Suspension Culture" Biotechniques, Informa Life Sciences Publishing, Westborough, Ma, Us; vol. 14, No. 6; Jun. 1993; pp. 972-978.
Japanese Patent Office, Notice of Rejection for Application No. 2008-518853. Mailing date: Sep. 27, 2011.
Enjolras et al., Two novel mutations in EGF-like domains of human factor IX dramatically impair intracellular processing and secretion. J. Thromb. Haemost., vol. 2, pp. 1143-1154, 2004.
Ido et al., Molecular Dissection of the α-Dystroglycan- and Integrin binding Sites within the Globular Domain of Human Laminin-10. J. Biol. Chem., vol. 279, pp. 10946-10954, 2004.
Sidis et al., Heparin and Activin-Binding Determinants in Follistatin and FSTL3. Endocrinology, vol. 146, pp. 130-136, 2005.
PCT, International Preliminary Report on Patentability, PCT/EP2006/063705 (Jan. 17, 2008).
Chen, C.A. et al., "Calcium Phosphate-Mediated Gene Transfer: A Highly Efficient Transfection System for Stably Transforming Cells with Plasmid DNA," BioTechniques, vol. 6, No. 7, pp. 632-638 (1988).
Chen, J-Z. et al., "Over-expression of Bim α3, a novel isoform of human Bim, result in cell apoptosis," The International Journal of Biochemistry & Cell Biology, 36 (8), pp. 1554-1561 (2004).
Fu, Y-G et al., "Apoptosis-inducing effect of recombinant Caspase-3 expressed by constructed eukaryotic vector on gastric cancer cell line SGC7901," World J Gastroenterol, vol. 9, No. 9, pp. 1935-1939 (Sep. 2003).
Graham, F.L. et al., Characteristics of a Human Cell Line Transformed by DNA from Human Adenovirus Type 5, J. Gen. Virol., 36, pp. 59-72 (1977).
Gregori, L. et al., "Partitioning of TSE infectivity during ethanol fractionation of human plasma," Biologicals, 32, pp. 1-10 (2004).
Li, J. et al., "Expression and functional characterization of recombinant human HDAC1 and HDAC3," Life Sciences, 74, pp. 2693-2705 (2004).
Lin, L. et al., "The Calcium Sensor Protein Visinin-like Protein-1 Modulates the Surface Expression and Agonist Sensitivity of the α4β2 Nicotinic Acetylcholine Receptor," The Journal of Biological Chemistry, vol. 277, No. 44, pp. 41872-41878 (2002).
Ma, H. et al., "Influence of Specific Regions in Lp82 Calpain on Protein Stability, Activity, and Localization within Lens," IOVS, vol. 41, No. 13, pp. 4232-4239 (Dec. 2000).
McGarvey, T.W. et al., "Isolation and characterization of the TERE1 gene, a gene down-regulated in transitional cell carcinoma of the bladder," Onogene, 20, pp. 1042-1051 (2001).
Shinki, T. et al., "Cloning and expression of rat 25-hydroxyvitamin $D_3$-1α-hydroxylase cDNA," proc. Natl. Acad. Sci. USA, vol. 94, pp. 12920-12925 (Nov. 1997).
Witsch-Baumgartner, M. et al., Mutationa Spectrum in the Δ7-Stero Reductase Gene and Genotype-Phenotype Correation in 84 Patients with Smith-Lem i-Opitz Syndrome, Am. J. Hum. Genet., 66, pp. 402-412 (2000).
Zhang, J. et al., Thioredoxin overexpression prevents NO-induced reduction of NO synthase activity in lung endothelial cells, Am. J. Physiol., 275 (Lung Cell. Mol. Physiol., 19), pp. L288-L293 (1998).
Zhang, W-Y. et al., "Rapid Purification of a New Humanized Single-chain Fv Antibody/Human Interleukin-2 Fusion Protein Reactive against HER2 Receptor," Acta Biochimica et Biophysica Sinica, vol. 36, No. 10, pp. 707-712 (2004).
Japanese Patent Office, Examiner's Decision of Rejection for Application No. 2008-518853. Mailing date: Nov. 13, 2012.
(D9) Nakamura et al. Signaling and Phosphorylation-impaired Mutants of the Rat Follitropin Receptor Reveal an Activation- and Phosphorylation-independent but Arrestin-dependent Pathway for Internalization. J. Biological Chemistry, vol. 273, No. 38 (1998), pp. 24346-24354.
(D10) Wang et al. AlbuBNP, a Recombinant B-Type Natriuretic Peptide and Human Serum Albumin Fusion Hormone, as a Long-Term Therapy of Congestive Heart Failure. Pharmaceutical Research, vol. 21, No. 11 (2004), pp. 2105-2111.
IL Patent Application No. 187676, Office Action (translation) mailed Mar. 30, 2015.
Kondo et al. Establishment of a Human Cell Line Highly Expressing Endothelin in Serum-Free Medium. J. Cardiovascular Pharmacology, 17 (Suppl. 7):S52-54; 1991.

A

← AAT

B

← AAT

Ser. No. 14/506,107 filed Oct. 3, 2014, which is a
SERUM-FREE STABLE TRANSFECTION AND PRODUCTION OF RECOMBINANT HUMAN PROTEINS IN HUMAN CELL LINES

RELATED APPLICATIONS

This application is a division of co-pending U.S. application Ser. No. 14/506,107 filed Oct. 3, 2014, which is a division of U.S. application Ser. No. 11/993,604 filed Mar. 26, 2010, now U.S. Pat. No. 8,871,439, which is the national stage entry of PCT/EP2006/063705 filed Jun. 29, 2006, which claims priority to European application Serial No. 05105965.7 filed Jun. 30, 2005, each of which is expressly incorporated by reference herein in its entirety.

The present invention relates to an improved method for the serum-free production of an immortalized human cell line stably transfected under serum-free conditions with a specific vector carrying the gene coding for the protein of interest. Furthermore the invention relates to a production cell line obtained by said method, a production method for said protein of interest utilizing said production cell line, and the specific vector carrying the gene of interest itself.

BACKGROUND

The recombinant production of human proteins is generally performed by cultivation of stably transfected eukaryotic and preferably mammalian cell lines and isolation of the protein from the culture broth. In case the recombinant proteins are intended for pharmaceutical applications, it was for a long time general practice to employ non-human cell lines in order to exclude the risk of copurifying infectious agents which may be harbored and expressed by human cells.

In the production of some human proteins, such as human blood clotting factor VIII, the use of non-human cell lines were found to entail certain disadvantages, e.g. unsatisfactory secretion levels of the expressed protein into the medium. It is believed that this may be due to slight differences within different types of mammalian cells concerning intracellular pathways for protein translation and modification, which also might have an effect on the biological activity of the expressed polypeptide. Apart from this, there were concerns that therapeutic proteins purified from non-human expression systems are contaminated with cellular components which can give rise to antigenic reactions in the patients. Also a concern was the non-human glycosylation pattern found on human proteins recombinantly produced in non-human expression systems. It is thought that this increases the likelihood of antigenic reactions in the patient. Furthermore, biological stability and efficacy of blood proteins such as clotting factors is substantially influenced by their N-glycosylation pattern. Especially peripheral and terminal monosaccharides are important, because they are detected by specific receptors from cells which are responsible for their degradation. Clotting factors, for example, carry sialic acid residues as terminal monosaccharides.

Modification on the composition of sialic acids in the antennae of glycoproteins can result in heterogenous glycosylation patterns. Thus, biological stability and efficacy is crucially involved when modification occurs. Hence, it is an important consideration in the production of recombinant clotting factors to evaluate the influence of glycosylation from non-human production cell lines versus human cell lines.

On the other hand, general methods for high level protein expression of a desired gene comprising immortalized, stably transfected mammalian cell lines expressing viral transcription activator proteins were made available (e.g. U.S. Pat. No. 5,712,119). These cell lines can be transformed with a vector construct where a suitable viral transcription promoter is operatively associated with a DNA sequence defining a gene of interest, the transcription activator proteins provided by the cell lines activate the viral transcription promoter and hence initiate the expression of the gene of interest.

As important as the cell line is the vector used for the introduction of the recombinant gene into an immobilized production cell line. A wide variety of vectors were utilized for translation of mammalian proteins, (for example, Witsch-Baumgartner, M et al. Am. J. Genet (2000). 66, 402-412 cloned DHCR7 cDNA into pCI-neo mammalian expression vector and expressed in the HEK 293 cells; McGarvey, T. W. et. al. Oncogene (2001) 20, 1041-1051 cloned TERE1 gene into the pTARGET mammalian expression vector and expressed in the human bladder transitional cell carcinomas; and Lin Lin et. al. J Biol Chem (2002) 277 (44) 41872-8 cloned the AchR gene into mammalian cell expression vector pEF6/myc-His vector and expressed it in 293 cells). A recently developed very potent vector which has proven to be capable of overexpression of recombinant proteins is the so-called pcDNA™ 3.1 vector of Invitrogen. Li J. et al., Life Sci. 2004 Apr. 16; 74(22):2693-705 have successfully over-expressed histone deacetylases using pcDNA 3.1 in HEK 293 cells. The cells were stably transfected and cultured in the presence of serum. Yuan-Gen Fu. et al., World J Gastroenterol 2003 have produced recombinant Caspase-3 using a pcDNA 3.1(+) based eukaryotic vector on gastric cancer cell line SGC7901 transiently transfected with said vector and cultured in the presence of serum. Ma H. et al., Invest Ophthalmol Vis Sci. 2000 December; 41(13):4232-9 examined the lack of stable protein and loss of enzymatic activity expressing Lp82 and Lp82-related proteins subcloned into pcDNA3.1 vector using COS-7 as cell line. The cells were transiently transfected and cultured in the presence of serum in the medium. Thioredoxin overexpression prevents NO-induced reduction of NO synthase activity in lung endothelial cells. Zhang J. et al., Am J Physiol. 1998 August; 275(2 Pt 1): L288-93 disclose the overexpression of thioredoxin gene in cultured porcine pulmonary artery endothelial cells by transient transfection of these cells with pcDNA 3.1 vector. The transfected cells were cultured in medium supplemented with serum. Shinki T. et al., Proc Natl. Acad. Sci. USA 1997 Nov. 25; 94(24):12920-5 compared a full length cDNA for the rat kidney mitochondrial cytochrome P450 mixed function oxidase, 25-hydroxyvitamin D3-1alpha-hydroxylase with vitamin D-deficient rat kidney cDNA and subcloned it into mammalian expression vector pcDNA 3.1 (+) and transiently transfected the vector into COS-7 transformed monkey kidney cells. The transfected cells were cultured in medium supplemented with serum. Zhang et al., Acta Biochimica et Biophysica Sinica 2004, 36(10): 707-712 disclose the transfection of human embryonic kidney 293 cells with pcDNA containing a gene coding for the humanized 520C9 single chain Fv antibody/human interleukin-2 fusion protein. Supernatant was taken after having cultured the cells for three days in serum-free SFM II media. The resultant fusion protein possessed binding specificity against p185 (promising target for antibody therapy in breast cancer) and retained the important immuno-stimulatory activities of IL-2. Chen, J. Z. et al., Int J Biochem Cell Biol. 2004

August; 36(8):1554-61 over-expressed Bim proteins, which are essential factors for apoptosis, using HEK 293 cells transfected with pcDNA-Bim alpha3.

A further measure for increasing the safety of recombinant proteins for pharmaceutical applications is the use of serum-free medium in the culturing process, as the use of serum represents a safety hazard as well as a source of unwanted contaminations. Such serum-free cultivation has the drawback that the yields of the production process are generally significantly reduced. A further safety concern is the use of serum when transfecting the host cells as a regular way in the practice, as the use of serum in the transfection procedure may cause unwanted biological material to be integrated into the cells which later on contaminated the product expressed by the cells in the production process. While some of the available methods for the production of recombinant proteins (including those mentioned above) do allow serum-free cultivation, serum-free stable transfection of human cells is not known. In the 19$^{th}$ ESACT Meeting, Harrogate, 5-8 Jun. 2005 the serum free transfection of CHO cells was suggested by Kuchenbecker et al.

Thus, it is desirable to develop an effective and safe method to produce human recombinant proteins.

SUMMARY OF THE INVENTION

Surprisingly, it was found that a non-contaminated human protein (i.e. a protein preparation free of unwanted protein by-products) can be obtained in good yield from immortalized human cell lines stably transfected, under serum-free conditions, with the gene encoding the protein of interest. In more detail, the present invention provides:

(1) a method for preparing an immortalized human cell line stably transfected with a nucleic acid sequence comprising a gene encoding a human target protein or a derivative or mutant thereof, a promoter and a bovine growth hormone polyadenylation (polyA) signal, said promoter and polyA signal being linked to the 5' and 3' end of the gene encoding said human target protein, respectively, which method comprises transfecting an immortalized human host cell line under serum-free conditions with a transfection vector comprising said nucleic acid sequence and an origin of replication;

(2) the method of (1) above wherein the transfection vector is derived from pcDNA 3.1 vector having the sequence of SEQ ID NO:4 or 5;

(3) the method of (1) or (2) above, wherein the human cell line is a human embryonic kidney cell selected from 293 cells (ATCC CRL-1573; DSM ACC 305), FreeStyle 293 cells (hereinafter "293F" cells; Invitrogen R79007), and 293T cells (ATCC CRL 11268; DSM ACC 2494);

(4) the method of (1) to (3) above, wherein the human protein is blood clotting factor IX, (e.g. as encoded by in bps 939 to 2324 of SEQ ID NO:1), alpha-1-antitrypsin (hereinafter "A1AT"; e.g. as encoded by bps 913 to 2259 of SEQ ID NO:2), blood clotting factor VIII (including wt factor VIII as shown in SEQ ID NO:8 or a B-domain deleted factor VIII mutant as encoded by bps 783 to 5162 of SEQ ID NO:3), factor VII/VIIa (including the a and b form thereof encoded by SEQ ID NOs:13 and 14), G-CSF (including the G-CSF a, b and c form shown in SEQ ID NOs:15, 16 and 17, respectively), or von Willebrand factor (vWF);

(5) a transfection vector comprising an origin of replication and a gene encoding a human protein as defined in (1) and (2) above, preferably said transfection vector being a pcDNA3.1 vector comprising the gene for a human protein as defined in (4) above;

(6) an immortalized human cell line obtainable by the method as defined in (1) to (5) above, preferably said human cell line being as defined in (3) or (4) above; and (7) a method for the recombinant production of a human target protein or a derivative or mutant thereof which comprises culturing an immortalized human cell line as defined in (6) above, preferably under serum-free conditions.

DETAILED DESCRIPTION OF INVENTION

Figure 1:
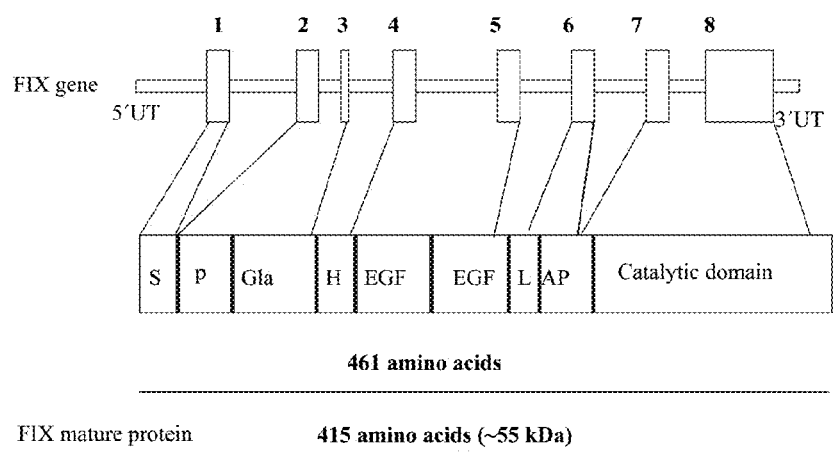
FIG. 1: The wild-type human clotting factor IX (FIX) protein. A schematic drawing of the FIX gene with its 5' untranslated (5' UTR) region and its 3' UTR region. The eight domains of the unprocessed 461 amino acid protein are indicated: S: signal peptide; P: propeptide; Gla domain: γ-carboxyglutamyl domain; H domain: hydrophobic sequence; EGF domain: epidermal growth factor-like domain; L: linking sequence; AP: activation peptide; Catalytic domain. The FIX mature protein has a length of 415 amino acids and an approximate molecular weight of 55 kDa.
Figure 2:
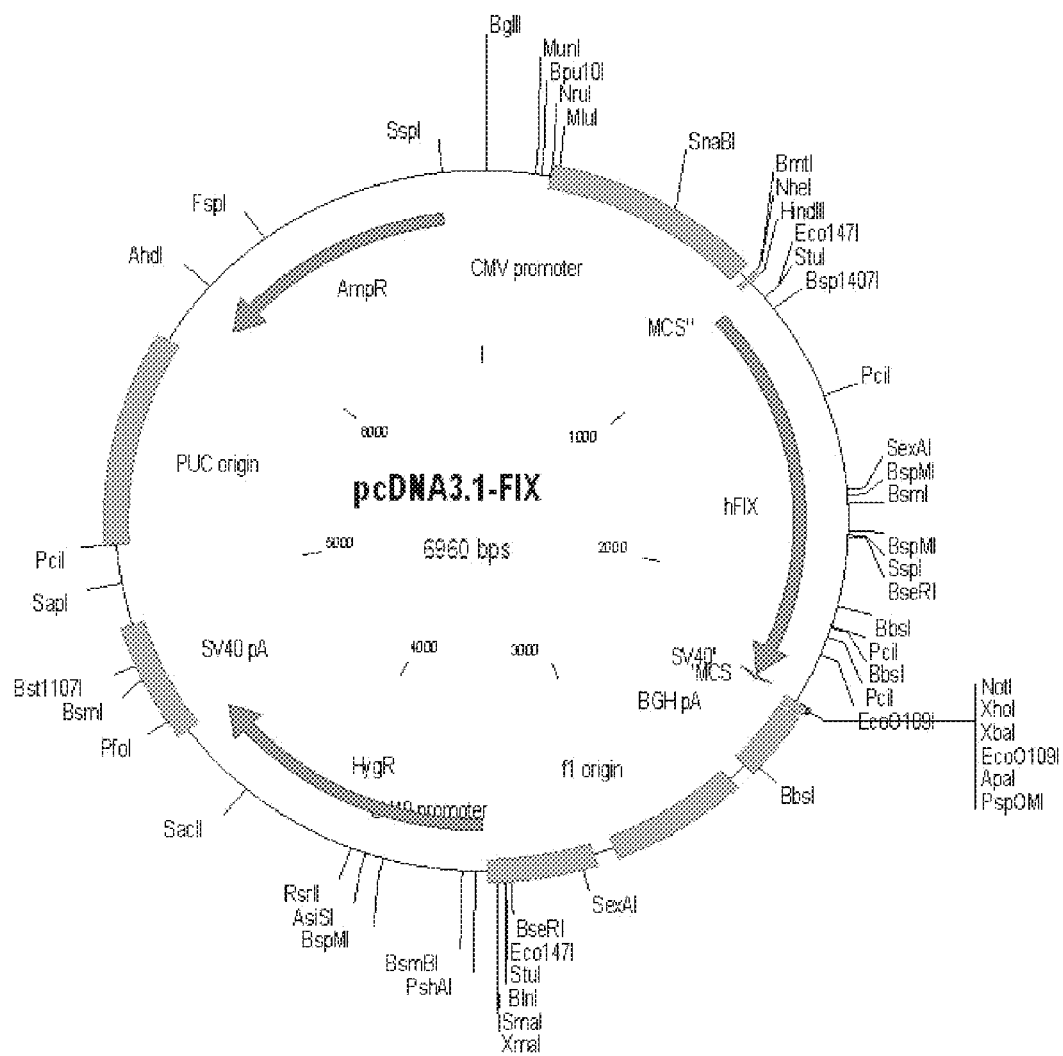
FIG. 2: The vector pcDNA3.1-FIX. The circular DNA vector comprises 6,960 base pairs, the exact sequence thereof being given in SEQ ID NO:1. In the schematic drawing the CMV promoter (CMV), the human FIX gene (hFIX), the f1 origin (f1), the hygromycin (Hyg) gene under control of the SV40 promoter (SV40), a poly A region (SV40 poly A), the pUC origin and the ampicillin (Amp) resistance gene are indicated, as well as numerous restriction sites. This vector is derived from the resequenced pcDNA 3.1 vector pcDNA3.1Hygro(+)-zz of SEQ ID NO:5.

The present invention provides an improved method for the transfection and production of human recombinant proteins in human immortalized cell lines completely under serum- and protein-free conditions. It allows the serum-free transfection and production of human proteins. The method may include one or more purification step(s) including viral inactivation procedures, which reduces the risk for contamination of the recombinant protein with human pathogens. Since human recombinant proteins produced in human cell lines carry a human glycosylation pattern, they are also less susceptible to degradation in comparison to human proteins lacking their natural glycosylation pattern. In summary the method of the invention offers various advantages over the prior art.

In particular, the method of embodiment (7) of the invention provides an effective system to produce safe and highly active human recombinant blood clotting factors, for example factors IX and FVIII for therapeutic application for Hemophilia B and A in humans. The method is suitable for expression of those wild-type proteins, but can also be used for mutants of those proteins, for example of factor VIII, which are exceptionally stable against proteolytic inactivation and thus allow to be subjected to vigorous virus inactivation protocols.

A preferred mode the method of embodiment (7) of the invention comprises serum-free culturing an immortalized cell line carrying a vector having a promoter linked to the 5' end of a DNA sequence encoding said human blood protein. The 3' end of the DNA sequence encoding said human blood protein is functionally linked to a bovine growth hormone polyA signal. According to the invention the immortalized human cell line is stably transfected with the vector. To detect stable transfection, the vector may further comprise, in addition to the gene for the human blood protein, at least one gene for a selection marker system which is functionally linked to a promoter.

Suitable promoters include viral promoters, housekeeping gene promoters, tissue specific promoters, etc. In case the promoter is a viral promoter, the cell line does not comprise the matching viral transcription activator protein for said promoter. However, the cell may comprise a viral transcription activator protein such as the T antigen which complements another viral promoter which is not functionally linked to the gene encoding the human blood protein. Preferably the promoter is a SV40 promoter, CMV promoter, EF-1alpha promoter, HSV TK promoter etc., most preferably the promoter is a CMV promoter, i.e. the constitutive, major intermediate early promoter of cytomegalovirus.

The expressions "transfection" or "transfected" refers to the introduction of a nucleic acid into a cell under conditions allowing expression of the protein. In general the nucleic acid is a DNA sequence, in particular a vector or a plasmid carrying a gene of interest under a suitable promoter, whose expression is controlled by said promoter. However, the term transfection also comprises RNA transfection. The skilled artisan is familiar with the various transfection methods such those using carrier molecules like cationic lipids such as DOTAP (Roche), DOSPER (Roche), Fugene (Roche), Transfectam® (Promega), TransFast™ (Promega) and Tfx™ (Promega), Lipofectamine (Invitrogene) and 293Fectin™ (Invitrogene), or calcium phosphate and DEAE dextran. He is also familiar with brute-force transfection techniques. These include electroporation, bombardment with nucleic-acid-coated carrier particles (gene gun), and microinjection. Finally the skilled artisan is also familiar with nucleic acid transfection using viral vectors.

"Transiently transfected" or "transient transfection" refer to the transient, i.e. non-permanent expression of the gene of interest due to the episomal nature of the introduced nucleic acid. By its very nature, RNA transfection or cytolytic viruses can only be used for transient expression. Episomal nucleic acids, including DNA (plasmids or vectors), is degraded by the cells after two to four days, and hence the expression of the gene of interest ceases then.

"Stably transfected" or "stable transfection" refers to the permanent expression of the gene of interest due to the integration of the transfected DNA into the genome of the cell. Most if not all cells have the potential to incorporate episomal DNA into their genome albeit at a very low rate. However, sophisticated selection strategies are employed to expand those cells that have integrated the transfected DNA. For that the vector must contain at least one gene for a selection marker such as e.g. hygromycin.

The term "stable transfection" or "stably transfected" is here also used to refer to cells carrying plasmids that can autonomously replicate and thus can be used for long-term expression of foreign genes. One particularly gene transfer system applicable for "stably transfecting" cells is based on recombinant retroviruses. Since integration of the proviral DNA is an obligatory step during the retroviral replication cycle, infection of cells with a recombinant retrovirus will give rise to a very high proportion of cells that have integrated the gene of interest and are thus stably transfected.

The term "culturing" refers to the maintaince of cells/cell lines in vitro in containers with medium supporting their proliferation and gene expression. Thus the culturing causes accumulation of the expressed secretable proteins in the culture medium. The medium normally contains supplements stabilizing the pH, as well as amino acids, lipids, trace elements, vitamins and other growth enhancing components.

The "serum-free", "serum-free transfection" or "serum-free cultivation" refers to the transfection and culturing of cells in medium containing suitable supplements except any kind of serum. Supplements are selected from amino acids, lipids, trace elements, vitamins and other growth enhancing components. Often the "serum-free" culture conditions are even more stringent and, if no exogenous protein is added, or already included in the medium, the medium is called "protein-free".

The term "immortalized human cell line" refers to human cells that are not primary cells taken directly from an organism. In particular it refers to permanently established cell culture that will proliferate indefinitely given appropriate fresh medium and space, and thus have escaped the Hayflick limit.

The term "concentration" refers to the concentration of the produced recombinant protein from the culture medium. Inherently it also results in a concentration of the protein. The person skilled in the art is familiar with concentration techniques such as filtration, including ultra filtration, centrifugation, precipitation, etc. The concentration does not necessarily result in a pure protein, and the isolated protein may still comprise non-protein and protein contaminants. Additional purification steps are often required.

The term "purification" refers to steps applied to the isolated protein is subjected to in order to obtain a substantially pure (at least 60% pure, preferably at least 75% pure, more preferably over 90% pure and most preferably over 99.9% pure) human recombinant protein. Purity can be measured by an appropriate method. The person skilled in the art is familiar with techniques employable for the purification of a recombinant protein such as immunoaffinity chromatography, affinity chromatography, protein precipitation, buffer exchanges, ionic exchange chromatography, hydrophobic interaction chromatography, size-exclusion chromatography, electrophoresis. In addition, the purification may comprise a virus inactivation step such as heat treatment and/or solvent detergent (SD)-treatment, at either dry or liquid state, in the presence or without chemical substances including protease inhibitors. Further, the purification may include one or more steps for prion removal, such as protein precipitation, filtration, chromatography steps, in particular affinity chromatography steps (see e.g. "Partitioning of TSE infectivity during ethanol fractionation of human plasma", Gregori, L. et al., Biologicals 32 1-10; 2 (2004); and "Removal of TSE agents from blood products", Foster, P. R., Vax Sanguinis 87 (Suppl. 2), S7-S10 (2004)). After virus inactivation a further purification step selected from anyone of the above listed ones may be necessary for removal of the chemical substances used for virus inactivation.

The term "vector" refers to any genetic construct, such as a plasmid, phage, cosmid, etc., which is capable of replication when associated with the proper control elements, into which fragments of DNA may be inserted or cloned. A vector comprises unique restriction sites and may be capable of autonomous replication in a host cell. The term includes cloning and expression vehicles. The "vector" may further carry one or more further regulatory elements, said regulatory elements preferably being selected from splice sites, recombination sites, polyA sites, enhancers, multicloning site and prokaryotic plasmid sequences.

The term "functionally linked" refers to the configuration of the vector where the promoter is located within the vector in such a manner that it can stimulate transcription of the DNA sequence coding for the protein of interest, in particular for the human blood protein.

The term "mature" refers to the molecular structure of a given protein of the processed protein, i.e. a protein which lacks the N-terminal export signal.

The term "promoter" refers to a region of a regulatory DNA sequence bound by RNA polymerase and transcription factors during the initiation of transcription.

The term "enhancer" refers to a cis-acting sequence that increases the utilization of an eukaryotic promoter, and can function in either orientation and in any location (upstream or downstream) relative to the promoter.

The term "polyadenylation (polyA) signal" refers to a specialized termination sequence. It signals the addition of a "tail" of adenines to the end of the mRNA that enables export of the mRNA to the cytoplasm. Upon reaching the cytoplasm, the polyA tail of the mRNA is maintained during protein translation and stabilizes the mRNA during protein expression.

The term "encodes" or "encoding" refers to a property of the nucleic acid sequence to be transcribed (in case of DNA) or translated (in case of mRNA) into a polypeptide (protein) in vitro or in vivo when placed under the control of an appropriate regulatory sequence.

For the purpose of the present application the term "express", "expressing" or "expression" refers to the transcription and translation of a gene encoding a protein.

The "human proteins" of the invention include, but are not limited to human proteins, polypeptides, mutations and modifications thereof. In particular the human proteins include recombinant plasma proteins, e.g. blood clotting factors (such as factor VIII, Factor VII/VIIa, Factor V, factor IX, Factor XI, von Willebrand factor, etc.), growth factors (such as erythropoietin, etc.), colony-stimulating factors (CSFs) (such as granulocyte stimulating factor (G-CSF), macrophage CSF (M-CSF), granulocyte-macrophage CSF (GM-CSF), cytokines (such as interleukins including interleukin 3, etc.), protease inhibitors (such as alpha-1-antitrypsin (A1AT), chymotrypsin, etc.), transport proteins (such as hormones, etc.), inhibitory or regulatory acting proteins, and the like. Furthermore mutations and modifications of these proteins or polypeptides are included, specifically mutations or modifications providing for a better stability of the recombinant protein, an elongated half-life, or a better recovery and include deletion, substitution or insertion mutants and chemical mutations of functional groups, respectively. Particularly preferred proteins which can be produced by the method of the invention of the application are human factor VIII (including B-domain deleted or wildtype), human factor IX, human G-CSF, human A1AT, human factor VII/VIIa and von Willebrand factor.

The recombinant production of the factor VIII and IX is known in the art (EP-A-160457; WO-A-86/01961, U.S. Pat. Nos. 4,770,999, 5,521,070 and 5,521,070).

In the case of factor VIII recombinant expression of subunits for the production of complexes showing coagulant activity is known in the art (e.g., from EP-A-150735, EP-A-232112, EP-A-0500734, WO-91/07490, WO-95/13300 U.S. Pat. Nos. 5,045,455 and 5,789,203). Moreover, the expression of truncated cDNA-versions partially or entirely lacking the sequence coding for the highly glycosylated B-domain have been described (e.g. in WO-86/06101, WO-87/04187, WO-87/07144, WO-88/00381, EP-A-251843, EP-A-253455, EP-A-254076, U.S. Pat. Nos. 4,868,112 and 4,980,456, EP-A-294910, EP-A-265778, EP-A-303540 and WO-91/09122). A particular factor VIII mutant in which the B-domain between positions Arg740 and Glu1649 has been replaced by an Arg-rich linker peptide having at least 3 Arg residues and comprising 10 to 25 amino acid residues (wherein said factor VIII numbering is relative to the mature wild-type factor VIII sequence shown in SEQ ID NO:9) is disclosed in WO 01/70968 which is herewith incorporated in its entirety. In particular, the Arg-rich linker peptide has 14 to 20 amino acid residues, while a linker comprising:

```
the amino acid sequence
                            (SEQ ID NO: 10)
SFSQNSRH,
and/or the amino acid sequence
                            (SEQ ID NO: 11)
QAYRYRRG,
and/or the amino acid sequence
                            (SEQ ID NO: 12)
SFSQNSRHQAYRYRRG
``` is particularly preferred. Such B-domain factor VIII mutein is encoded by nt 783 to 5162 of SEQ ID NO:3.

G-CSF is a lineage specific, small molecule in human blood that stimulates the production of a type of white blood cell from the bone marrow, known as neutrophils. Neutrophils play a cental role in the body's immune system and defend infections. G-CSF (particular cDNA sequences of the a, b and c form thereof being given in SEQ ID NOs:15, 16 and 17, respectively; the protein of the G-CSF b form (hereinafter "G-CSFb" protein) is shown in SEQ ID NO:27) is naturally produced by monocytes, fibroblasts, and endothelial cells. Normally the concentration in blood is about 40 μg/ml in healthy persons. In patient plasma, the level of G-CSF can drop more than ten-fold. G-CSF is also produced in cancer cell lines like 5637 cells which secrete about 70 ng/ml. For therapy, recombinant human G-CSF is produced in E. coli as a N-terminal methylated, non-glycosylated form by Amgen Inc. (Filgrastim/Neupogenn, which is also available as a PEGylated product (Pegfilgrastim/Neulasta®). Another drug is produced in CHO cells by Chugai Pharmaceuticals Co, which results in a glycosylated product (Lenograstim/Granocyte®). G-CSF is used as a drug to treat neutropenia either inherited or caused by chemotherapy (cancer), AIDS or bone marrow transplantation. For this, a typical dose is 5 μg/kg and day.

A particular A1AT cDNA sequence suitable with the invention of the present application is given in bps 973 to 2259 of SEQ ID NO:2. Particular factor VII/VIIa cDNA sequences are given in SEQ ID NOs:13 and 14 corresponding to the a and b form thereof. A particular vWF cDNA is given in SEQ ID NO:18.

The selection marker system includes hygromycin resistance, puromycin resistance, neomycin resistance, adenosine deaminase (ADA) resistance, aminoglycoside phosphotransferase (neo, G418, APH) resistance, bleomycin (phleo, bleo, zeocin) resistance, cytosine deaminase (CDA, CD) resistance, cytosine deaminase (CDA, CD) resistance, dihydrofolate reductase (DHFR) resistance, histidinol dehydrogenase (hisD) resistance, hygromycin-B-phosphotransferase (HPH) resistance, puromycin-N-acetyl transferase (PAC, puro) resistance, thymidine kinase (TK) resistance, and Xanthine-guanine phosphoribosyltransferase (XGPRT, gpt) resistance. Particularly preferred is the hygromycin resistance gene. Also the gene for the selection marker may be functionally linked with a polyA signal such as the one derived from the bovine growth hormone (BGH) or the SV40 polyadenylation signal.

The transfected cells are constantly exposed in their culture medium to the protein of the selection marker system, such as hygromycin during the selection phase, resulting in the survival of only those cells carrying the vector. A person skilled in the art is familiar with alternative selection markers suitable for the establishment of stably transfected cells, as well with the concentrations of the chosen selective agents which needs to be applied.

A particularly preferred vector of the invention carries a CMV promoter, a hygromycin gene, a polyA sequence and the gene of interest and preferably is the pcDNA3.1 vector of Invitrogen having the sequence of SEQ ID NO:4 wherein resequencing said vector it was found that it in fact has the sequence shown in SEQ ID NO:5.

The immortalized cell lines suitable for the method of the invention are selected from the group of kidney, bladder, liver, lung, cardiac muscle, smooth muscle, ovary or gastrointestinal cells. Those cells may carry in their genome adenoviral DNA sequences, in particular the first 4344 nucleotides of Ad5 sequences. Preferred are human foetal kidney cells (HEK) selected from the group consisting of 293 cells (ATCC CRL-1573; DSM ACC 305; ECACC ref.: 85120602), 293T cells (DSM ACC 2494; ECACC: tsa201, ref. 96121229), and FreeStyle 293 cells (293F cells; Invitrogen R79007). Most preferred are 293F cells. Those immortalized cell lines carrying said vector are cultured under conditions allowing expression of the recombinant gene. Essentially those are standard culturing conditions known to the person skilled in the art, however in case of cells carrying the gene for human factor IX, vitamin K should be included in the medium.

A particular embodiment of the present invention is the serum-free production of the recombinant protein in serum-free culture of the stably immortalized cells, which are also transfected under serum-free conditions. For that anyone of the above described immortalized human cell lines, preferably the 293F cell line is transfected and cultured under serum-free conditions. The cells are stably transfected in suspension culture in the absence of serum and then adapted to adherent cell growth for selection of single cell clones. Once individual clones are obtained, they are expanded adherently. After selection of best producing clones the cells are transferred to suspension culture. During the whole stable cell line procedure and in further up-scaling for production, cells are grown in serum-free medium and are never in touch with serum or human or animal proteins. The recombinant blood protein such as anyone of the blood clotting factors or a protease inhibitor such as A1AT or growth factors (such as G-CSF and GM-CSF) are isolated from the culture broth, and standard purification steps do follow. In more detail, the particular embodiment of serum-free production of the recombinant human blood protein, in particular human factor VIII or factor IX or A1AT or G-CSFb comprises the following steps:

(1) Transfection of human immortalized cells, preferably 293F cells in suspension culture without serum. Cells are cultured in disposable, sterile polycarbonate Erlenmeyer flasks. Cells are transfected with a density of e.g. $1\times10^6$ viable cells per ml with a transfection agent, preferably a cationic transfection agent, more preferred lipofectamine 2000 CD reagent (Invitrogen) or a reagent for the calcium phosphate transfection method); a vector is transfected encoding the human blood protein, preferably the vector is pcDNA3.1-FIX, pcDNA3.1-FVIII, pcDNA3.1-A1AT or pcDNA3.1-GCSFb;

(2) 24 to 120 h, preferably 36-96, more preferably 48 h post-transfection a suitable number of cells ($10^3$ to $10^{10}$; preferably $10^5$ to $10^8$, most preferably $10^6$ cells) are transferred into a flat culture dish for sedimentation to establish adherent growth. Preferably the culture dish is a 10 cm-dish and cells are cultured in serum- and protein-free media, preferably FreeStyle 293 Expression medium (12338-018, Invitrogen) or the serum-free in-house medium (Octapharma Stockholm).

(3) Selection pressure is started at 2 to 50 h, preferably 48 h post transfer into the flat culture dish. The medium is supplemented with a suitable selective agent selected from the group consisting of selection markers, e.g. hygromycin, neomycin, G418 and Zeocin. The preferred selective agent is hygromicin with a concentration of 10 to 300 µg/ml, preferably 50 to 200 µg/ml, most preferably 50 µg/ml. The pressure is maintained for at least 10 to 20 days, preferably for 14 days, whereby the hygromycin supplemented medium is exchanged every other day. Only stably transfected cells survive these selection conditions and form adherent cell clones which can be individually picked. Additionally an attachment factor can be used in order to stick cells on the dish and prevent cells floating from one clone to an other cell clone. This attachment factors could be f. e. poly-D-Lysine, synthetic medium supplements without human or animal proteins, or other substances. Alternatively, cloning rings could be used for picking of clones.

(4) Individual cell clones are picked and transferred into separate culture containers for serum-free expansion of cells (scaling up) while the selective pressure is omitted. Any culture container is suitably, but preferably the individual clones are first transferred into 96 well plates with a sufficient amount of medium, and then to 48-, to 24-, to 12- and to 6-well plates and then to spintubes. At the spintube stage, the cells are cultured in serum-free medium softly shaking in order to bring cells back into suspension growth. Once the cells have reached the 6-cell well plate or the spintube stage, it is optional to select the best cell clones according to some selection criteria, i.e. the growth rate of the cells, faster growing cells are preferred, and the amount of the recombinant protein they do produce. However, said selection can also be performed at any later stage.

(5) Cells obtained from the spintube culture were seeded into Erlenmeyer culture vessels with a sufficient amount of serum free medium. Additional selection criteria for up-scaled, in suspension growing serum- and protein-free cell clones are as follows: viability, cell morphology, no aggregation, robustness concerning centrifugation and no cell debris.

The method of the present invention works particularly well if the vector is pcDNA3.1-hygro(+)-zz. It is preferred that the gene encoding the human protein, in particular human FIX, FVIII, A1AT or G-CSFb is inserted in such a way that it is under the control of the CMV promoter as it is shown in FIGS. 2, 3, 7, and 11 respectively. Preferably the wild-type sequences of said genes are inserted, such that the recombinantly expressed protein is without any mutation and is structurally identical to the wild-type protein isolated from blood plasma. A schematic drawing of the wild-type human factor IX is shown in FIG. 1. SEQ ID NOs:1, 2, 3 and 22 provide the nucleic acid sequence for pcDNA3.1-FIX, pcDNA3.1-A1AT, pcDNA3.1-FVIII and pcDNA3.1-GCSFb, respectively. The respective proteins are encoded by nucleotides 939 to 2224, 913 to 2259, 679 to 5055 and 970 to 1584, respectively.

The present invention thus provides a method for the recombinant production of human factor IX, A1AT, factor VIII and G-CSFb cloned into pcDNA3.1™ giving rise to pcDNA3.1-FIX, pcDNA3.1-A1AT, pcDNA3.1-FVIII and pcDNA3.1-GCSFb, respectively, which are integrated into the genome of immortalized human cells, preferably human embryonic kidney cells such as 293 cells (ATCC CRL-1573; DSM ACC 305; ECACC ref.: 85120602), FreeStyle 293 cells (293F cells; Invitrogen R79007) or 293T cells (DSM ACC 2494; ECACC: tsa201, ref. 96121229).

Those cells carrying either pcDNA3.1-FIX or pcDNA3.1-A1AT or pcDNA 3.1-FVIII or pcDNA 3.1-GCSFb are cultured in medium under standard conditions enabling gene expression or alternatively they are cultured under serum-free conditions to minimize the risk of contamination with human pathogens. One or more prion removal steps may be included, such as protein precipitation, filtration, chromatography steps, in particular affinity chromatography steps. Alternatively/additionally a prion knock-out cell line can be used as expression cell. This can be obtained by complete genomic knock-out or antisense technology. In case of the production for human factor IX the cells are preferably cultured in the presence vitamin K. The human blood protein is isolated from the culture supernatant and subjected to subsequent purification steps known in the art to maximize the yield of a pure, stable and highly active product and are selected from immunoaffinity chromatography, anion exchange chromatography, size exclusion chromatography, etc., and combinations thereof. They can easily be adapted to the specific requirements needed to isolate recombinant factor IX, G-CSFb or A1AT. Quantity and activity of the purified protein during and after the purification procedure may be monitored by ELISA and/or one-stage coagulation time assays (aPTT).

To overcome the problems of possible infectious contaminations in the purified protein samples or in the product directly obtained from the cell culture supernatant containing the secreted recombinant protein of choice, the culture supernatant might be treated with procedures for virus inactivation including heat treatment and/or SD-treatment (dry or in liquid state, with or without the addition of chemical substances including protease inhibitors). A person skilled in the art is familiar with purification procedures. For example, the isolation and purification and recovery of high purity virus-inactivated factor VIII from blood plasma by anion exchange chromatography was described I (WO93/15105). In addition several processes for the production of high-purity, non-infectious coagulation factors from blood plasma or other biological sources have been reported. Lipid coated viruses are effectively inactivated by treating the potentially infectious material with a hydrophobic phase forming a two-phase system from which the water insoluble part is subsequently removed. A further advantage has been proven to complement the hydrophobic phase treatment simultaneously or sequentially with a treatment with a non-ionic biocompatible detergents and dialkyl or trialkyl phosphates (WO 96/36369, EP 0131740, U.S. Pat. No. 6,007,979). Non-lipid coated viruses require inactivation protocols consisting in treatment with non-ionic detergents followed by a heating step (60-65° C.) for several hours (WO 94/17834). After virus inactivation, a further purifying step for removing the chemical substances may be necessary. In summary, the present invention provides an effective protein production method based on a human cell line linked to approved methods of protein purification and for inactivation of potentially dangerous infectious agents. A safe and easy to use-system for production of recombinant proteins, for example the blood clotting factor IX or VIII, A1AT and G-CSFb has been established. The activity of the recombinantly produced proteins can be examined with standard tests. In case of the human factor IX for example with an activated partial thromboplastin time assay using Dapptin TC (Kaolin/Sulfatid-Phospholipid Cat. No. 5035090, Technoclone GmbH) activation with a manual coagulation instrument. Finally the thus obtained recombinant proteins, such as the blood protein described hereinbefore, in particular the human factor IX may be used in a pharmaceutical composition.

The invention is further described in the following examples. Said examples are however not to be construed as to limit the invention.

EXAMPLES

Materials and Methods
Human Cell Lines for Protein Expression:
Preferred cell lines are HEK293 (ECACC Ref. 85120602), FreeStyle 293 (293F; Invitrogen R79007) and 293T (tsA201, ECACC Ref. 96121229) which is a transformed embryonic human kidney cell line stably expressing an SV40 temperature-sensitive T antigen. These epithelial-like cell lines have been used in a variety of functional expression assays and been reported to produce high levels of recombinant proteins. The 293F cell line (Invitrogen), which is derived from the 293 cell line was preferably used in the Examples below. The parental cell line 293 is a permanent line established from primary embryonal human kidney transformed with sheared human adenovirus type 5 DNA (Graham et al., 1977; Harrison et al., 1977). The 293F cell line is a variant of the 293 cell line that has been adapted to suspension growth in FreeStyle™ 293 (293F) Expression Medium(12338-018, Invitrogen). The 293F cell line was obtained from Robert Horlick at Pharmacopeia. The 293F cell line was originally prepared from low passage Master Cell Bank cultures derived from the parental 293F cells that were re-cloned by limiting dilution. Cells have been constantly grown in the serum-free FreeStyle 293 Expression medium or a serum-free medium (Octapharma Stockholm) with good viability and good morphology for more than one year during the development of the present invention.

For efficient production of human factor IX, the medium can be modified by addition of vitamin K. These cell lines are capable of being cultivated in serum-free and/or protein-free medium containing suitable supplements.

Determination and Measurement of Target Proteins
Determination of Human Factor IX Concentration by ELISA:
Human recombinant factor IX levels in the supernatant were determined by ELISA using a goat anti-human FIX (GAFIX-AP, Affinity Biologicals) as capture antibody according to standard procedure. All incubations were performed in a humid chamber at RT. Both standards, Octanyne (plasma-derived FIX, Octapharma) and BeneFIX (recombinant FIX, Genetics Institute) were used. The detecting antibody was a peroxidase conjugated goat anti-human FIX (GAFIX-APHRP, Affinity Biologicals). ABTS (Cat. No. 1682008, Roche Diagnostics) was added to each well as substrate, colorimetric reaction was detected at 405 nm in 15 minutes. Results were calculated by linear regression of standard concentration versus standard absorbance.

Detection of Human Clotting Factor IX Activity:
The clotting activity of human recombinant factor IX in supernatants was determined as follows: The clotting activity was assayed based on an activated partial thromboplastin time assay using Dapptin TC (Kaolin/Sulfatid-Phospholipid, Cat. No. 5035090, Technoclone GmbH) activation with a manual coagulation instrument (Amelung KC 4A micro, Amelung GmbH). For the study, 50 µl supernatant from transfected cells, 50 µl FIX-deficient plasma (Progen) and 50 µl Dapptin TC were incubated for 2 minutes at 37° C. Coagulation was started by adding 50 µl $CaCl_2$ (Cat. No. 84687-22F, Instumentation Laboratory). Sample coagulation time was compared to both Octanyne or/and BeneFIX.

Determination of BDDrhFVIII with COAMATIC:FVIII Assay (Chromogenix):
The commercial chromogenic assay kit COAMATIC: FVIII (Chromogenix, cat. No. 82 25 85) contains FIX, FX and a chromogen which is turned into a yellow water soluble dye by FXa cleavage. FVIII containing samples complete this system: FVIII activates FIX by complexing, this complex activates FX by proteolytic cleavage to become FXa. FXa turns the chromogen into a dye which subsequently is determined photometrically at 405 nm. This test is designed for determination of FVIII from patient plasmas. The following procedure was set up in order to make this test applicable for the factor VIII measurement in diluted culture media. As control standards, full length recombinant human clotting factor VIII (NIBSC, order no. 57814F) and normal control plasma (Instrumentation Laboratory Company) was used.

Sample preparation: Samples were diluted with dilution buffer delivered with COAMATIC reagents to a prospective final FVIII activity between 2 and 20 mIU/ml and are compared to the WHO No. 6 standard curve.

Method: On a 96-well array placed on the thermobloc, both standards and samples are measured in triple.

| Operation scheme (per well): | | |
| --- | --- | --- |
| Reagent | Volume | Incubation (37° C.) |
| Diluted standards and samples | 50 µl | 4 min |
| Factor reagent (37° C.) | 50 µl | place into 96-well photometric device, incubate 2 min at 37° C. in incubator |
| S-2765 + I-2581 (37° C.) | 50 µl | place into 96-well photometric device, incubate 2 min at 37° C. in incubator |
| 20% acetic acid | 50 µl | place into 96-well photometric device, shake 15 s in 96-well photometer determine absorptions at 405 nm immediately |

Determination of A1AT Activity with Elastase Activity Test:
After transfection of A1AT cDNA, A1AT was expressed and secreted into cell culture medium. After removal of cells by centrifugation (5 minutes, 1000 rpm), A1AT activity was measured in culture supernatant. In this activity test, A1AT activity was determined by its inhibitory effect upon elastase. Elastase cleaves pNA from the substrate N-succinyl-$(Ala)_3$-pNA. pNA release is measured photometrically at 405 nm. By comparison with standard samples with defined A1AT activity, the activity of the respective samples is determined. As proven in other experiments, the test is valid in serum-free Freestyle medium. To confirm the fact that Freestyle medium has no influence on the test, two standard curves were prepared: standard human plasma was diluted in T+ buffer or in Freestyle medium.

Dilution of samples: All samples were tested undiluted, 1:10 and 1:50 diluted in Freestyle medium and are compared with standard dilutions of human plasma.

Method: 50 µl of each standard dilution and sample dilution, respectively was pipetted into a well of the 96-well micro titer plate. After adding 150 µl of Elastase working solution to each well, the 96-well plate was shaken for 1 minute on the ELISA reader and incubated for 30 minutes at 37° C. 100 µl of substrate working solution was added to each well with the multipette. Absorption at 405 nm was measured immediately after addition of substrate solution and after 7 minutes incubation at 37° C. in the dark. The first value represents the basis absorption without elastase-catalised reaction and is substacted from the second one which represents the absorption after elastase cleaved pNA from the substrate. Using the result after the substraction, the A1AT activities of the samples are calculated according to the standard curve.

Determination of G-CSF Activity by ELISA:

Human recombinant G-CSF levels in the cell culture supernatants were determined by ELISA using a mouse anti-human G-CSF antibody (MAB-214, R&D System) as capture antibody according to standard procedure. All incubations were performed in a humid chamber at room temperature. The G-CSF standard (recombinant hG-CSF, *E. coli*, 214-CS-025, R&D Systems) was used. The detection antibody was a biotinylated goat anti-human G-CSF (BAF-214, R&D Systems). Streptavidin was conjugated to horseradish-peroxidase (DY998, R&D Systems) linked to the detection antibody. The QuantaBlu™ Fluorogenic Peroxidase Substrate (15169, Pierce) was added to each well as substrate, fluorometic reaction was detected at extinction 320 nm/Emission 420 nm within 60 min. Results were calculated by linear regression of standard concentration versus standard relative fluorescence units (RFU).

Example 1

Cloning of Target Proteins

A. Cloning of Human Factor IX:

From the vector pTG36 as disclosed in WO01/70968, a 1.4 kb fragment containing the open reading frame of the human clotting factor IX was cut out by double-digestion with Hind III and NotI. This fragment was ligated to the 5.6 kb fragment of the HindIII and NotI double-digested vector pcDNA3.1Hygro(+)-zz (derived from V870-20, Invitrogen) resulting in the vector pcDNA3.1-FIX shown in FIG. 2. The DNA sequence of pcDNA3.1-FIX is shown in SEQ ID NO.1. Three additional nucleotide insertions in the vector backbone were found in the pcDNA3.1Hygro(+)-zz vector (see SEQ ID NO:5) compared to the sequence published by Invitrogen (as shown in SEQ ID NO:4). The vector pcDNA3.1-FIX contains a cassette hygromycin-resistance gene to enable a selection method for a stably transfected cell clone (see FIGS. 2, 3 and 7). The vector allows the establishment of stably expressing cell lines by calcium phosphate transfection or others, and subsequent selection for hygromycine resistants.

Figure 7:
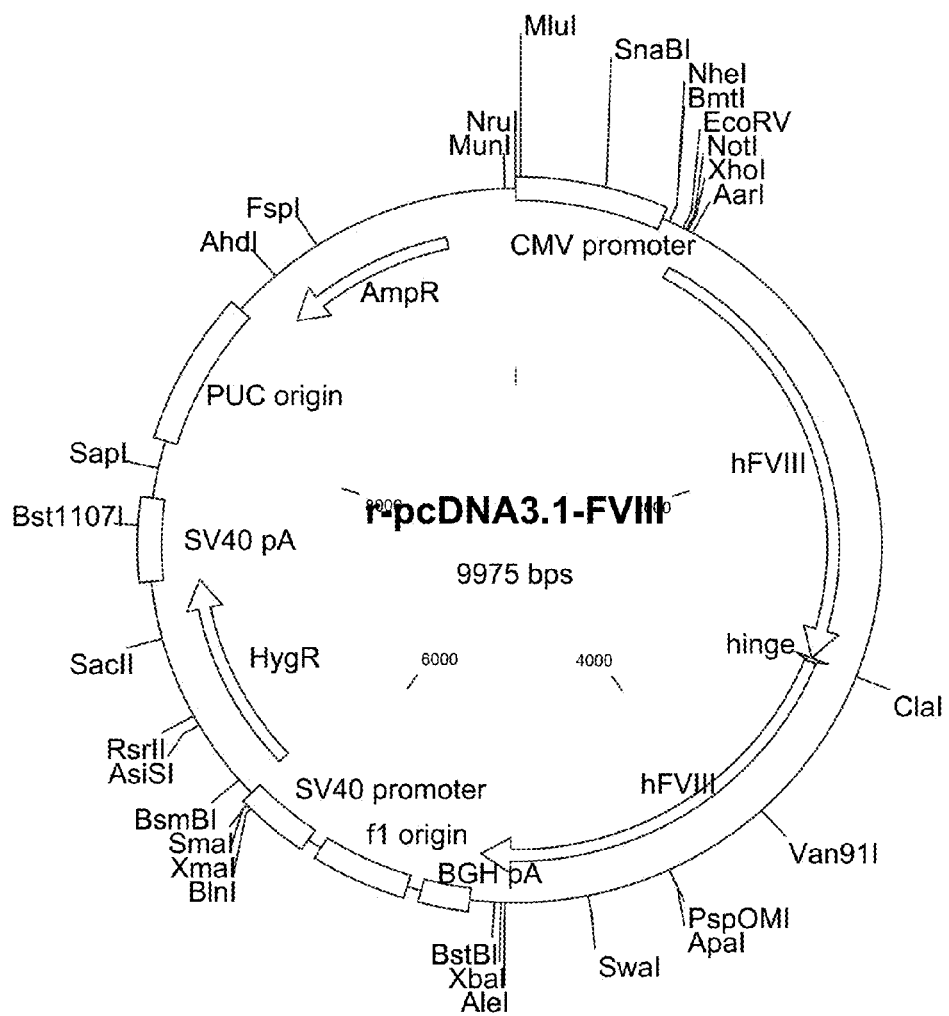
FIG. 7 shows the vector pcDNA 3.1-F.VIII. The vector comprises 9,975 bps, the exact sequence thereof being shown in SEQ ID NO:3. The factor VIII protein encoded by bps 783 to 5162 is a B-domain deleted factor VIII mutant as disclosed in WO 01/70968. Again this vector is derived from vector pcDNA 3.1 Hygro(+)-zz of SEQ ID NO:5.

B. Cloning of Human Factor VIII:

A 4380 bp FVIIIcDNA containing the open reading frame of a B-domain deleted human clotting factor VIII was isolated from the vector pTGF8-2hyg-s (SEQ ID NO:7; the production of which being disclosed in WO01/70968) with NotI+XhoI digestion and ligated with pcDNA3.1Hygro(+)-zz, which was linearized with XhoI+PspOMI resulting in the vector pcDNA3.1-FVIII shown in FIG. 7.

C. Cloning of Human A1AT:

A1AT mRNA was isolated directly from the HepG-2 cells (DSMZ# ACC 180) using mRNA Miniprep Kit (Sigma, Cat# MRN-10). In the following step mRNA was captured on oligo (dT) beads. Afterwards, mRNA will be transcribed into double-stranded cDNA with Avian Myeloblastosis Virus Reverse Transcriptase (AMV RT, Promega, Cat# M5101) following RT-PCR (reverse Transcription-Polymerase Chain Reaction). A1AT cDNA was amplified with PCR reaction. The PCR product was loaded on agarose gel. The appropriate DNA-band was isolated and afterwards purified with the Qiaquik Gel Extraction Kit (Qiagen, Cat#28704). Then A1AT fragment was subcloned into a commercial Vector (TOPO® Invitrogen, Cat# K4650-01). For cloning of pCMV-Script: PCR II TOPO-A1AT was digested with EcoRI, the A1AT 1370 bp fragment was ligated with pCMV-Script linearized with EcoRI.

For cloning of pCI-neo-A1AT PCR II TOPO-A1AT was digested with EcoRI, the A1AT 1370 bp fragment was ligated with pCI-neo linearized with EcoRI.

Figure 3:
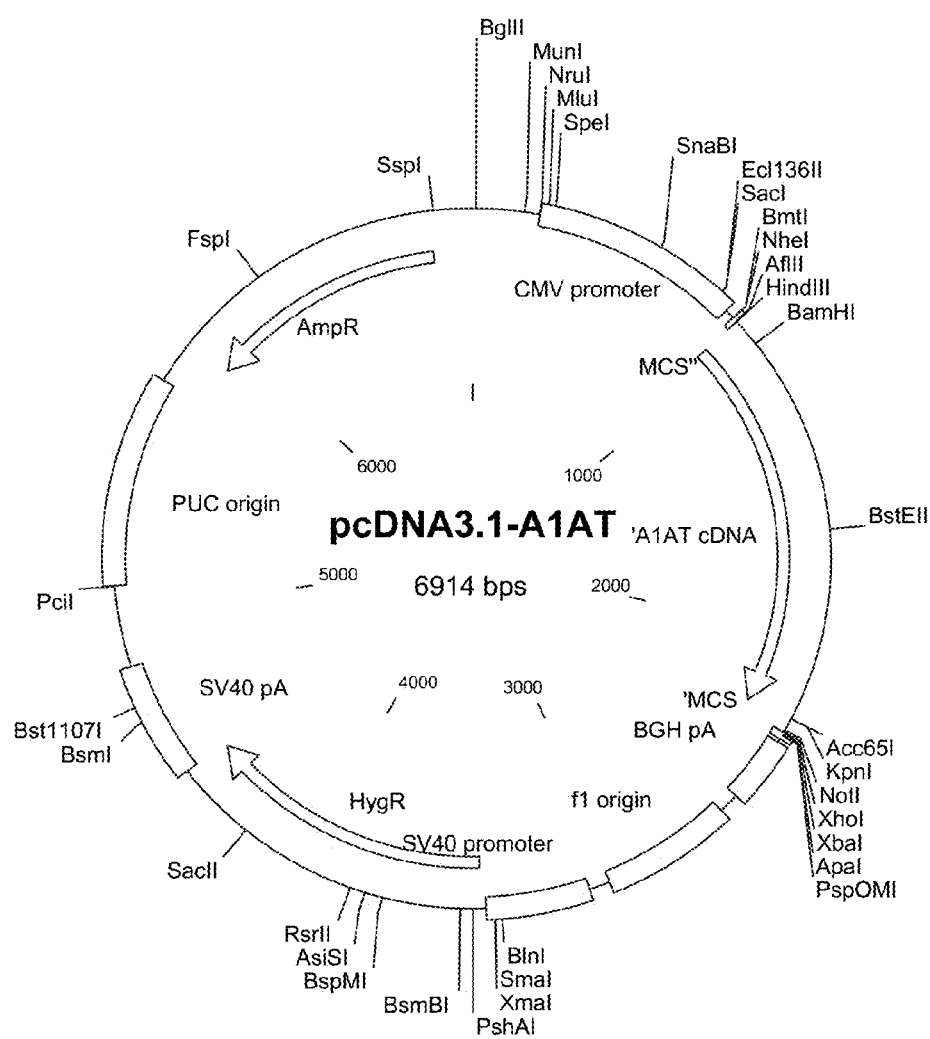
FIG. 3: The vector pcDNA3.1-A1AT. The circular DNA vector comprises 6,914 bps, the exact sequence thereof being given in SEQ ID NO:2. In the schematic drawing the CMV enhancer promoter, the A1AT cDNA, bovine growth hormone polyadenylation (polyA) signal including a transcription termination sequence for enhanced mRNA stability, the f1 origin (f1), the hygromycin (Hyg) gene under control of the SV40 promoter (SV40), the SV40 poly A region (SV40 poly A), the pUC origin and the ampicillin (Amp) resistance gene are indicated, as well as numerous restriction sites. This vector is derived from vector pcDNA3.1Hygro(+)-zz of SEQ ID NO:5.

For cloning of pcDNA3.1-FVIII 1370 bp A1AT was isolated with PCR II TOPO-A1AT digested with XhoI+HindIII and ligated with pcDNA3.1 linearized by XhoI+HindIII. The resulting vector is shown in FIG. 3.

Figure 9:
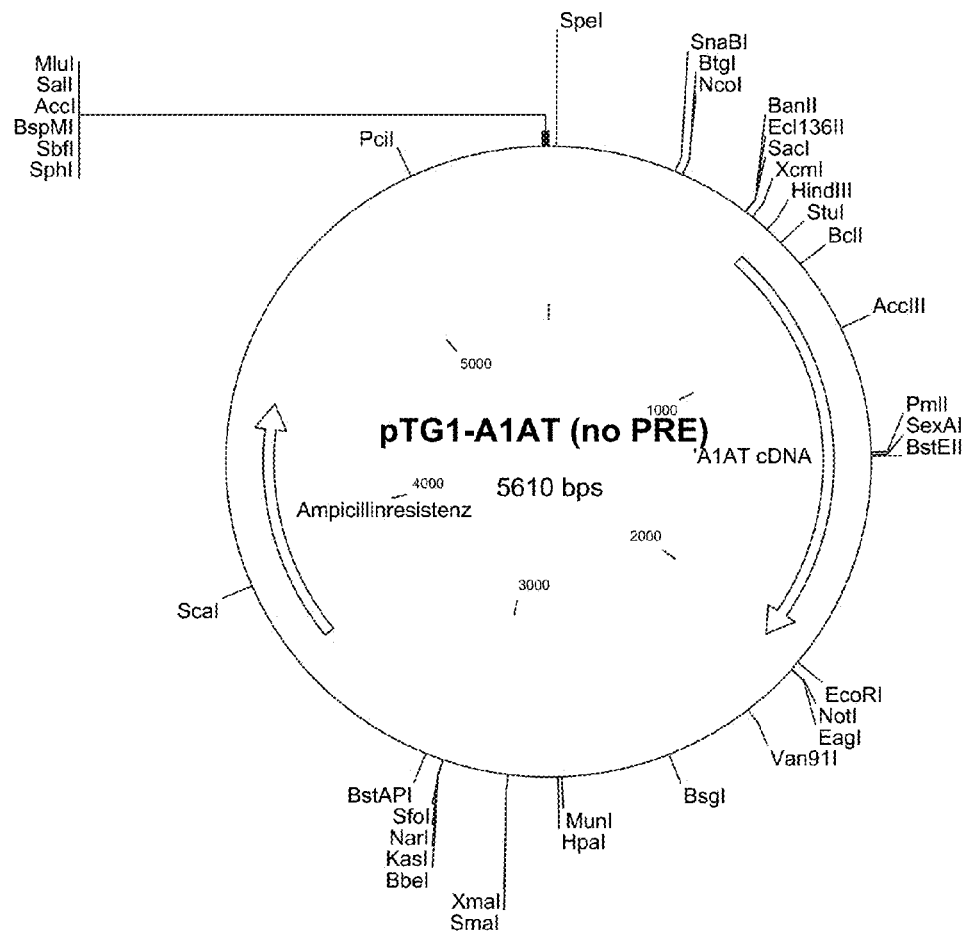
FIG. 9 shows the vector pTG1-A1AT. The vector comprises 5,610 bps, the exact sequence thereof being shown in SEQ ID NO:6.

For cloning of pTG1-A1AT PCR II TOPO-A1AT was digested with HindIII and NotI. The A1AT 1370 bp fragment was ligated with pTG1 (no PRE), linearized with HindIII and NotI. The resulting vector is shown in FIG. 9.

D. Cloning of Human G-CSF cDNA:

Total RNA was isolated directly from natural 5637 human urinary bladder carcinoma cells with RNeasy mini kit (QIAGEN, cat. No. 74104). Afterwards, the isolated total RNA was incubated with DNase I to digested possibly mixed genomic DNA of 5637 cells. To get DNase-free total RNA the reaction mixture was treated with RNeasy clean-up kit (QIAGEN, cat. No. 74204). RT-PCR with the total RNA as template was performed with oligo(dT)12-18 primer (Invitrogen, Cat. No. 18418-012) and Superscript™ II RNase H-Reverse Transcriptase (Invitrogen, Cat. No. 18064-022) in the presence of RNase inhibitor (Roche, Cat. No. 799-017) to synthesize ds cDNA pool from 5637 cells. G-CSF cDNA was amplified then with PCR reaction. G-CSF cDNA was isolated from agarose gel with QIA quick Gel Extraction kit (QIAGEN, Cat. No. 28704) and sequenced with both of the following G-CSF PCR primers:

```
G-CSF Forward:
                                   (SEQ ID NO: 19)
  5'-ATG GCT GGA CCT GCC ACC CAG AGC-3'

G-CSF Reverse:
                                   (SEQ ID NO: 20)
  5'-TCA GGG CTG GGC AAG GTG GCG TAG-3'
```

The sequence of the DNA synthesized from 5637 cells was confirmed by sequence analysis to be a GCSF-b form (having the sequence shown in SEQ ID NO:26).

The cDNA of GCSF-b form isolated as described above was then directly ligated into the commercial vector pCR2.1

Figure 10:
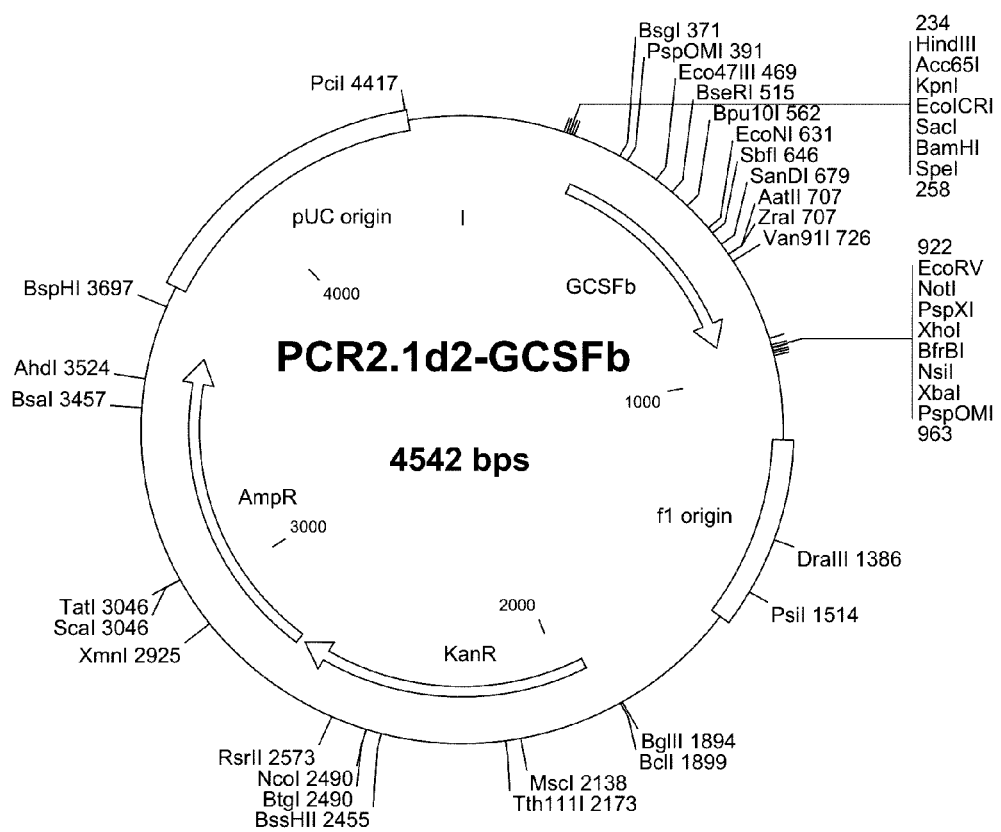
FIG. 10 shows the vector pCR2.1d2-GCSFb. The vector comprises 4,542 bps, the exact sequence thereof being shown in SEQ ID NO:21.

(Invitrogen). The resulting plasmid was designated pCR2.1d2-GCSFb and is shown in FIG. 10.

Figure 11:
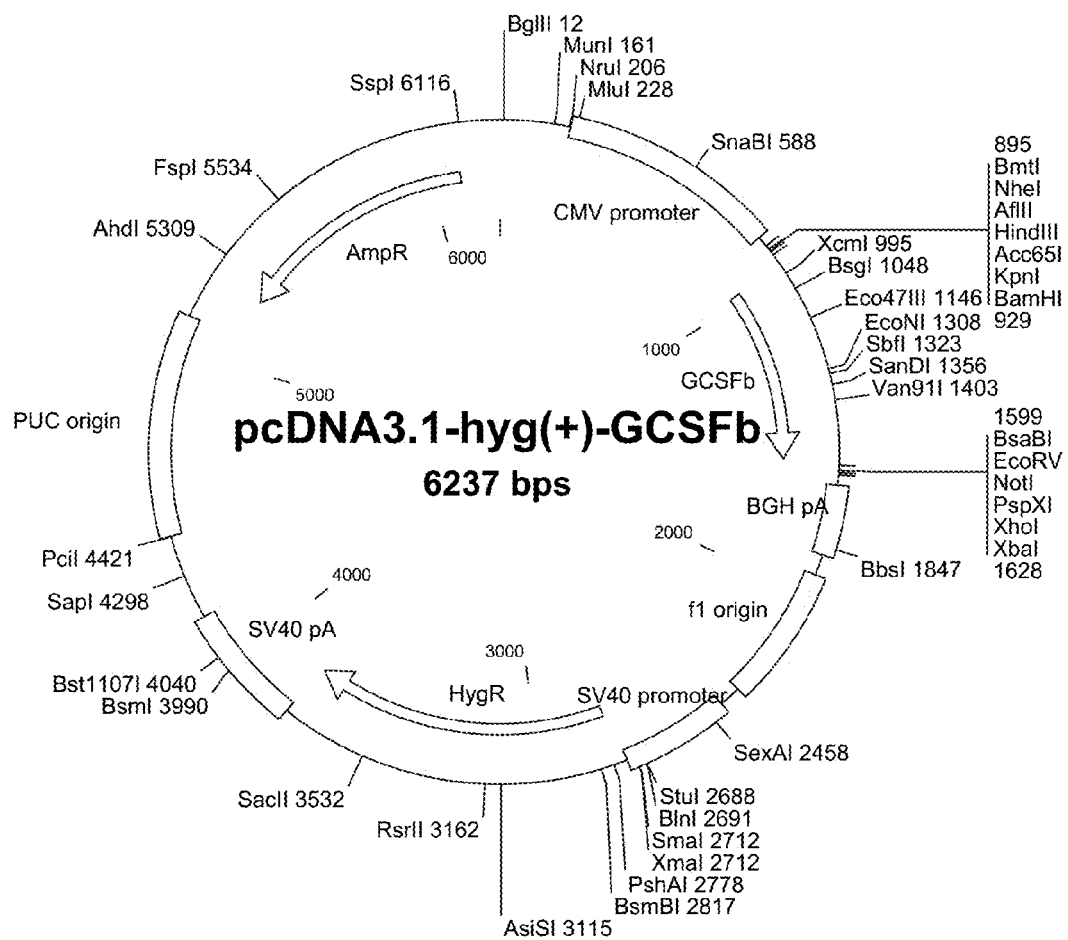
FIG. 11 shows the vector pDNA3.1-GCSFb. The vector comprises 6,237 bps, the exact sequence thereof being shown in SEQ ID NO:22.

PCR2.1d2-GCSFb was digested with HindIII and NotI, the 705 bp GCSFb cDNA fragment was isolated and ligated into the vector pcDNA3.1Hygro(+)-zz, which was linearized with HindIII and NotI. The resulting pDNA3.1-GCSFb vector is shown in FIG. 11.

Figure 12:
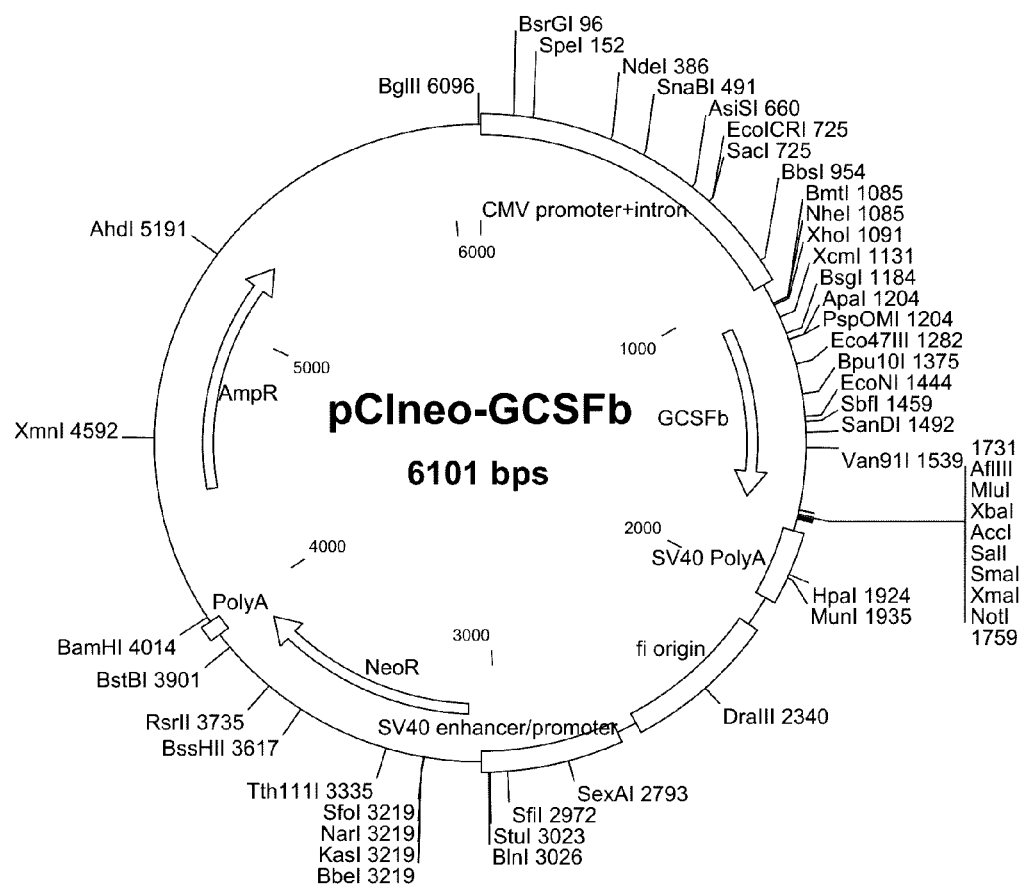
FIG. 12 shows the vector pCINeo-GCSFb. The vector comprises 6,101 bps, the exact sequence thereof being shown in SEQ ID NO:23.

PCR2.1d2-GCSFb was digested with EcoRI, the 629 bp GCSFb cDNA fragment was isolated and ligated into the pCINeo vector, which was linearized with EcoRI. The resulting pCINeo-GCSFb vector is shown in FIG. 12.

Figure 13:
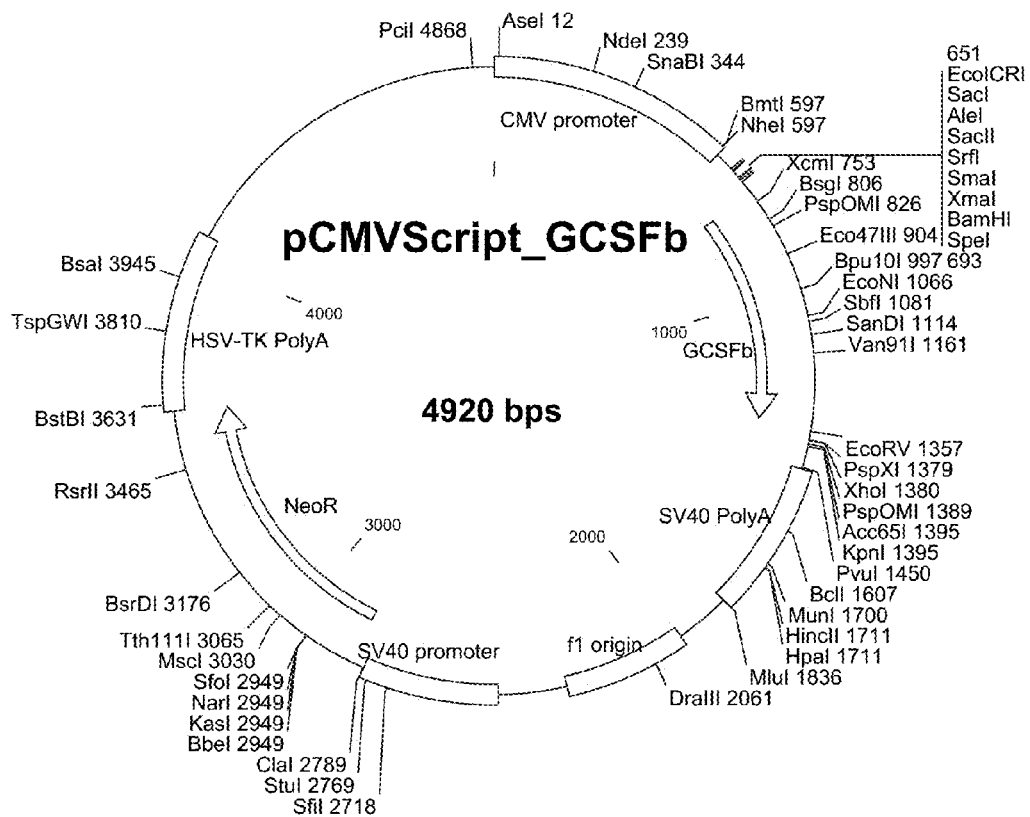
FIG. 13 shows the vector pCMVScript-GCSFb. The vector comprises 4,920 bps, the exact sequence thereof being shown in SEQ ID NO:24.

PCR2.1d2-GCSFb was digested with BamHI and XhoI, the 693 bp GCSFb cDNA fragment was isolated and ligated into the pCMVScript vector, which was linearized with BamHI and XhoI. The resulting pCMVScript-GCSFb vector is shown in FIG. 13.

Figure 14:
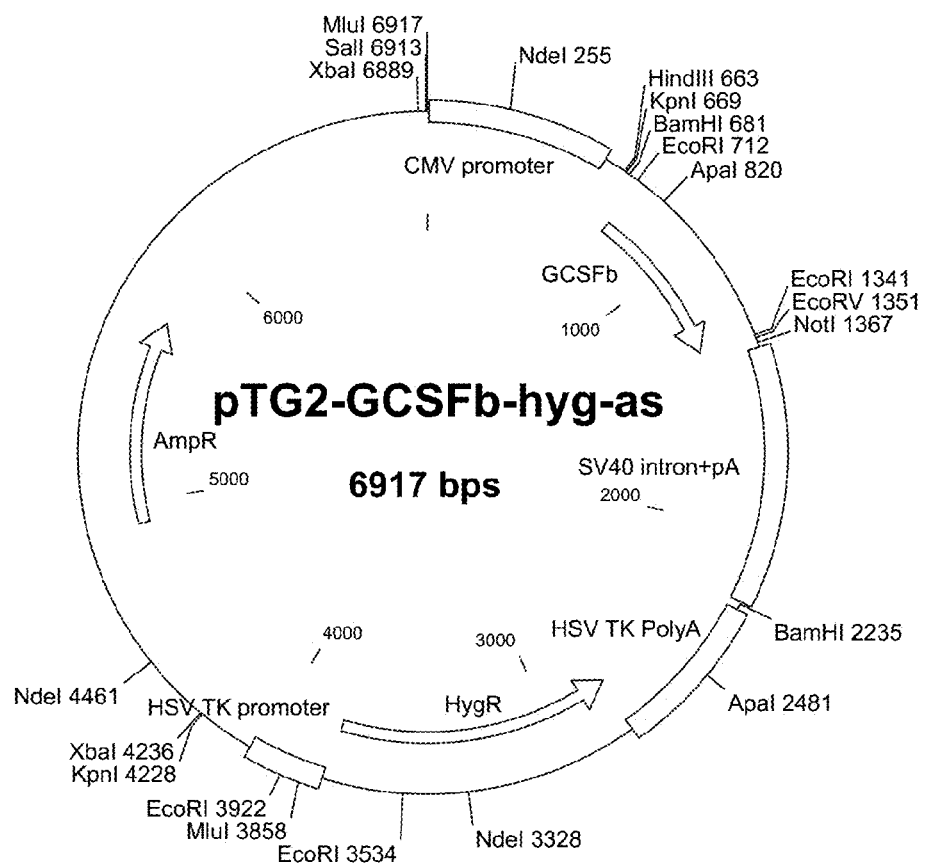
FIG. 14 shows the vector pTG2-GCSFb-hyg-as. The vector comprises 6,917 bps, the exact sequence thereof being shown in SEQ ID NO:25.

PCR2.1d2-GCSFb was digested with HindIII and NotI, the 705 bp GCSFb cDNA fragment was isolated and ligated into pTG2-hyg-as vector, which was linearized with HindIII and NotI. The resulting pTG2-GCSFb-hyg-as vector is shown in FIG. 14.

Example 2

Expression of Target Proteins in Different Cell Lines and Different Vectors

Figure 4:
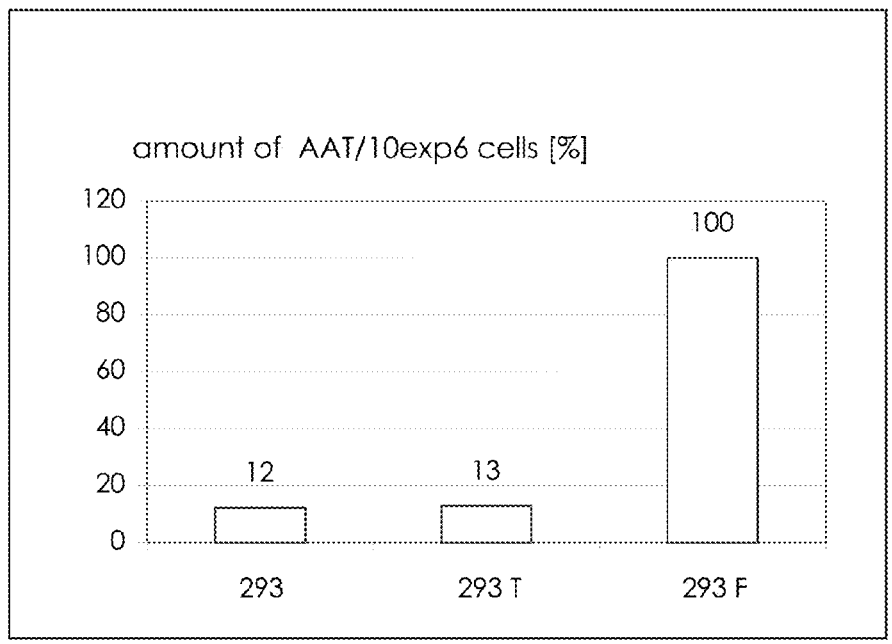
FIG. 4: Transient transfection of different human embryonic kidney cells with vectors coding for alpha-1-antitrypsin. A cell line comparison in transient transfection studies is shown. The amount (%) of alpha-1-antitrypsin (A1AT) expressed per $10^6$ cells is shown for 293, 293T and 293F cells. The A1AT amount expressed in 293F cells transiently transfected with pcDNA3.1-A1AT has been set as 100%.
Figure 5:
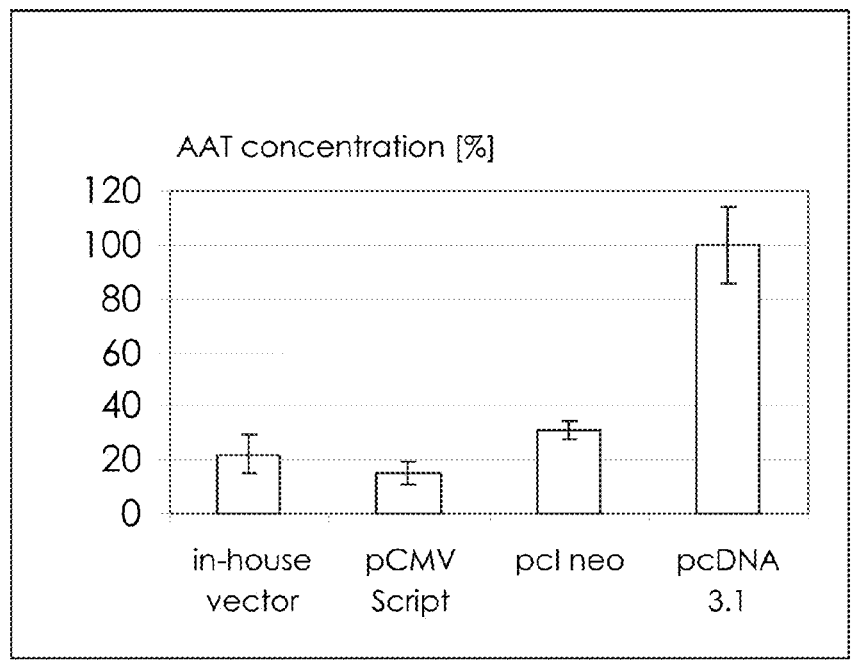
FIG. 5: Transient transfection of 293F cell line with different vectors coding for alpha-1-antitrypsin. A comparison of A1AT concentrations expressed from different vectors using transiently transfected freestyle 293F cell line is shown. The expression level of A1AT pcDNA3.1-A1AT has been set as 100%. Various other vectors carrying the A1AT gene were also tested: An in-house vector pTG1-A1AT (an in-house vector for producing human recombinant A1AT as shown in FIG. 10), the pCMV Script® A1AT (Stratagene) and pcI neo-A1AT (Promega) were compared against the pcDNA3.1-A1AT (pcDNA3.1). None of the other vectors came close to the high expression levels observed with pcDNA3.1-A1AT.
Figure 6:
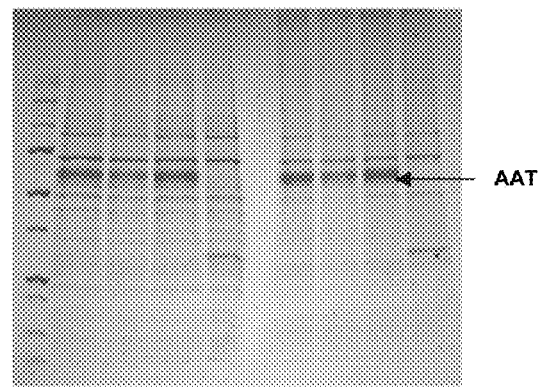
FIG. 6: SDS-PAGE and Western blot of cell culture supernatant. Aliquots of the supernatant of freestyle 293F cells transiently transfected with pcDNA3.1-A1AT (lanes 1-3 and 6-8) or with a GFP-expressing control plasmid (lanes 4 and 8) were analysed both by SDS-PAGE and Western blot. Lane 1 contains a size marker, and lane 5 is empty. The band for A1AT is marked with an arrow. Also visible is the 27 kDa band corresponding to GFP in lanes 4 and 8.
Figure 6:
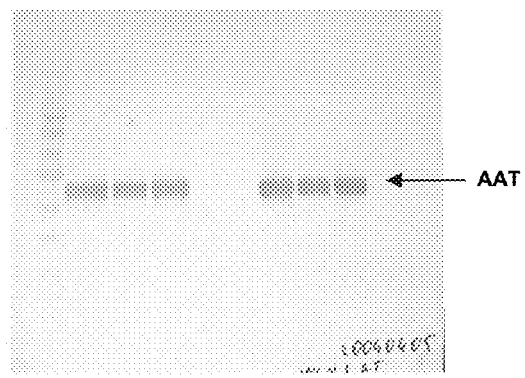

When optimizing the present method for recombinant protein production the ability for high levels of expression of different cell lines—all carrying a vector comprising the recombinant gene for Alpha-1-antitrypsin (A1AT)—was tested. CHO, BHK and other cell lines were found to produce less recombinant protein in transient transfection assays compared to the 293T cell line. Therefore other human embryonic kidney cell line derivates were examined. The results are shown in FIGS. 4 to 6.

Example 3

Transient Transfection of 293T and 293 Cells in Serum Containing Medium as Comparison to 293F Cells, which were Transfected and Cultured Under Serum-Free Conditions $0.1-0.2 \times 10^6$ viable cells of 293T or 293 cells were plated into 6-well. On the next day cells were transfected using Calcium phosphate method (Biotechniques 6:7 632-638 (1988)): 4 µg of plasmid DNA were diluted in 0.1× TE buffer (ad 200 µl transfection mix), mixed gently, 20 µl 2.5 M $CaCl_2$ and 100 µl 2×HBS were added to the transfection sample. The transfection sample was incubated for 20 min at room temperature. After 6 h incubation medium was exchanged and cells were then incubated for 48 h.

Example 4

Serum-Free Transfection and Expression of Target Proteins in 293F Cells in Serum-Free Medium 28 ml suspension culture was prepared with a cell density of $10^6$ viable 293F cells (on the same day of the transfection experiment). A lipid-DNA complex was prepared by diluting 30 µg of plasmid DNA in Opti-MEM® I (Invitrogen) to a total volume of 1 ml, and 40 µl of 293Fectin® was diluted in Opti-MEM® I to a total volume of 1 ml. After the 5 min incubation at room temperature, diluted DNA was added to 293Fectin® to obtain a total volume of 2 ml. The transfected samples have been incubated for 20 min at room temperature in the dark. 2 ml of the transfection mix was added to the 28 ml 293F suspension culture (final cell density is $1 \times 10^6$ cells/mil). The transfected 293F cells were incubated at 37° C./humidified atmosphere of 8% $CO_2$ in air on an orbital shaker rotating at 125 rpm for 72 h.

A: Transfection and Expression of A1AT:

The results of those experiments comparing 293F with 293 and 293T cells are shown in FIG. 4. In all experiments a defined quantity of cells ($10^6$ cells) were transfected with pcDNA3.1-A1AT. The amount of A1AT expressed in these different cell lines was compared. The expressed amount of A1AT in 293 F cells was set as 100%. As can be seen from FIG. 4, 293 and 293 T cells produced only 12-13% of the amount of A1AT than 293F cells.

Moreover, it was tested whether different vector backbones influence the amount of recombinant protein produced in 293F cells. The coding sequence for human Alpha-1-antitrypsin (A1AT) was inserted into pTG (in-house vectors), pCMV Script® (Stratagene), pcI neo (Promega) as well as into the pcDNA3.1™ vector.

The expression level of A1AT from pcDNA3.1-A1AT was set as 100%. None of the other vectors came close to the high expression observed with pcDNA™ 3.1-A1AT. It was found that pcDNA 3.1-A1AT produced the greatest amount of A1AT as detected with ELISA (see FIG. 5). The in-house vector expressed only an amount of 20% and the other commercial vectors revealed a range of 15-30% compared to the amount of A1AT expressed from pcDNA 3.1. Therefore pcDNA 3.1 was chosen for all further experiments.

In summary, different cell lines had been transiently transfected with pcDNA3.1™ carrying the A1AT gene. It was shown that the serum-free 293F cell line expresses 7-times more A1AT per $10^6$ cells than 293T and 293 cells. Therefore freestyle 293 F cell line were chosen for stable transfection experiments.

The results of transient transfection experiments are shown in FIG. 6. The top panel (A) shows the SDS-PAGE analysis of the supernatant of 6 different transfection trials using different transfection vectors. Derived from analytical Figures it can be concluded that the α1-antitrypsin present in the analysed cell culture supernatants is of good quality as can be deduced from the ratio of activity to antigen being 1 (data not shown). Validity of the test results can be deduced from the fact that the negative control does not show α1-antitrypsin activity nor antigen.

The molecular weight distribution analysed by SDS-PAGE shows well comparable pictures for the three α1-antitrypsin containing samples. In the negative control, besides the lack in the α1-antitrypsin representing band, an additional band at a molecular weight of 27 kD is visible as expected.

By analysis using western blotting (using an anti human al-antitrypsin primary antibody) the protein can be identified in the expected molecular weight region under reducing conditions. Split products are not visible.

The black arrow points to the prominent band which corresponds to the 52 kDa recombinant protein alpha-1-antitrypsin. Also visible is a band corresponding to the 27 kDa GFP protein in lanes 4 and 8, which was transiently expressed as control in cell line freestyle 293 F cells. The additional bands in lane 1, 2, 3 and 5, 6 and 7 are host cell proteins (from freestyle 293 F cells). The lower panel (B) shows the Western Blot analysis. The results are identical except that due to the higher stringency of the assay, the results appear cleaner, and only the band corresponding to the A1AT is visible.

Figure 8:
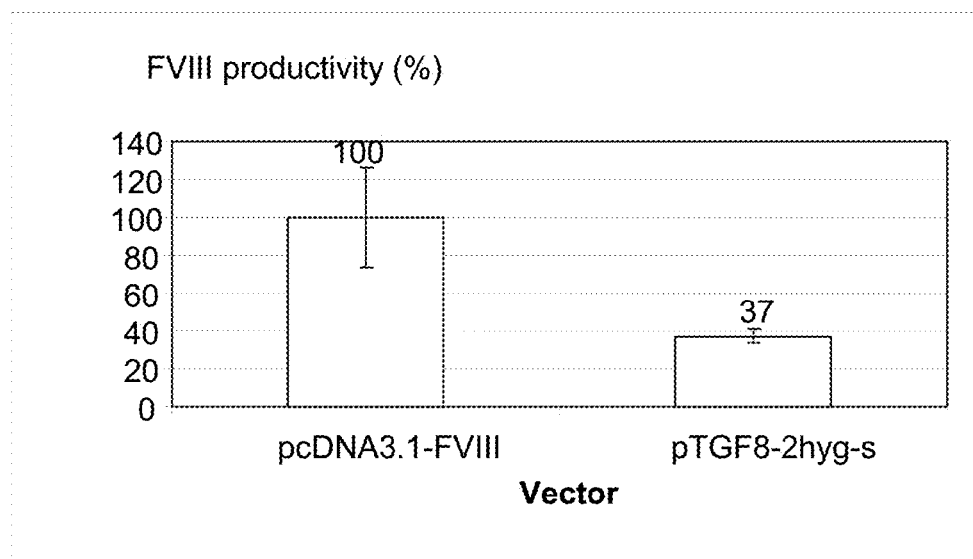
FIG. 8: Comparison of the average amount of produced factor VIII of the best three stably transfected clones, transfecting 293 and 293F cells with pcDNA3.1-FVIII and the in-house vector pTGF8-2hyg-s, the exact sequence thereof being given in SEQ ID NO:7.

B: Transfection and Expression of FVIII:

In FIG. 8 the average amount of factor VIII of the best three stably transfected clones is shown. The average amount of factor VIII of the three best clones expressed with pcDNA-FVIII vector is set as 100% productivity. A comparison with the in-house vector pTGF8-2hyg-s reveals almost 3-fold higher productivity of factor VIII with pcDNA3.1-FVIII vector in 293F cells.

C: Transfection and Expression of FIX:

In stably transfected 293F cells using pcDNA3.1-FIX and a pUC 19/X based vector pTGF36 (see WO 01/70968) expressing factor IX, almost 3-fold higher productivity could be shown with the use of pcDNA3.1 vector in 293F cells as can be seen in the following Table 1.

TABLE 1

FIX productivity in 293 and 293F cells after stable transfection with pcDNA3.1 and pTG2 vector

| Substrate cell line/ vector | FIX productivity in % [mIU/$10^6$ cells day] | |
| --- | --- | --- |
| | pcDNA3.1-FIX | pTG2-FIX |
| 293 (+serum) | 100% | — |
| 293F (−serum) | 100% | 60% |

Example 5

Production of G-CSFb

A. Transfection of 293F Cells in Serum-Free Medium, Transient Transfection:

28 ml suspension culture of 293F cells with a cell density of $1.1 \times 10^6$ viable 293F cells per ml was prepared on the same day of the transfection experiment. A lipid-DNA complex was prepared by diluting 30 µg of plasmid DNA (pcDNA3.1-G-CSFb) in Opti-MEM® I (Invitrogen) to a total volume of 1 ml and 30 µl of Lipofectamine 2000 CD was diluted in Opti-MEM® I to a total volume of 1 ml. After 5 min incubation at room temperature, diluted DNA was added to Lipofectamine 2000 CD to obtain a total volume of 2 ml. The transfection samples were incubated for 20 min at room temperature in the dark. 2 ml of the transfection mix was added to the 28 ml 293F suspension culture (final cell density is $1 \times 10^6$ cells per ml). The transfected 293F cells were incubated at 37° C./humidified atmosphere of 8% $CO_2$ in air on an orbital shaker rotating at 125 rpm for 72 h.

B. Stable Transfection:

72 h after transient transfection as set forth in A. above, a suitable number of cells ($10^5$ and $10^6$ cells) were transferred into a flat dish for sedimentation to establish adherent growth. Selection pressure was started after 2 to 50 h, preferably 48 h post transfer into the flat dish. The preferred selective agent was hygromycine with a concentration of 75 µg/ml. The pressure was maintained for at least 10 to 20 days, preferably for 14 days, whereby the hygromcine supplemented medium was exchanged all 2 to 3 days.

C. Selection of Best G-CSF Producer Clones Using the Analysis and Picking Robot ClonePixFL (Genetix):

FreeStyle 293F cells stably transfected as described in B. above were seeded in semi-solid methyl-celluloses based medium containing an appropriate antibiotic for selection of clones after about two days and a labelled antibody for detection of the highest producer clones via fluorescence. Large numbers (thousands) of clones were analyzed using ClonePixFL (Genetix) with respect to the cell number and to G-CSF secretion in order to subsequently pick only a few hundred G-CSF best producer clones. In contrast to other known methods, where non-producer clones and mixed clones are randomly picked as well, the use of ClonePixFL allows picking of fast growing clones, which are high producers only, originated from single cells. The picked cells are expanded in microtiter plates and later in spin tubes, cell culture flasks and fermenters under serum-free conditions for the complete procedure.

Here as well the whole stable transfection procedure is generated under serum-free conditions. Additionally, during the whole following expansion and cell culture procedure, the cell did not have any contact to serum or animal derived proteins.

During expansion, the best clones are selected with respect to robustness, high growth rate, viability and production of active G-CSF as measured in ELISA format. After this selection phase, the picked clones are cultured under serum-free conditions without antibiotic supplements. 293F cells were cultured completely serum-free during the whole procedure, medium was exchanged every other day. Up-scaling of the cells was performed under completely serum-free conditions from Erlenmeyer flasks in Kühner Shakers to higher volumes in wave reactor (Wave Biotech Europe). During this selection the number is reduced again to only a few best producing clones. Correct cDNA sequence, mRNA content and behaviour upon fermentation are the criteria to identify the best clone(s) for subcloning. For this, cells of the selected clone(s) are plated, analyzed and picked with ClonePixFL, and then expanded and selected as described before. Subcloning is an essential step in order to select again for better producer clones to eliminate possible genetic variations in the plated subpopulation of the clone. After subcloning, the selected clone(s) are banked again under serum-free conditions. The expressed recombinant human G-CSF protein is characterized biochemically in more detail.

Figure 15:
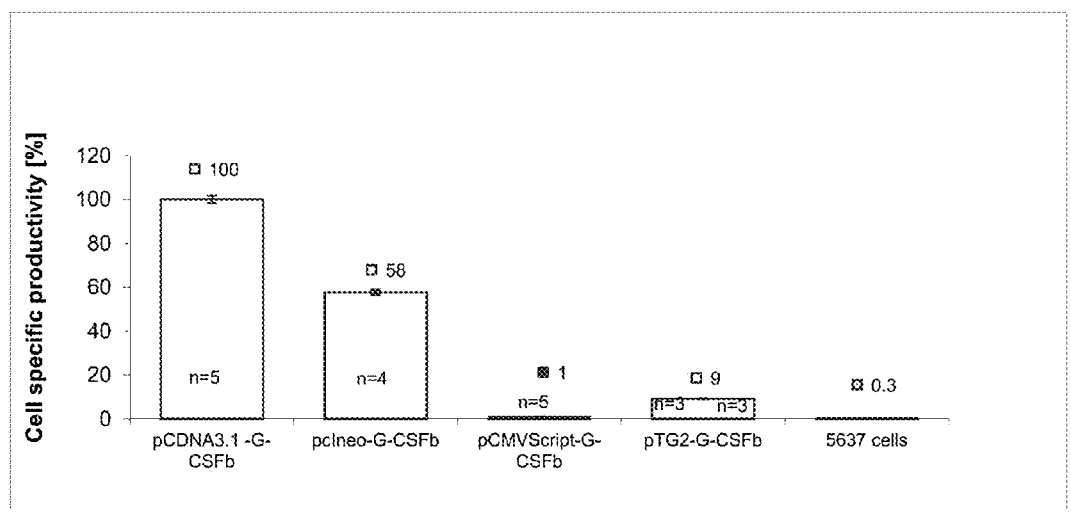
FIG. 15 compares the amount of rhG-CSF produced by different expression constructs according to Example 9.

D. Determination of Human G-CSF Concentration by ELISA:

The quantity of the rhG-CSF expressed by the FeeStyle 293F cell lines thus obtained was determined by ELISA, and the yield of protein obtained with cells transfected with different vectors was compared (see FIG. 15). As expected from the expression experiments with FIX and A1AT described in Examples 2 and 3, here again a combination of the vector pcDNA 3.1-GCSFb with the 293F cell line showed the highest productivity and was therefore used for production of recombinant human G-CSFb.

Figure 16:
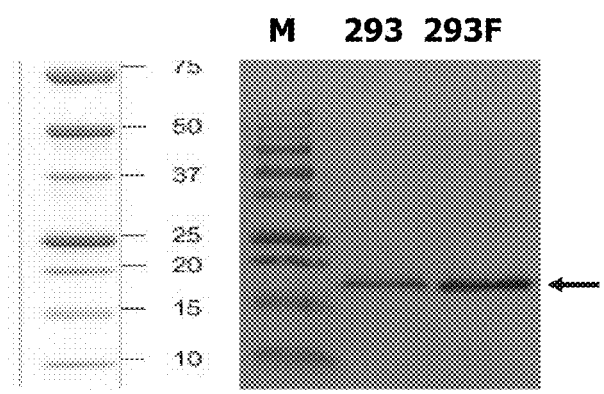
FIG. 16 shows a western blot of rhG-CSF produced according to Example 9.

E. Western Blot of rhG-CSF in Reducing SDS PAGE:

10 µl G-CSF produced in supernatants from HEK293 and HEK293F cells was analyzed on 15% SDS PAGE and western blot. Detection of G-CSF was done via BAF214-bio/SA-HRP/DAB (see FIG. 16). The arrow indicates the monomeric band of rhG-CSF of the correct molecular mass.

| Sequence Listing, Free text | | | |
|---|---|---|---|
| SEQ ID NO: 1: pcDNA3.1-FIX, | | | |
| Molecule: | 6960 bps DNA, circular | | |
| Type | Start | End | Name/Description |
| REGION | 209 | 863 | CMV promoter |
| REGION | 895 | 911 | MCS" |
| GENE | 939 | 2324 | hFIX |
| GENE | 2328 | 2339 | SV40'/SV40 polya + intron |
| REGION | 2340 | 2370 | 'MCS |
| REGION | 2381 | 2595 | BGH pA |
| REGION | 2658 | 3071 | f1 origin |
| REGION | 3136 | 3460 | SV40 promoter |
| GENE | 3478 | 4501 | HygR |
| REGION | 4514 | 4886 | SV40 pA |
| REGION | 5819 | 5146 | C PUC origin |
| GENE | 6824 | 5964 | C AmpR(complementary strand) |
| SEQ ID NO: 2: pcDNA3.1-A1AT | | | |
| Molecule: | 6914 bps DNA, circular | | |
| Type | Start | End | Name/Description |
| REGION | 209 | 863 | CMV promoter |
| GENE | 913 | 2259 | A1AT |
| GENE | 2328 | 2339 | SV40'/SV40 polya + intron |
| REGION | 2335 | 2549 | BGH pA |
| REGION | 2612 | 3025 | f1 origin |
| REGION | 3090 | 3414 | SV40 promoter |
| GENE | 3432 | 4455 | HygR |
| REGION | 4468 | 4840 | SV40 pA |
| REGION | 5773 | 5100 | C PUC origin |
| GENE | 6778 | 5918 | C AmpR(complementary strand) |
| SEQ ID NO: 3: pcDNA3.1-FVIII | | | |
| Molecule: | 9975 bps DNA, circular | | |
| Type | Start | End | Name/Description |
| REGION | 1 | 655 | CMV promoter |
| GENE | 783 | 3082 | human FVIII domains A1 and A2 |
| GENE | 3083 | 3104 | remainder of B-domain and add. nts |
| GENE | 3105 | 5162 | human factor FVIII domains A3, C1, C2 |
| REGION | 5188 | 5402 | BGH pA |
| REGION | 5465 | 5878 | f1 origin |
| REGION | 5943 | 6267 | SV40 promoter |
| GENE | 6285 | 7308 | HygR |
| REGION | 7321 | 7693 | SV40 pA |
| REGION | 8626 | 7953 | C PUC origin |
| GENE | 9631 | 8771 | C AmpR(complementary strand) |
| SEQ ID NO: 4: pcDNA 3.1 sequence published by Invitrogen | | | |
| Molecule: | 5597 bps DNA, circular | | |
| Type | Start | End | Name/Description |
| REGION | 209 | 863 | CMV promoter |
| REGION | 895 | 1010 | MCS |
| REGION | 1021 | 1235 | BGH pA |
| REGION | 1298 | 1711 | f1 origin |
| REGION | 1776 | 2100 | SV40 promoter |
| GENE | 2118 | 3141 | HygR |
| REGION | 3154 | 3526 | SV40 pA |
| REGION | 4456 | 3786 | C PUC origin |
| GENE | 5461 | 4601 | C AmpR(complementary strand) |
| SEQ ID NO: 5: pcDNA3.1Hygro(+)-zz, having 3 additonal nt "GGT" at position 4380 compared to SEQ ID NO:4 | | | |
| Molecule: | 5600 bps DNA, circular | | |
| Type | Start | End | Name/Description |
| REGION | 209 | 863 | CMV promoter |
| REGION | 895 | 1010 | MCS |

-continued

| | Sequence Listing, Free text | | |
|---|---|---|---|
| REGION | 1021 | 1235 | BGH pA |
| REGION | 1298 | 1711 | f1 origin |
| REGION | 1776 | 2100 | SV40 promoter |
| GENE | 2118 | 3141 | HygR |
| REGION | 3154 | 3526 | SV40 pA |
| REGION | 4459 | 3786 | C PUC origin |
| GENE | 5464 | 4604 | C AmpR(complementary strand) |

| SEQ ID NO: 6: vector pTG1-A1AT |
|---|

| SEQ ID NO: 7: vector pFGF8-hyg-s |
|---|

| Molecule: | 10705 bps DNA, circular | | |
|---|---|---|---|
| Type | Start | End | Name/Description |
| REGION | 1 | 586 | CMV promoter |
| GENE | 676 | 2975 | hFVIII domain A1 and A2 |
| Gene | 2976 | 2997 | hinge remaining of B-domain and add. nts |
| Gene | 2998 | 5055 | hFVIII domains A3, C1, C2 |
| Region | 5067 | 5916 | polyA intron and polyA site from SV40 |
| Gene | 5928 | 7910 | Hygromycin resistance |
| Region | 8346 | 8423 | progesterone responsive element |
| Gene | 8681 | 9469 | ampicillin resistance |

SEQ ID NO: 8: human wild-type factor VIII cDNA
SEQ ID NO: 9: human wild-type factor VIII
SEQ ID NOs: 10-12: linker peptides
SEQ ID NO: 13: cDNA of hFVII a-form
SEQ ID NO: 14: cDNA of hFVII b-form
SEQ ID NO: 15: cDNA of human GCSF a-form, CDS: 41-661
SEQ ID NO: 16: cDNA of human GCSF b-form, CDS: 41-652
SEQ ID NO: 17: cDNA of human GCSF c-form, CDS: 229-828
SEQ ID NO: 18: cDNA of hvWF
SEQ ID NOs: 19 and 20: G-CSF forward and reverse primer

| SEQ ID NO: 21: vector PCR2.1d2-GCSFb | | |
|---|---|---|
| Molecule: | 4542 bps DNA; circular | |
| Start | End | feature/Name |
| 293 | 907 | GCSFb |
| 1159 | 1596 | f1 origin |
| 1930 | 2724 | KanR |
| 2742 | 3602 | AmpR |
| 3747 | 4420 | pUC origin |

| SEQ ID NO: 22: vector pcDNA3.1-hyg(+)-GCSFb | | |
|---|---|---|
| Molecule: | 6237 bps DNA, circular | |
| Start | End | Feature/Name |
| 209 | 863 | CMV promoter |
| 970 | 1584 | GCSFb |
| 1658 | 1872 | BGH pA |
| 1935 | 2348 | f1 origin |
| 2413 | 2737 | SV40 promoter |
| 2755 | 3778 | HygR |
| 3791 | 4163 | SV40 pA |
| 5096 | 4423C | PUC origin |
| 6101 | 5241 | C AmpR |

| SEQ ID NO: 23: vector pCINeo-GCSFb | | |
|---|---|---|
| Molecule: | 6101 bps DNA, circular | |
| Start | End | Feature/Name |
| 1 | 1022 | CMV promoter/intron |
| 1106 | 1720 | GCSFb |
| 1796 | 2017 | SV40 PolyA |
| 2112 | 2567 | fi origin |
| 2629 | 3047 | SV40 enhancer/promoter |

-continued

| Sequence Listing, Free text | | |
|---|---|---|
| 3092 | 3886 | NeoR |
| 3950 | 3998 | PolyA |
| 4409 | 5269 | AmpR |

| SEQ ID NO: 24: vector pCMVScript_GCSFb, | | |
|---|---|---|
| Molecule: | 4920 bps DNA, circular | |
| Start | End | Feature/Name |
| 1 | 602 | CMV promoter |
| 728 | 1342 | GCSFb |
| 1453 | 1836 | SV40 PolyA |
| 1974 | 2280 | f1 origin |
| 2449 | 2787 | SV40 promoter |
| 2822 | 3613 | NeoR |
| 3614 | 4063 | HSV-TK PolyA |

| SEQ ID NO: 25: pTG2-GCSFb-hyg-as | | |
|---|---|---|
| Molecule: | 6917 bps DNA, circular | |
| Start | End | Feature/Name |
| 5 | 591 | CMV promoter |
| 722 | 1336 | GCSFb |
| 1383 | 2228 | SV40 intron + pA |
| 2767 | 2255 | C HSV TK PolyA |
| 3782 | 2745 | C HygR |
| 4044 | 3796 | C HSV TK promoter |
| 4916 | 5704 | AmpR |

SEQ ID NO: 26: cDNA of human GCSF b-form
SEQ ID NO: 27: human GCSF b-form protein Applicants incorporate by reference the material contained in the accompanying computer readable Sequence Listing identified as SEQ_ST25.txt, having a file creation date of Dec. 19, 2007, 2:47 p.m., and a file size of 192 kilobytes.

What is claimed is:

1. A method for recombinant production of a human target protein, the method comprising culturing a stably transfected immortalized human cell line comprising a nucleic acid sequence comprising a gene encoding a human target protein or a derivative or mutant thereof, a promoter, and a bovine growth hormone polyadenylation (polyA) signal, the promoter and polyA signal linked to the 5' and 3' end of the gene encoding the human target protein, respectively, under conditions sufficient for production of the human target protein, wherein the stably transfected immortalized human cell line is prepared by transfecting an immortalized human host cell line under serum-free conditions with a transfection vector comprising the nucleic acid sequence, to result in the stably transfected immortalized human cell line.

2. The method of claim 1, wherein the human host cell line is a human foetal kidney (HEK) cell line.

3. The method of claim 1, wherein the human target protein is a human plasma protein selected from the group consisting of:
   a blood clotting factor selected from the group consisting of factor IX, factor VIII (wild-type and B-domain deleted), Factor VII/VIIa, and von Willebrand factor (vWF);
   a growth factor;
   a colony-stimulating factor (CSF) selected from the group consisting of granulocyte stimulating factor (G-CSF), macrophage CSF (M-CSF), and granulocyte-macrophage CSF (GM-CSF);
   a cytokine;
   a protease inhibitor selected from the group consisting of alpha-1-antitrypsin (A1AT) and chymotrypsin;
   a transport protein selected from the group consisting of a hormone, an inhibitory protein and a regulatory acting protein; and
   combinations thereof.

4. The method of claim 1, wherein the human target protein is selected from the group consisting of:
   blood clotting factor IX encoded by bps 939 to 2324 of SEQ ID NO:1;
   human A1AT encoded by bps 913 to 2259 of SEQ ID NO:2;
   wild-type factor VIII SEQ ID NO:9;
   B-domain deleted human factor VIII;
   factor VII/VIIa encoded by SEQ ID NOS:13 and 14;
   G-CSF encoded by SEQ ID NOS:15, 16, and 17;
   vWF encoded by SEQ ID NO:18;
   and combinations thereof.

5. The method of claim 3, wherein the growth factor is erythropoietin.

6. The method of claim 3, wherein the cytokine is an interleukin.

7. The method of claim 1, where the human target protein is B-domain deleted human factor VIII encoded by bps 783 to 5162 of SEQ ID NO:3.

8. The method of claim 1, where the human target protein is mature.

9. The method of claim 3, where the human target protein is mature.

10. The method of claim 4, where the human target protein is mature.

11. The method of claim 7, where the human target protein is mature.

12. The method of claim 11, where the human cell line is 293F.

13. A method for recombinant production of a human target protein or a derivative or mutant thereof, the method comprising culturing a stably transfected immortalized human cell line prepared by transfecting an immortalized human host cell line under serum-free conditions with a transfection vector comprising an origin of replication a nucleic acid sequence comprising a gene encoding a human target protein or a derivative or mutant thereof, a promoter, and a bovine growth hormone polyadenylation (polyA) signal, the promoter and polyA signal linked to the 5' and 3' end of the gene encoding the human target protein or derivative or mutant thereof, respectively, under conditions sufficient for production of the human target protein or derivative or mutant thereof, where the derivative or mutant of the human target protein provides for at least one of increased stability, increased half-life, and increased recovery.

14. The method of claim 13, wherein the human host cell line is a human foetal kidney (HEK) cell line.

15. The method of claim 13 wherein the human target protein is a human plasma protein selected from the group consisting of:
    a blood clotting factor selected from the group consisting of factor IX, factor VIII (wild-type and B-domain deleted), Factor VII/VIIa, and von Willebrand factor (vWF);
    a growth factor;
    a colony-stimulating factor (CSF) selected from the group consisting of granulocyte stimulating factor (G-CSF), macrophage CSF (M-CSF), and granulocyte-macrophage CSF (GM-CSF);
    a cytokine;
    a protease inhibitor selected from the group consisting of alpha-1-antitrypsin (A1AT) and chymotrypsin;
    a transport protein selected from the group consisting of a hormone, an inhibitory protein and a regulatory acting protein; and
    combinations thereof.

16. The method of claim 13, wherein the human target protein is selected from the group consisting of:
    blood clotting factor IX encoded by bps 939 to 2324 of SEQ ID NO:1;
    human A1AT encoded by bps 913 to 2259 of SEQ ID NO:2;
    wild-type factor VIII SEQ ID NO:9;
    B-domain deleted human factor VIII encoded by bps 783 to 5162 of SEQ ID NO:3;
    factor VII/VIIa encoded by SEQ ID NOS:13 and 14;
    G-CSF encoded by SEQ ID NOS:15, 16, and 17;
    vWF encoded by SEQ ID NO:18;
    and combinations thereof.

17. The method of claim 15, wherein the growth factor is erythropoietin.

18. The method of claim 15, wherein the cytokine is an interleukin.

19. The method of claim 13, where the human target protein is B-domain deleted human factor VIII encoded by bps 783 to 5162 of SEQ ID NO:3.

20. The method of claim 13, where the human target protein is mature.

21. The method of claim 15, where the human target protein is mature.

22. The method of claim 16, where the human target protein is mature.

23. The method of claim 18, where the human target protein is mature.

24. The method of claim 22, where the human cell line is 293F.

* * * * *

SEQUENCE LISTING

<160> NUMBER OF SEQ ID NOS: 27

<210> SEQ ID NO 1
<211> LENGTH: 6960
<212> TYPE: DNA
<213> ORGANISM: Artificial Sequence
<220> FEATURE:
<223> OTHER INFORMATION: vector pcDNA3.1-FIX

<400> SEQUENCE: 1

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat taagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
```

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgcat gccaattccg caaaggttat gcagcgcgtg aacatgatca    960
tggcagaatc accaggcctc atcaccatct gccttttagg atatctactc agtgctgaat   1020
gtacagtttt tcttgatcat gaaaacgcca acaaaattct gaatcggcca agaggtata   1080
attcaggtaa attggaagag tttgttcaag ggaaccttga gagagaatgt atggaagaaa   1140
agtgtagttt tgaagaagca cgagaagttt ttgaaaacac tgaaagaaca actgaatttt   1200
ggaagcagta tgttgatgga gatcagtgtg agtccaatcc atgtttaaat ggcggcagtt   1260
gcaaggatga cattaattcc tatgaatgtt ggtgtccctt tggatttgaa ggaaagaact   1320
gtgaattaga tgtaacatgt aacattaaga atggcagatg cgagcagttt tgtaaaaata   1380
gtgctgataa caaggtggtt tgctcctgta ctgagggata tcgacttgca gaaaaccaga   1440
agtcctgtga accagcagtg ccatttccat gtggaagagt ttctgtttca caacttcta   1500
agctcacccg tgctgagact gttttcctg atgtggacta tgtaaattct actgaagctg   1560
aaaccatttt ggataacatc actcaaagca cccaatcatt taatgacttc actcgggttg   1620
ttggtggaga agatgccaaa ccaggtcaat tcccttggca ggttgttttg aatggtaaag   1680
ttgatgcatt ctgtggaggc tctatcgtta tgaaaaatg gattgtaact gctgcccact   1740
gtgttgaaac tggtgttaaa attacagttg tcgcaggtga acataatatt gaggagacag   1800
aacatacaga gcaaaagcga aatgtgattc gaattattcc tcaccacaac tacaatgcag   1860
ctattaataa gtacaaccat gacattgccc ttctggaact ggacgaaccc ttagtgctaa   1920
acagctacgt tacacctatt tgcattgctg acaaggaata cacgaacatc ttcctcaaat   1980
ttggatctgg ctatgtaagt ggctggggaa gagtcttcca caagggaga tcagctttag   2040
ttcttcagta ccttagagtt ccacttgttg accgagccac atgtcttcga tctacaaagt   2100
tcaccatcta taacaacatg ttctgtgctg gcttccatga aggaggtaga gattcatgtc   2160
aaggagatag tggggacccc catgttactg aagtggaagg gaccagtttc ttaactggaa   2220
ttattagctg gggtgaagag tgtgcaatga aggcaaata tggaatatat accaaggtat   2280
cccggtatgt caactggatt aaggaaaaaa caaagctcac ttaatgggat cggtcgagcg   2340
gccgctcgag tctagagggc ccgtttaaac ccgctgatca gcctcgactg tgccttctag   2400
ttgccagcca tctgttgttt gcccctcccc cgtgccttcc ttgaccctgg aaggtgccac   2460
tcccactgtc ctttcctaat aaaatgagga aattgcatcg cattgtctga gtaggtgtca   2520
ttctattctg ggggtgggg tggggcagga cagcaagggg gaggattggg aagacaatag   2580
caggcatgct ggggatgcgg tgggctctat ggcttctgag gcggaaagaa ccagctgggg   2640
ctctaggggg tatccccacg cgccctgtag cggcgcatta gcgcggcgg gtgtggtggt   2700
tacgcgcagc gtgaccgcta cacttgccag cgccctagcg cccgctcctt tcgctttctt   2760
cccttccttt ctcgccacgt tcgccggctt tccccgtcaa gctctaaatc ggggggctccc   2820
tttagggttc cgatttagtg ctttacggca cctcgacccc aaaaaacttg attagggtga   2880
tggttcacgt agtgggccat cgccctgata gacggttttt cgccctttga cgttggagtc   2940
```

```
cacgttcttt aatagtggac tcttgttcca aactggaaca acactcaacc ctatctcggt   3000
ctattctttt gatttataag ggattttgcc gatttcggcc tattggttaa aaaatgagct   3060
gatttaacaa aaatttaacg cgaattaatt ctgtggaatg tgtgtcagtt agggtgtgga   3120
aagtccccag gctccccagc aggcagaagt atgcaaagca tgcatctcaa ttagtcagca   3180
accaggtgtg gaaagtcccc aggctcccca gcaggcagaa gtatgcaaag catgcatctc   3240
aattagtcag caaccatagt cccgcccta actccgccca tcccgcccct aactccgccc   3300
agttccgccc attctccgcc ccatggctga ctaattttt ttatttatgc agaggccgag   3360
gccgcctctg cctctgagct attccagaag tagtgaggag gcttttttgg aggcctaggc   3420
ttttgcaaaa agctcccggg agcttgtata tccattttcg gatctgatca gcacgtgatg   3480
aaaaagcctg aactcaccgc gacgtctgtc gagaagtttc tgatcgaaaa gttcgacagc   3540
gtctccgacc tgatgcagct ctcggagggc gaagaatctc gtgctttcag cttcgatgta   3600
ggagggcgtg gatatgtcct gcgggtaaat agctgcgccg atggtttcta caaagatcgt   3660
tatgtttatc ggcactttgc atcggccgcg ctcccgattc cggaagtgct tgacattggg   3720
gaattcagcg agagcctgac ctattgcatc tcccgccgtg cacagggtgt cacgttgcaa   3780
gacctgcctg aaaccgaact gcccgctgtt ctgcagccgg tcgcggaggc catggatgcg   3840
atcgctgcgg ccgatcttag ccagacgagc gggttcggcc cattcggacc gcaaggaatc   3900
ggtcaataca ctacatggcg tgatttcata tgcgcgattg ctgatcccca tgtgtatcac   3960
tggcaaactg tgatggacga caccgtcagt gcgtccgtcg cgcaggctct cgatgagctg   4020
atgctttggg ccgaggactg ccccgaagtc cggcacctcg tgcacgcgga tttcggctcc   4080
aacaatgtcc tgacggacaa tggccgcata acagcggtca ttgactggag cgaggcgatg   4140
ttcggggatt cccaatacga ggtcgccaac atcttcttct ggaggccgtg gttggcttgt   4200
atggagcagc agacgcgcta cttcgagcgg aggcatccgg agcttgcagg atcgccgcgg   4260
ctccgggcgt atatgctccg cattggtctt gaccaactct atcagagctt ggttgacggc   4320
aatttcgatg atgcagcttg ggcgcagggt cgatgcgacg caatcgtccg atccggagcc   4380
gggactgtcg ggcgtacaca atcgcccgc agaagcgcgg ccgtctggac cgatggctgt   4440
gtagaagtac tcgccgatag tggaaaccga cgccccagca ctcgtccgag ggcaaaggaa   4500
tagcacgtgc tacgagattt cgattccacc gccgccttct atgaaaggtt gggcttcgga   4560
atcgttttcc gggacgccgg ctggatgatc ctccagcgcg ggatctcat gctggagttc   4620 ttcgcccacc ccaacttgtt tattgcagct tataatggtt acaaataaag caatagcatc   4680
acaaatttca caaataaagc atttttttca ctgcattcta gttgtggttt gtccaaactc   4740
atcaatgtat cttatcatgt ctgtataccg tcgacctcta gctagagctt ggcgtaatca   4800
tggtcatagc tgtttcctgt gtgaaattgt tatccgctca caattccaca acatacga   4860 gccgaagca taaagtgtaa agcctggggt gcctaatgag tgagctaact cacattaatt   4920
gcgttgcgct cactgcccgc tttccagtcg ggaaacctgt cgtgccagct gcattaatga   4980
atcggccaac gcgcggggag aggcggtttg cgtattgggc gctcttccgc ttcctcgctc   5040
actgactcgc tgcgctcggt cgttcggctg cggcgagcgg tatcagctca ctcaaaggcg   5100
gtaatacggt tatccacaga atcaggggat aacgcaggaa agaacatgtg agcaaaaggc   5160
cagcaaaagg ccaggaaccg taaaaaggcc gcgttgctgg cgtttttcca taggctccgc   5220 cccccctgacg agcatcacaa aaatcgacgc tcaagtcaga ggtggcgaaa cccgacagga   5280
```

```
ctataaagat accaggcgtt tccccctgga agctccctcg tgcgctctcc tgttccgacc    5340
ctgccgctta ccggatacct gtccgccttt ctcccttcgg gaagcgtggc gctttctcat    5400
agctcacgct gtaggtatct cagttcggtg taggtcgttc gctccaagct gggctgtgtg    5460
cacgaacccc ccgttcagcc cgaccgctgc gccttatccg gtaactatcg tcttgagtcc    5520
aacccggtaa gacacgactt atcgccactg gcagcagcca ctggtaacag gattagcaga    5580
gcgaggtatg taggcggtgc tacagagttc ttgaagtggt ggcctaacta cggctacact    5640
agaagaacag tatttggtat ctgcgctctg ctgaagccag ttaccttcgg aaaaagagtt    5700
ggtagctctt gatccggcaa acaaaccacc gctggtagcg gtggtttttt tgtttgcaag    5760
cagcagatta cgcgcagaaa aaaggatctc aagaagatc ctttgatctt ttctacgggg     5820
tctgacgctc agtggaacga aaactcacgt taagggattt tggtcatgag attatcaaaa    5880
aggatcttca cctagatcct tttaaattaa aaatgaagtt ttaaatcaat ctaaagtata    5940
tatgagtaaa cttggtctga cagttaccaa tgcttaatca gtgaggcacc tatctcagcg    6000
atctgtctat ttcgttcatc catagttgcc tgactccccg tcgtgtagat aactacgata    6060
cgggagggct taccatctgg ccccagtgct gcaatgatac cgcgagaccc acgctcaccg    6120
gctccagatt tatcagcaat aaaccagcca gccggaaggg ccgagcgcag aagtggtcct    6180
gcaactttat ccgcctccat ccagtctatt aattgttgcc gggaagctag agtaagtagt    6240
tcgccagtta atagtttgcg caacgttgtt gccattgcta caggcatcgt ggtgtcacgc    6300
tcgtcgtttg gtatggcttc attcagctcc ggttcccaac gatcaaggcg agttacatga    6360
tcccccatgt tgtgcaaaaa agcggttagc tccttcggtc ctccgatcgt tgtcagaagt    6420
aagttggccg cagtgttatc actcatggtt atggcagcac tgcataattc tcttactgtc    6480
atgccatccg taagatgctt ttctgtgact ggtgagtact caaccaagtc attctgagaa    6540
tagtgtatgc ggcgaccgag ttgctcttgc ccggcgtcaa tacgggataa taccgcgcca    6600
catagcagaa ctttaaaagt gctcatcatt ggaaaacgtt cttcggggcg aaaactctca    6660
aggatcttac cgctgttgag atccagttcg atgtaaccca ctcgtgcacc caactgatct    6720
tcagcatctt ttactttcac cagcgtttct gggtgagcaa aaacaggaag gcaaaatgcc    6780
gcaaaaaagg gaataagggc gacacggaaa tgttgaatac tcatactctt cctttttcaa    6840
tattattgaa gcatttatca gggttattgt ctcatgagcg gatacatatt tgaatgtatt    6900
tagaaaaata aacaaatagg ggttccgcgc acatttcccc gaaaagtgcc acctgacgtc    6960
```

<210> SEQ ID NO 2
<211> LENGTH: 6914
<212> TYPE: DNA
<213> ORGANISM: Artificial Sequence
<220> FEATURE:
<223> OTHER INFORMATION: vector pcDNA3.1-A1AT

<400> SEQUENCE: 2

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
```

```
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgtga atcgacaatg ccgtcttctg tctcgtgggg catcctcctg    960
ctggcaggcc tgtgctgcct ggtccctgtc tccctggctg aggatcccca gggagatgct   1020
gcccagaaga cagatacatc ccaccatgat caggatcacc caaccttcaa caagatcacc   1080
cccaacctgg ctgagttcgc cttcagccta taccgccagc tggcacacca gtccaacagc   1140
accaatatct tcttctcccc agtgagcatc gctacagcct ttgcaatgct ctccctgggg   1200
accaaggctg acactcacga tgaaatcctg gagggcctga atttcaacct cacggagatt   1260
ccggaggctc agatccatga aggcttccag gaactcctcc gtaccctcaa ccagccagac   1320
agccagctcc agctgaccac cggcaatggc ctgttcctca gcgagggcct gaagctagtg   1380
gataagtttt tggaggatgt taaaaagttg taccactcag aagccttcac tgtcaacttc   1440
ggggacaccg aagaggccaa gaaacagatc aacgattacg tggagaaggg tactcaaggg   1500
aaaattgtgg atttggtcaa ggagcttgac agagacacag ttttgctct ggtgaattac   1560 atcttctta aaggcaaatg ggagagaccc tttgaagtca aggacaccga ggaagaggac   1620
ttccacgtgg accaggtgac caccgtgaag gtgcctatga tgaagcgttt aggcatgttt   1680
aacatccagc actgtaagaa gctgtccagc tgggtgctgc tgatgaaata cctgggcaat   1740
gccaccgcca tcttcttcct gcctgatgag gggaaactac agcacctgga aaatgaactc   1800
acccacgata tcatcaccaa gttcctggaa aatgaagaca gaaggtctgc cagcttacat   1860
ttacccaaac tgtccattac tggaacctat gatctgaaga gcgtcctggg tcaactgggc   1920
atcactaagg tcttcagcaa tggggctgac ctctccgggg tcacagagga ggcacccctg   1980
aagctctcca aggccgtgca taaggctgtg ctgaccatcg acgagaaagg gactgaagct   2040
gctggggcca tgtttttaga ggccataccc atgtctatcc ccccgaggt caagttcaac   2100 aaacccttg tcttcttaat gattgaacaa aataccaagt ctcccctctt catgggaaaa   2160
gtggtgaatc ccacccaaaa ataactgcct ctcgctcctc aaccctcc ctccatccct   2220 ggccccctcc ctggatgaca ttaaagaagg ggtaccgca agggcgaatt ctgcagatat   2280
ccatcacact ggcggccgct cgagtctaga gggcccgttt aaacccgctg atcagcctcg   2340
actgtgcctt ctagttgcca gccatctgtt gtttgcccct cccccgtgcc ttccttgacc   2400
ctggaaggtg ccactcccac tgtcctttcc taataaaatg aggaaattgc atcgcattgt   2460
ctgagtaggt gtcattctat tctggggggt ggggtgggc aggacagcaa ggggaggat   2520 tgggaagaca atagcaggca tgctgggat gcggtgggct ctatggcttc tgaggcggaa   2580
agaaccagct ggggctctag ggggtatccc cacgcgccct gtagcggcgc attaagcgcg   2640
gcgggtgtgg tggttacgcg cagcgtgacc gctacacttg ccagcgccct agcgcccgct   2700
cctttcgctt tcttcccttc ctttctcgcc acgttcgccg gctttccccg tcaagctcta   2760
```

```
aatcggggc tcccttagg gttccgattt agtgctttac ggcacctcga ccccaaaaaa    2820
cttgattagg gtgatggttc acgtagtggg ccatcgccct gatagacggt ttttcgccct    2880
ttgacgttgg agtccacgtt ctttaatagt ggactcttgt tccaaactgg aacaacactc    2940
aaccctatct cggtctattc ttttgattta taagggattt tgccgatttc ggcctattgg    3000
ttaaaaaatg agctgatta acaaaaattt aacgcgaatt aattctgtgg aatgtgtgtc    3060
agttagggtg tggaaagtcc ccaggctccc cagcaggcag aagtatgcaa agcatgcatc    3120
tcaattagtc agcaaccagg tgtggaaagt ccccaggctc ccagcaggc agaagtatgc    3180
aaagcatgca tctcaattag tcagcaacca tagtcccgcc cctaactccg cccatcccgc    3240
ccctaactcc gcccagttcc gcccattctc cgccccatgg ctgactaatt ttttttattt    3300
atgcagaggc cgaggccgcc tctgcctctg agctattcca gaagtagtga ggaggctttt    3360
ttggaggcct aggcttttgc aaaaagctcc cgggagcttg tatatccatt ttcggatctg    3420
atcagcacgt gatgaaaaag cctgaactca ccgcgacgtc tgtcgagaag tttctgatcg    3480
aaaagttcga cagcgtctcc gacctgatgc agctctcgga gggcgaagaa tctcgtgctt    3540
tcagcttcga tgtaggaggg cgtggatatg tcctgcgggt aaatagctgc gccgatggtt    3600
tctacaaaga tcgttatgtt tatcggcact ttgcatcggc cgcgctcccg attccggaag    3660
tgcttgacat tggggaattc agcgagagcc tgacctattg catctcccgc cgtgcacagg    3720
gtgtcacgtt gcaagacctg cctgaaaccg aactgcccgc tgttctgcag ccggtcgcgg    3780
aggccatgga tgcgatcgct gcggccgatc ttagccagac gagcgggttc ggcccattcg    3840
gaccgcaagg aatcggtcaa tacactacat ggcgtgattt catatgcgcg attgctgatc    3900
cccatgtgta tcactggcaa actgtgatgg acgacaccgt cagtgcgtcc gtcgcgcagg    3960
ctctcgatga gctgatgctt tgggccgagg actgccccga agtccggcac ctcgtgcacg    4020
cggatttcgg ctccaacaat gtcctgacgg acaatggccg cataacagcg gtcattgact    4080
ggagcgaggc gatgttcggg gattcccaat acgaggtcgc caacatcttc ttctggaggc    4140
cgtggttggc ttgtatggag cagcagacgc gctacttcga gcggaggcat ccggagcttg    4200
caggatcgcc gcggctccgg gcgtatatgc tccgcattgg tcttgaccaa ctctatcaga    4260
gcttggttga cggcaatttc gatgatgcag cttgggcgca gggtcgatgc gacgcaatcg    4320
tccgatccgg agccgggact gtcgggcgta cacaaatcgc ccgcagaagc gcggccgtct    4380
ggaccgatgg ctgtgtagaa gtactcgccg atagtggaaa ccgacgcccc agcactcgtc    4440
cgagggcaaa ggaatagcac gtgctacgag atttcgattc caccgccgcc ttctatgaaa    4500
ggttgggctt cggaatcgtt ttccgggacg ccggctggat gatcctccag cgcggggatc    4560
tcatgctgga gttcttcgcc caccccaact tgtttattgc agcttataat ggttacaaat    4620
aaagcaatag catcacaaat ttcacaaata aagcattttt tcactgcat tctagttgtg    4680
gtttgtccaa actcatcaat gtatcttatc atgtctgtat accgtcgacc tctagctaga    4740
gcttggcgta atcatggtca tagctgtttc ctgtgtgaaa ttgttatccg ctcacaattc    4800
cacacaacat acgagccgga agcataaagt gtaaagcctg gggtgcctaa tgagtgagct    4860
aactcacatt aattgcgttg cgctcactgc ccgctttcca gtcgggaaac ctgtcgtgcc    4920
agctgcatta atgaatcggc caacgcgcgg ggagaggcgg tttgcgtatt gggcgctctt    4980
ccgcttcctc gctcactgac tcgctgcgct cggtcgttcg gctgcggcga gcggtatcag    5040
ctcactcaaa ggcggtaata cggttatcca cagaatcagg ggataacgca ggaaagaaca    5100
tgtgagcaaa aggccagcaa aaggccagga accgtaaaaa ggccgcgttg ctggcgtttt    5160
```

| | |
|---|---:|
| tccataggct ccgcccccct gacgagcatc acaaaaatcg acgctcaagt cagaggtggc | 5220 |
| gaaacccgac aggactataa agataccagg cgtttccccc tggaagctcc ctcgtgcgct | 5280 |
| ctcctgttcc gaccctgccg cttaccggat acctgtccgc ctttctccct tcgggaagcg | 5340 |
| tggcgctttc tcatagctca cgctgtaggt atctcagttc ggtgtaggtc gttcgctcca | 5400 |
| agctgggctg tgtgcacgaa ccccccgttc agcccgaccg ctgcgcctta tccggtaact | 5460 |
| atcgtcttga gtccaacccg gtaagacacg acttatcgcc actggcagca gccactggta | 5520 |
| acaggattag cagagcgagg tatgtaggcg gtgctacaga gttcttgaag tggtggccta | 5580 |
| actacggcta cactagaaga acagtatttg gtatctgcgc tctgctgaag ccagttacct | 5640 |
| tcggaaaaag agttggtagc tcttgatccg gcaaacaaac caccgctggt agcggtggtt | 5700 |
| tttttgtttg caagcagcag attacgcgca gaaaaaaagg atctcaagaa gatcctttga | 5760 |
| tcttttctac ggggtctgac gctcagtgga acgaaaactc acgttaaggg attttggtca | 5820 |
| tgagattatc aaaaaggatc ttcacctaga tccttttaaa ttaaaaatga agttttaaat | 5880 |
| caatctaaag tatatatgag taaacttggt ctgacagtta ccaatgctta atcagtgagg | 5940 |
| cacctatctc agcgatctgt ctatttcgtt catccatagt tgcctgactc cccgtcgtgt | 6000 |
| agataactac gatacgggag ggcttaccat ctggccccag tgctgcaatg ataccgcgag | 6060 |
| acccacgctc accggctcca gatttatcag caataaacca gccagccgga agggccgagc | 6120 |
| gcagaagtgg tcctgcaact ttatccgcct ccatccagtc tattaattgt tgccgggaag | 6180 |
| ctagagtaag tagttcgcca gttaatagtt tgcgcaacgt tgttgccatt gctacaggca | 6240 |
| tcgtggtgtc acgctcgtcg tttggtatgg cttcattcag ctccggttcc caacgatcaa | 6300 |
| ggcgagttac atgatccccc atgttgtgca aaaaagcggt tagctccttc ggtcctccga | 6360 |
| tcgttgtcag aagtaagttg gccgcagtgt tatcactcat ggttatggca gcactgcata | 6420 |
| attctcttac tgtcatgcca tccgtaagat gcttttctgt gactggtgag tactcaacca | 6480 |
| agtcattctg agaatagtgt atgcggcgac cgagttgctc ttgcccggcg tcaatacggg | 6540 |
| ataataccgc gccacatagc agaactttaa aagtgctcat cattggaaaa cgttcttcgg | 6600 |
| ggcgaaaact ctcaaggatc ttaccgctgt tgagatccag ttcgatgtaa cccactcgtg | 6660 |
| cacccaactg atcttcagca tcttttactt tcaccagcgt ttctgggtga gcaaaaacag | 6720 |
| gaaggcaaaa tgccgcaaaa aagggaataa gggcgacacg gaaatgttga atactcatac | 6780 |
| tcttcctttt tcaatattat tgaagcattt atcagggtta ttgtctcatg agcggataca | 6840 |
| tatttgaatg tatttagaaa aataaacaaa taggggttcc gcgcacattt ccccgaaaag | 6900 |
| tgccacctga cgtc | 6914 |

<210> SEQ ID NO 3
<211> LENGTH: 9975
<212> TYPE: DNA
<213> ORGANISM: Artificial Sequence
<220> FEATURE:
<223> OTHER INFORMATION: vector pcDNA3.1-FVII

<400> SEQUENCE: 3

| | |
|---|---:|
| cgatgtacgg gccagatata cgcgttgaca ttgattattg actagttatt aatagtaatc | 60 |
| aattacgggg tcattagttc atagcccata tatggagttc cgcgttacat aacttacggt | 120 |
| aaatggcccg cctggctgac cgcccaacga cccccgccca ttgacgtcaa taatgacgta | 180 |
| tgttcccata gtaacgccaa tagggacttt ccattgacgt caatgggtgg agtatttacg | 240 |

```
gtaaactgcc cacttggcag tacatcaagt gtatcatatg ccaagtacgc cccctattga    300
cgtcaatgac ggtaaatggc ccgcctggca ttatgcccag tacatgacct tatgggactt    360
tcctacttgg cagtacatct acgtattagt catcgctatt accatggtga tgcggttttg    420
gcagtacatc aatgggcgtg gatagcggtt tgactcacgg ggatttccaa gtctccaccc    480
cattgacgtc aatgggagtt tgttttggca ccaaaatcaa cgggactttc caaaatgtcg    540
taacaactcc gccccattga cgcaaatggg cggtaggcgt gtacggtggg aggtctatat    600
aagcagagct ctctggctaa ctagagaacc cactgcttac tggcttatcg aaattaatac    660
gactcactat agggagaccc aagctggcta gcgtttaaac ttaagcttgg taccgagctc    720
ggatccacta gtccagtgtg gtggaattct gcagatatcc agcacagtgg cggccgctcg    780
agatgcaaat agagctctcc acctgcttct ttctgtgcct tttgcgattc tgctttagtg    840
ccaccagaag atactacctg ggtgcagtgg aactgtcatg ggactatatg caaagtgatc    900
tcggtgagct gcctgtggac gcaagatttc ctcctagagt gccaaaatct tttccattca    960
acacctcagt cgtgtacaaa aagactctgt ttgtagaatt cacggatcac cttttcaaca   1020
tcgctaagcc aaggccaccc tggatgggtc tgctaggtcc taccatccag gctgaggttt   1080
atgatacagt ggtcattaca cttaagaaca tggcttccca tcctgtcagt cttcatgctg   1140
ttggtgtatc ctactggaaa gcttctgagg gagctgaata tgatgatcag accagtcaaa   1200
gggagaaaga agatgataaa gtcttccctg gtggaagcca tacatatgtc tggcaggtcc   1260
tgaaagagaa tggtccaatg gcctctgacc cactgtgcct tacctactca tatctttctc   1320
atgtggacct ggtaaaagac ttgaattcag gcctcattgg agccctacta gtatgtagag   1380
aagggagtct ggccaaggaa aagacacaga ccttgcacaa atttatacta cttttttgctg   1440 tatttgatga agggaaaagt tggcactcag aaacaaagaa ctccttgatg caggataggg   1500
atgctgcatc tgctcgggcc tggcctaaaa tgcacacagt caatggttat gtaaacaggt   1560
ctctgccagg tctgattgga tgccacagga atcagtcta ttggcatgtg attgaatgg   1620 gcaccactcc tgaagtgcac tcaatattcc tcgaaggtca cacatttctt gtgaggaacc   1680
atcgccaggc gtccttggaa atctcgccaa taactttcct tactgctcaa acactcttga   1740
tggaccttgg acagtttcta ctgttttgtc atatctcttc ccaccaacat gatggcatgg   1800
aagcttatgt caaagtagac agctgtccag aggaacccca actacgaatg aaaaataatg   1860
aagaagcgga agactatgat gatgatctta ctgattctga aatggatgtg gtcaggtttg   1920
atgatgacaa ctctccttcc tttatccaaa ttcgctcagt tgccaagaag catcctaaaa   1980
cttgggtaca ttacattgct gctgaagagg aggactggga ctatgctccc ttagtcctcg   2040
cccccgatga cagaagttat aaaagtcaat atttgaacaa tggccctcag cggattggta   2100
ggaagtacaa aaaagtccga tttatggcat acacagatga aacctttaag actcgtgaag   2160
ctattcagca tgaatcagga atcttgggac ctttacttta tggggaagtt ggagacacac   2220
tgttgattat atttaagaat caagcaagca gaccatataa catctaccct cacggaatca   2280
ctgatgtccg tccttttgta ttcaaggaga t accaaaagg tgtaaaacat ttgaaggatt   2340
ttccaattct gccaggagaa atattcaaat ataaatggac agtgactgta gaagatgggc   2400
caactaaatc agatcctcgg tgcctgaccc gctattactc tagtttcgtt aatatggaga   2460
gagatctagc ttcaggactc attggccctc tcctcatctg ctacaaagaa tctgtagatc   2520
aaagaggaaa ccagataatg tcagacaaga ggaatgtcat cctgttttct gtatttgatg   2580
agaaccgaag ctggtaccct acagagaata tacaacgctt tctccccaat ccagctggag   2640
```

```
tgcagcttga ggatccagag ttccaagcct ccaacatcat gcacagcatc aatggctatg    2700 ttttttgatag tttgcagttg tcagtttgtt tgcatgaggt ggcatactgg tacattctaa   2760
gcattggagc acagactgac ttcctttctg tcttcttctc tggatatacc ttcaaacaca   2820
aaatggtcta tgaagacaca ctcaccctat tcccattctc aggagaaact gtcttcatgt   2880
cgatggaaaa cccaggtcta tggattctgg ggtgccacaa ctcagacttt cggaacagag   2940
gcatgaccgc cttactgaag gtttctagtt gtgacaagaa cactggtgat tattacgagg   3000
acagttatga agatatttca gcatacttgc tgagtaaaaa caatgccatt gaaccaagaa   3060
gcttctccca gaattcaaga catcaagctt atcgataccg tcgaggggaa ataactcgta   3120
ctactcttca gtcagatcaa gaggaaattg actatgatga taccatatca gttgaaatga   3180
agaaggaaga ttttgacatt tatgatgagg atgaaaatca gagcccccgc agctttcaaa   3240
agaaaacacg acactatttt attgctgcag tggagaggct ctgggattat gggatgagta   3300
gctccccaca tgttctaaga aacagggctc agagtggcag tgtccctcag ttcaagaaag   3360 ttgtttttcca ggaatttact gatggctcct ttactcagcc cttataccgt ggagaactaa   3420
atgaacattt gggactcctg gggccatata aagagcaga agttgaagat aatatcatgg   3480
taactttcag aaatcaggcc tctcgtccct attccttcta ttctagcctt atttcttatg   3540
aggaagatca gaggcaagga gcagaaccta gaaaaaactt tgtcaagcct aatgaaacca   3600
aaacttactt ttggaaagtg caacatcata tggcacccac taaagatgag tttgactgca   3660
aagcctgggc ttatttctct gatgttgacc tggaaaaaga tgtgcactca ggcctgattg   3720 gacccccttct ggtctgccac actaacacac tgaaccctgc tcatgggaga caagtgacag   3780
tacaggaatt tgctctgttt ttcaccatct ttgatgagac caaaagctgg tacttcactg   3840 aaaaatatgga aagaaactgc agggctccct gcaatatcca gatggaagat cccacttttta  3900 aagagaatta tcgcttccat gcaatcaatg gctacataat ggatacacta cctggcttag   3960
taatggctca ggatcaaagg attcgatggt atctgctcag catgggcagc aatgaaaaca   4020
tccattctat tcatttcagt ggacatgtgt tcactgtacg aaaaaaagag gagtataaaa   4080
tggcactgta caatctctat ccaggtgttt ttgagacagt ggaaatgtta ccatccaaag   4140
ctggaatttg gcgggtggaa tgccttattg gcgagcatct acatgctggg atgagcacac   4200
tttttctggt gtacagcaat aagtgtcaga ctcccctggg aatggcttct ggacacatta   4260
gagattttca gattacagct tcaggacaat atggacagtg ggccccaaag ctggccagac   4320
ttcattattc cggatcaatc aatgcctgga gcaccaagga gccctttttct tggatcaagg   4380 tggatctgtt ggcaccaatg attattcacg gcatcaagac ccagggtgcc cgtcagaagt   4440
tctccagcct ctacatctct cagtttatca tcatgtatag tcttgatggg aagaagtggc   4500
agacttatcg aggaaattcc actggaacct taatggtctt cttttggcaat gtggattcat   4560 ctgggataaa acacaatatt tttaaccctc caattattgc tcgatacatc cgtttgcacc   4620
caactcatta tagcattcgc agcactcttc gcatggagtt gatgggctgt gatttaaata   4680
gttgcagcat gccattggga atggagagta aagcaatatc agatgcacag attactgctt   4740
catcctactt taccaatatg tttgccacct ggtctccttc aaaagctcga cttcacctcc   4800
aagggaggag taatgcctgg agacctcagg tgaataatcc aaaagagtgg ctgcaagtgg   4860
acttccagaa gacaatgaaa gtcacaggag taactactca gggagtaaaa tctctgctta   4920
ccagcatgta tgtgaaggag ttcctcatct ccagcagtca agatggccat cagtggaccc   4980
```

-continued

```
tcttttttca gaatggcaaa gtaaaggttt tcagggaaa tcaagactcc ttcacacctg    5040
tggtgaactc tctagaccca ccgttactga ctcgctacct tcgaattcac ccccagagtt    5100
gggtgcacca gattgccctg aggatggagg ttctgggctg cgaggcacag gacctctact    5160
gagcggcccg tttaaacccg ctgatcagcc tcgactgtgc cttctagttg ccagccatct    5220
gttgtttgcc cctcccccgt gccttccttg accctggaag gtgccactcc cactgtcctt    5280
tcctaataaa atgaggaaat tgcatcgcat tgtctgagta ggtgtcattc tattctgggg    5340
ggtggggtgg ggcaggacag caaggggggag gattgggaag acaatagcag gcatgctggg    5400
gatgcggtgg gctctatggc ttctgaggcg aaagaacca gctggggctc tagggggtat    5460
ccccacgcgc cctgtagcgg cgcattaagc gcggcgggtg tggtggttac gcgcagcgtg    5520
accgctacac ttgccagcgc cctagcgccc gctcctttcg ctttcttccc ttcctttctc    5580
gccacgttcg ccggctttcc ccgtcaagct ctaaatcggg gctccctttt agggttccga    5640
tttagtgctt tacggcacct cgaccccaaa aaacttgatt agggtgatgg ttcacgtagt    5700
gggccatcgc cctgatagac ggtttttcgc cctttgacgt tggagtccac gttctttaat    5760
agtggactct tgttccaaac tggaacaaca ctcaaccctta tctcggtcta ttcttttgat    5820
ttataaggga ttttgccgat tcggcctat tggttaaaaa atgagctgat ttaacaaaaa    5880
tttaacgcga attaattctg tggaatgtgt gtcagttagg gtgtggaaag tccccaggct    5940
ccccagcagg cagaagtatg caaagcatgc atctcaatta gtcagcaacc aggtgtggaa    6000
agtccccagg ctccccagca ggcagaagta tgcaaagcat gcatctcaat tagtcagcaa    6060
ccatagtccc gcccctaact ccgcccatcc cgccctaac tccgcccagt ccgcccatt    6120 ctccgcccca tggctgacta attttttta tttatgcaga ggccgaggcc gcctctgcct    6180
ctgagctatt ccagaagtag tgaggaggct ttttttggagg cctaggcttt tgcaaaaagc    6240
tcccgggagc ttgtatatcc attttcggat ctgatcagca cgtgatgaaa aagcctgaac    6300
tcaccgcgac gtctgtcgag aagtttctga tcgaaaagtt cgacagcgtc tccgacctga    6360
tgcagctctc ggagggcgaa gaatctcgtg ctttcagctt cgatgtagga gggcgtggat    6420
atgtcctgcg ggtaaatagc tgcgccgatg gtttctacaa agatcgttat gtttatcggc    6480
actttgcatc ggccgcgctc ccgattccgg aagtgcttga cattggggaa ttcagcgaga    6540
gcctgaccta ttgcatctcc cgccgtgcac agggtgtcac gttgcaagac ctgcctgaaa    6600
ccgaactgcc cgctgttctg cagccggtcg cggaggccat ggatgcgatc gctgcggccg    6660
atcttagcca gacgagcggg ttcggcccat tcggaccgca aggaatcggt caatacacta    6720
catggcgtga tttcatatgc gcgattgctg atccccatgt gtatcactgg caaactgtga    6780
tggacgacac cgtcagtgcg tccgtcgcgc aggctctcga tgagctgatg ctttgggccg    6840
aggactgccc cgaagtccgg cacctcgtgc acgcggattt cggctccaac aatgtcctga    6900
cggacaatgg ccgcataaca gcggtcattg actggagcga ggcgatgttc ggggattccc    6960
aatacgaggt cgccaacatc ttcttctgga ggccgtggtt ggcttgtatg gagcagcaga    7020
cgcgctactt cgagcggagg catccggagc ttgcaggatc gccgcggctc cgggcgtata    7080
tgctccgcat tggtcttgac caactctatc agagcttggt tgacggcaat ttcgatgatg    7140
cagcttgggc gcagggtcga tgcgacgcaa tcgtccgatc cggagccggg actgtcgggc    7200
gtacacaaat cgcccgcaga agcgcggccg tctggaccga tggctgtgta gaagtactcg    7260
ccgatagtgg aaaccgacgc cccagcactc gtccgagggc aaaggaatag cacgtgctac    7320
gagatttcga ttccaccgcc gccttctatg aaaggttggg cttcggaatc gttttccggg    7380
```

```
acgccggctg gatgatcctc cagcgcgggg atctcatgct ggagttcttc gcccacccca    7440
acttgtttat tgcagcttat aatggttaca aataaagcaa tagcatcaca aatttcacaa    7500
ataaagcatt tttttcactg cattctagtt gtggtttgtc caaactcatc aatgtatctt    7560
atcatgtctg tataccgtcg acctctagct agagcttggc gtaatcatgg tcatagctgt    7620
ttcctgtgtg aaattgttat ccgctcacaa ttccacacaa catacgagcc ggaagcataa    7680
agtgtaaagc ctggggtgcc taatgagtga gctaactcac attaattgcg ttgcgctcac    7740
tgcccgcttt ccagtcggga aacctgtcgt gccagctgca ttaatgaatc ggccaacgcg    7800
cggggagagg cggtttgcgt attgggcgct cttccgcttc ctcgctcact gactcgctgc    7860
gctcggtcgt tcggctgcgg cgagcggtat cagctcactc aaaggcggta atacggttat    7920
ccacagaatc aggggataac gcaggaaaga acatgtgagc aaaaggccag caaaaggcca    7980
ggaaccgtaa aaaggccgcg ttgctggcgt ttttccatag gctccgcccc cctgacgagc    8040
atcacaaaaa tcgacgctca agtcagaggt ggcgaaaccc gacaggacta taaagatacc    8100
aggcgtttcc ccctggaagc tccctcgtgc gctctcctgt tccgaccctg ccgcttaccg    8160
gatacctgtc cgcctttctc ccttcgggaa gcgtggcgct ttctcatagc tcacgctgta    8220
ggtatctcag ttcggtgtag tcgttcgct ccaagctggg ctgtgtgcac gaaccccccg    8280
ttcagcccga ccgctgcgcc ttatccggta actatcgtct tgagtccaac ccggtaagac    8340
acgacttatc gccactggca gcagccactg gtaacaggat tagcagagcg aggtatgtag    8400
gcggtgctac agagttcttg aagtggtggc ctaactacgg ctacactaga agaacagtat    8460
ttggtatctg cgctctgctg aagccagtta ccttcggaaa aagagttggt agctcttgat    8520
ccggcaaaca aaccaccgct ggtagcggtg gtttttttgt ttgcaagcag cagattacgc    8580
gcagaaaaaa aggatctcaa gaagatcctt tgatcttttc tacggggtct gacgctcagt    8640
ggaacgaaaa ctcacgttaa gggattttgg tcatgagatt atcaaaaagg atcttcacct    8700
agatcctttt aaattaaaaa tgaagtttta aatcaatcta agtatatat gagtaaactt    8760 ggtctgacag ttaccaatgc ttaatcagtg aggcacctat ctcagcgatc tgtctatttc    8820
gttcatccat agttgcctga ctccccgtcg tgtagataac tacgatacgg gagggcttac    8880
catctggccc cagtgctgca atgataccgc gagacccacg ctcaccggct ccagatttat    8940
cagcaataaa ccagccagcc ggaagggccg agcgcagaag tggtcctgca actttatccg    9000
cctccatcca gtctattaat tgttgccggg aagctagagt aagtagttcg ccagttaata    9060
gtttgcgcaa cgttgttgcc attgctacag gcatcgtggt gtcacgctcg tcgtttggta    9120
tggcttcatt cagctccggt tcccaacgat caaggcgagt tacatgatcc cccatgttgt    9180
gcaaaaaagc ggttagctcc ttcggtcctc cgatcgttgt cagaagtaag ttggccgcag    9240
tgttatcact catggttatg gcagcactgc ataattctct tactgtcatg ccatccgtaa    9300
gatgcttttc tgtgactggt gagtactcaa ccaagtcatt ctgagaatag tgtatgcggc    9360
gaccgagttg ctcttgcccg gcgtcaatac gggataatac cgcgccacat agcagaactt    9420
taaaagtgct catcattgga aaacgttctt cggggcgaaa actctcaagg atcttaccgc    9480
tgttgagatc cagttcgatg taacccactc gtgcacccaa ctgatcttca gcatctttta    9540
ctttcaccag cgtttctggg tgagcaaaaa caggaaggca aaatgccgca aaaagggaa    9600 taagggcgac acggaaatgt tgaatactca tactcttcct ttttcaatat tattgaagca    9660
tttatcaggg ttattgtctc atgagcggat acatatttga atgtatttag aaaaataaac    9720
```

```
aaataggggt tccgcgcaca tttccccgaa aagtgccacc tgacgtcgac ggatcgggag    9780
atctcccgat cccctatggt gcactctcag tacaatctgc tctgatgccg catagttaag    9840
ccagtatctg ctccctgctt gtgtgttgga ggtcgctgag tagtgcgcga gcaaaattta    9900
agctacaaca aggcaaggct tgaccgacaa ttgcatgaag aatctgctta gggttaggcg    9960
ttttgcgctg cttcg                                                     9975
```

<210> SEQ ID NO 4
<211> LENGTH: 5597
<212> TYPE: DNA
<213> ORGANISM: Artificial Sequence
<220> FEATURE:
<223> OTHER INFORMATION: vector pcDNA3.1

<400> SEQUENCE: 4

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgcc ccattgacgc aaatgggcg      780 gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattctgc     960
agatatccag cacagtggcg gccgctcgag tctagagggc ccgtttaaac ccgctgatca    1020
gcctcgactg tgccttctag ttgccagcca tctgttgttt gcccctcccc cgtgccttcc    1080
ttgaccctgg aaggtgccac tcccactgtc ctttcctaat aaaatgagga aattgcatcg    1140
cattgtctga gtaggtgtca ttctattctg ggggtgggg tggggcagga cagcaagggg     1200
gaggattggg aagacaatag caggcatgct ggggatgcgg tgggctctat ggcttctgag    1260
gcggaaagaa ccagctgggg ctctaggggg tatccccacg cgccctgtag cggcgcatta    1320
agcgcggcgg gtgtggtggt tacgcgcagc gtgaccgcta cacttgccag cgccctagcg    1380
cccgctcctt tcgctttctt cccttccttt ctcgccacgt tcgccggctt tccccgtcaa    1440
gctctaaatc gggggctccc tttagggttc cgatttagtg ctttacggca cctcgacccc    1500
aaaaaacttg attagggtga tggttcacgt agtgggccat cgccctgata gacggttttt    1560
cgccctttga cgttggagtc acgttctttt aatagtggac tcttgttcca aactggaaca    1620
acactcaacc ctatctcggt ctattctttt gatttataag ggattttgcc gatttcggcc    1680
tattggttaa aaaatgagct gatttaacaa aaatttaacg cgaattaatt ctgtggaatg    1740
tgtgtcagtt agggtgtgga agtccccag gctccccagc aggcagaagt atgcaaagca     1800
```

```
tgcatctcaa ttagtcagca accaggtgtg gaaagtcccc aggctcccca gcaggcagaa    1860
gtatgcaaag catgcatctc aattagtcag caaccatagt cccgcccta actccgccca     1920 tcccgcccct aactccgccc agttccgccc attctccgcc ccatggctga ctaattttt     1980 ttatttatgc agaggccgag gccgcctctg cctctgagct attccagaag tagtgaggag    2040
gcttttttgg aggcctaggc ttttgcaaaa agctcccggg agcttgtata tccattttcg    2100
gatctgatca gcacgtgatg aaaaagcctg aactcaccgc gacgtctgtc gagaagtttc    2160
tgatcgaaaa gttcgacagc gtctccgacc tgatgcagct ctcggagggc gaagaatctc    2220
gtgctttcag cttcgatgta ggagggcgtg gatatgtcct gcgggtaaat agctgcgccg    2280
atggtttcta caaagatcgt tatgtttatc ggcactttgc atcggccgcg ctcccgattc    2340
cggaagtgct tgacattggg gaattcagcg agagcctgac ctattgcatc tcccgccgtg    2400
cacagggtgt cacgttgcaa gacctgcctg aaaccgaact gcccgctgtt ctgcagccgg    2460
tcgcggaggc catggatgcg atcgctgcgg ccgatcttag ccagacgagc gggttcggcc    2520
cattcggacc gcaaggaatc ggtcaataca ctacatggcg tgatttcata tgcgcgattg    2580
ctgatcccca tgtgtatcac tggcaaactg tgatggacga caccgtcagt gcgtccgtcg    2640
cgcaggctct cgatgagctg atgctttggg ccgaggactg ccccgaagtc cggcacctcg    2700
tgcacgcgga tttcggctcc aacaatgtcc tgacggacaa tggccgcata acagcggtca    2760
ttgactggag cgaggcgatg ttcggggatt cccaatacga ggtcgccaac atcttcttct    2820
ggaggccgtg gttggcttgt atggagcagc agacgcgcta cttcgagcgg aggcatccgg    2880
agcttgcagg atcgccgcgg ctccgggcgt atatgctccg cattggtctt gaccaactct    2940
atcagagctt ggttgacggc aatttcgatg atgcagcttg gcgcagggt cgatgcgacg     3000 caatcgtccg atccggagcc gggactgtcg ggcgtacaca atcgcccgc agaagcgcgg      3060 ccgtctggac cgatggctgt gtagaagtac tcgccgatag tggaaaccga cgccccagca    3120
ctcgtccgag ggcaaaggaa tagcacgtgc tacgagattt cgattccacc gccgccttct    3180
atgaaaggtt gggcttcgga atcgttttcc gggacgccgg ctggatgatc ctccagcgcg    3240
gggatctcat gctggagttc ttcgcccacc ccaacttgtt tattgcagct tataatggtt    3300
acaaataaag caatagcatc acaaatttca caaataaagc attttttca ctgcattcta     3360 gttgtggttt gtccaaactc atcaatgtat cttatcatgt ctgtataccg tcgacctcta    3420
gctagagctt ggcgtaatca tggtcatagc tgtttcctgt gtgaaattgt tatccgctca    3480
caattccaca acatacga gccggaagca taaagtgtaa agcctggggt gcctaatgag       3540
tgagctaact cacattaatt gcgttgcgct cactgcccgc tttccagtcg ggaaacctgt    3600
cgtgccagct gcattaatga atcggccaac gcgcggggag aggcggtttg cgtattgggc    3660
gctcttccgc ttcctcgctc actgactcgc tgcgctcggt cgttcggctg cggcgagcgg    3720
tatcagctca ctcaaaggcg gtaatacggt tatccacaga atcaggggat aacgcaggaa    3780
agaacatgtg agcaaaaggc cagcaaaagg ccaggaaccg taaaaaggcc gcgttgctgg    3840 cgttttcca taggctccgc cccctgacg agcatcacaa aaatcgacgc tcaagtcaga      3900
ggtggcgaaa cccgacagga ctataaagat accaggcgtt tccccctgga agctccctcg    3960
tgcgctctcc tgttccgacc ctgccgctta ccggatacct gtccgccttt ctcccttcgg    4020
gaagcgtggc gctttctcat agctcacgct gtaggtatct cagttcggtg taggtcgttc    4080
gctccaagct gggctgtgtg cacgaacccc ccgttcagcc cgaccgctgc gccttatccg    4140
```

```
gtaactatcg tcttgagtcc aacccggtaa gacacgactt atcgccactg gcagcagcca    4200
ctggtaacag gattagcaga gcgaggtatg taggcggtgc tacagagttc ttgaagtggt    4260
ggcctaacta cggctacact agaagaacag tatttggtat ctgcgctctg ctgaagccag    4320
ttaccttcgg aaaagagtt ggtagctctt gatccggcaa acaaaccacc gctggtagcg    4380 gttttttttgt ttgcaagcag cagattacgc gcagaaaaaa aggatctcaa gaagatcctt    4440
tgatcttttc tacggggtct gacgctcagt ggaacgaaaa ctcacgttaa ggattttgg    4500 tcatgagatt atcaaaaagg atcttcacct agatccttt aaattaaaaa tgaagtttta    4560
aatcaatcta agtatatat gagtaaactt ggtctgacag ttaccaatgc ttaatcagtg    4620
aggcacctat ctcagcgatc tgtctatttc gttcatccat agttgcctga ctccccgtcg    4680
tgtagataac tacgatacgg gagggcttac catctggccc cagtgctgca atgataccgc    4740
gagacccacg ctcaccggct ccagatttat cagcaataaa ccagccagcc ggaagggccg    4800
agcgcagaag tggtcctgca actttatccg cctccatcca gtctattaat tgttgccggg    4860
aagctagagt aagtagttcg ccagttaata gtttgcgcaa cgttgttgcc attgctacag    4920
gcatcgtggt gtcacgctcg tcgtttggta tggcttcatt cagctccggt tcccaacgat    4980
caaggcgagt tacatgatcc cccatgttgt gcaaaaaagc ggttagctcc ttcggtcctc    5040
cgatcgttgt cagaagtaag ttggccgcag tgttatcact catggttatg gcagcactgc    5100
ataattctct tactgtcatg ccatccgtaa gatgcttttc tgtgactggt gagtactcaa    5160
ccaagtcatt ctgagaatag tgtatgcggc gaccgagttg ctcttgcccg gcgtcaatac    5220
gggataatac cgcgccacat agcagaactt taaaagtgct catcattgga aaacgttctt    5280
cggggcgaaa actctcaagg atcttaccgc tgttgagatc cagttcgatg taacccactc    5340
gtgcacccaa ctgatcttca gcatctttta ctttcaccag cgtttctggg tgagcaaaaa    5400
caggaaggca aaatgccgca aaaaagggaa taagggcgac acggaaatgt tgaatactca    5460
tactcttcct ttttcaatat tattgaagca tttatcaggg ttattgtctc atgagcggat    5520
acatatttga atgtatttag aaaaataaac aaatagggt tccgcgcaca tttccccgaa    5580
aagtgccacc tgacgtc                                                  5597

<210> SEQ ID NO 5
<211> LENGTH: 5600
<212> TYPE: DNA
<213> ORGANISM: Artificial Sequence
<220> FEATURE:
<223> OTHER INFORMATION: vector cDNA3.1Hygro(+)-zz

<400> SEQUENCE: 5
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg ggggtgggg tggggcagga cagcaagggg   1200
gaggattggg aagacaatag caggcatgct ggggatgcgg tgggctctat ggcttctgag   1260
gcggaaagaa ccagctgggg ctctagggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata acggttttt   1560 cgcccttga cgttggagtc cacgttcttt aatagtggac tcttgttcca aactggaaca   1620
acactcaacc ctatctcggt ctattctttt gatttataag ggattttgcc gatttcggcc   1680
tattggttaa aaaatgagct gatttaacaa aaatttaacg cgaattaatt ctgtggaatg   1740
tgtgtcagtt agggtgtgga agtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccatttcg   2100 gatctgatca gcacgtgatg aaaaagcctg aactcaccgc gacgtctgtc gagaagtttc   2160
tgatcgaaaa gttcgacagc gtctccgacc tgatgcagct ctcggagggc gaagaatctc   2220
gtgctttcag cttcgatgta ggagggcgtg gatatgtcct gcgggtaaat agctgcgccg   2280
atggtttcta caaagatcgt tatgtttatc ggcactttgc atcggccgcg ctcccgattc   2340
cggaagtgct tgacattggg gaattcagcg agagcctgac ctattgcatc tcccgccgtg   2400
cacagggtgt cacgttgcaa gacctgcctg aaaccgaact gcccgctgtt ctgcagccgg   2460
tcgcggaggc catggatgcg atcgctgcgg ccgatcttag ccagacgagc gggttcggcc   2520
cattcggacc gcaaggaatc ggtcaataca ctacatggcg tgatttcata tgcgcgattg   2580
ctgatcccca tgtgtatcac tggcaaactg tgatggacga caccgtcagt gcgtccgtcg   2640
cgcaggctct cgatgagctg atgctttggg ccgaggactg ccccgaagtc cggcacctcg   2700
tgcacgcgga tttcggctcc aacaatgtcc tgacggacaa tggccgcata acagcggtca   2760
ttgactggag cgaggcgatg ttcggggatt cccaatacga ggtcgccaac atcttcttct   2820
ggaggccgtg gttggcttgt atggagcagc agacgcgcta cttcgagcgg aggcatccgg   2880
agcttgcagg atcgccgcgg ctccgggcgt atatgctccg cattggtctt gaccaactct   2940
```

```
atcagagctt ggttgacggc aatttcgatg atgcagcttg ggcgcagggt cgatgcgacg    3000
caatcgtccg atccggagcc gggactgtcg ggcgtacaca aatcgcccgc agaagcgcgg    3060
ccgtctggac cgatggctgt gtagaagtac tcgccgatag tggaaaccga cgccccagca    3120
ctcgtccgag ggcaaaggaa tagcacgtgc tacgagattt cgattccacc gccgccttct    3180
atgaaaggtt gggcttcgga atcgttttcc gggacgccgg ctggatgatc ctccagcgcg    3240
gggatctcat gctggagttc ttcgcccacc ccaacttgtt tattgcagct tataatggtt    3300
acaaataaag caatagcatc acaaatttca caaataaagc attttttttca ctgcattcta    3360 gttgtggttt gtccaaactc atcaatgtat cttatcatgt ctgtataccg tcgacctcta    3420
gctagagctt ggcgtaatca tggtcatagc tgtttcctgt gtgaaattgt tatccgctca    3480
caattccaca acatacga gccggaagca taaagtgtaa agcctggggt gcctaatgag    3540
tgagctaact cacattaatt gcgttgcgct cactgcccgc tttccagtcg ggaaacctgt    3600
cgtgccagct gcattaatga atcggccaac gcgcggggag aggcggtttg cgtattgggc    3660
gctcttccgc ttcctcgctc actgactcgc tgcgctcggt cgttcggctg cggcgagcgg    3720
tatcagctca ctcaaaggcg gtaatacggt tatccacaga atcaggggat aacgcaggaa    3780
agaacatgtg agcaaaaggc cagcaaaagg ccaggaaccg taaaaaggcc gcgttgctgg    3840 cgttttttcca taggctccgc ccccctgacg agcatcacaa aaatcgacgc tcaagtcaga    3900
ggtggcgaaa cccgacagga ctataaagat accaggcgtt ccccctggaa gctccctcg    3960 tgcgctctcc tgttccgacc ctgccgctta ccggatacct gtccgccttt ctcccttcgg    4020
gaagcgtggc gctttctcat agctcacgct gtaggtatct cagttcggtg taggtcgttc    4080
gctccaagct gggctgtgtg cacgaacccc ccgttcagcc cgaccgctgc gccttatccg    4140
gtaactatcg tcttgagtcc aacccggtaa gacacgactt atcgccactg gcagcagcca    4200
ctggtaacag gattagcaga gcgaggtatg taggcggtgc tacagagttc ttgaagtggt    4260
ggcctaacta cggctacact agaagaacag tatttggtat ctgcgctctg ctgaagccag    4320
ttaccttcgg aaaaagagtt ggtagctctt gatccggcaa acaaaccacc gctggtagcg    4380
gtggtttttt tgtttgcaag cagcagatta cgcgcagaaa aaaaggatct caagaagatc    4440
ctttgatctt ttctacgggg tctgacgctc agtggaacga aaactcacgt taagggattt    4500
tggtcatgag attatcaaaa aggatcttca cctagatcct tttaaattaa aaatgaagtt    4560
ttaaatcaat ctaaagtata tatgagtaaa cttggtctga cagttaccaa tgcttaatca    4620
gtgaggcacc tatctcagcg atctgtctat ttcgttcatc catagttgcc tgactccccg    4680
tcgtgtagat aactacgata cgggagggct taccatctgg ccccagtgct gcaatgatac    4740
cgcgagaccc acgctcaccg gctccagatt tatcagcaat aaaccagcca gccggaaggg    4800
ccgagcgcag aagtggtcct gcaactttat ccgcctccat ccagtctatt aattgttgcc    4860
gggaagctag agtaagtagt tcgccagtta atagtttgcg caacgttgtt gccattgcta    4920
caggcatcgt ggtgtcacgc tcgtcgtttg gtatggcttc attcagctcc ggttcccaac    4980
gatcaaggcg agttacatga tcccccatgt tgtgcaaaaa agcggttagc tccttcggtc    5040
ctccgatcgt tgtcagaagt aagttggccg cagtgttatc actcatggtt atggcagcac    5100
tgcataattc tcttactgtc atgccatccg taagatgctt ttctgtgact ggtgagtact    5160
caaccaagtc attctgagaa tagtgtatgc ggcgaccgag ttgctcttgc ccggcgtcaa    5220
tacgggataa taccgcgcca catagcagaa ctttaaaagt gctcatcatt ggaaaacgtt    5280
cttcggggcg aaaactctca aggatcttac cgctgttgag atccagttcg atgtaaccca    5340
```

```
ctcgtgcacc caactgatct tcagcatctt ttactttcac cagcgtttct gggtgagcaa    5400
aaacaggaag gcaaaatgcc gcaaaaaagg gaataagggc gacacggaaa tgttgaatac    5460
tcatactctt cctttttcaa tattattgaa gcatttatca gggttattgt ctcatgagcg    5520
gatacatatt tgaatgtatt tagaaaaata aacaataggg gttccgcgc acatttcccc    5580 gaaaagtgcc acctgacgtc                                                5600
```

<210> SEQ ID NO 6
<211> LENGTH: 5610
<212> TYPE: DNA
<213> ORGANISM: Artificial Sequence
<220> FEATURE:
<223> OTHER INFORMATION: vector pTG1-A1AT

<400> SEQUENCE: 6

```
cgcgttgaca ttgattattg actagttatt aatagtaatc aattacgggg tcattagttc     60
atagcccata tatggagttc cgcgttacat aacttacggt aaatggcccg cctggctgac    120
cgcccaacga cccccgccca ttgacgtcaa taatgacgta tgttcccata gtaacgccaa    180
tagggacttt ccattgacgt caatgggtgg actatttacg gtaaactgcc cacttggcag    240
tacatcaagt gtatcatatg ccaagtacgc cccctattga cgtcaatgac ggtaaatggc    300
ccgcctggca ttatgcccag tacatgacct tatgggactt tcctacttgg cagtacatct    360
acgtattagt catcgctatt accatggtga tgcggttttg gcagtacatc aatgggcgtg    420
gatagcggtt tgactcacgg ggatttccaa gtctccaccc cattgacgtc aatgggagtt    480
tgttttggca ccaaaatcaa cgggactttc caaaatgtcg taacaactcc gccccattga    540
cgcaaatggg cggtaggcgt gtacggtggg aggtctatat aagcagagct ctctggctaa    600
ctagagaacc cactgcttaa ctggcttatc gaaattaata cgactcacta gggagacc     660 ggaagcttgt gaatcgacaa tgccgtcttc tgtctcgtgg ggcatcctcc tgctggcagg    720
cctgtgctgc ctggtccctg tctccctggc tgaggatccc cagggagatg ctgcccagaa    780
gacagataca tcccaccatg atcaggatca cccaaccttc aacaagatca ccccaacct     840 ggctgagttc gccttcagcc tataccgcca gctggcacac cagtccaaca gcaccaatat    900
cttcttctcc ccagtgagca tcgctacagc cttgcaatg ctctccctgg ggaccaaggc    960
tgacactcac gatgaaatcc tggagggcct gaatttcaac ctcacggaga ttccggaggc    1020
tcagatccat gaaggcttcc aggaactcct ccgtaccctc aaccagccag acagccagct    1080
ccagctgacc accggcaatg gcctgttcct cagcgagggc ctgaagctag tggataagtt    1140
tttggaggat gttaaaaagt tgtaccactc agaagccttc actgtcaact tcggggacac    1200
cgaagaggcc aagaaacaga tcaacgatta cgtggagaag ggtactcaag gaaaattgt     1260 ggatttggtc aaggagcttg acagagacac agttttttgct ctggtgaatt acatcttctt    1320
taaaggcaaa tgggagagac cctttgaagt caaggacacc gaggaagagg acttccacgt    1380
ggaccaggtg accaccgtga aggtgcctat gatgaagcgt ttaggcatgt ttaacatcca    1440
gcactgtaag aagctgtcca gctgggtgct gctgatgaaa tacctgggca atgccaccgc    1500
catcttcttc ctgcctgatg aggggaaact acagcacctg gaaaatgaac tcacccacga    1560
tatcatcacc aagttcctgg aaaatgaaga cagaaggtct gccagcttac atttacccaa    1620
actgtccatt actggaacct atgatctgaa gagcgtcctg ggtcaactgg gcatcactaa    1680
ggtcttcagc aatggggctg acctctccgg ggtcacagag gaggcacccc tgaagctctc    1740
```

-continued

```
caaggccgtg cataaggctg tgctgaccat cgacgagaaa gggactgaag ctgctgggc      1800 catgttttta gaggccatac ccatgtctat cccccccgag gtcaagttca acaaacccttt    1860 tgtcttctta atgattgaac aaaataccaa gtctcccctc ttcatgggaa aagtggtgaa     1920
tcccacccaa aaataactgc ctctcgctcc tcaacccctc ccctccatcc ctggcccct      1980 ccctggatga cattaaagaa gggggtaccg caagggcgaa ttctgcagat atccatcaca     2040
ctggcggccg cgactctagc tagaggatct ttgtgaagga accttacttc tgtggtgtga     2100
cataattgga caaactacct acagagattt aaagctctaa ggtaaatata aaattttaa      2160 gtgtataatg tgttaaacta ctgattctaa ttgtttgtgt attttagatt ccaacctatg     2220
gaactgatga atgggagcag tggtggaatg cctttaatga ggaaaacctg ttttgctcag     2280
aagaaatgcc atctagtgat gatgaggcta ctgctgactc tcaacattct actcctccaa     2340
aaaagaagag aaaggtagaa gaccccaagg actttccttc agaattgcta agttttttga     2400
gtcatgctgt gtttagtaat agaactcttg cttgctttgc tatttacacc acaaaggaaa     2460
aagctgcact gctatacaag aaaattatgg aaaaatattc tgtaacctttt ataagtaggc    2520 ataacagtta taatcataac atactgtttt ttcttactcc acacaggcat agagtgtctg     2580
ctattaataa ctatgctcaa aaattgtgta cctttagctt tttaatttgt aaaggggtta    2640
ataaggaata tttgatgtat agtgccttga ctagagatca taatcagcca taccacattt    2700
gtagaggttt tacttgcttt aaaaaacctc ccacacctcc ccctgaacct gaaacataaa    2760
atgaatgcaa ttgttgttgt taacttgttt attgcagctt ataatggtta caaataaagc    2820
aatagcatca caaatttcac aaataaagca ttttttttcac tgcattctag ttgtggtttg    2880
tccaaactca tcaatgtatc ttatcatgtc tggatccccg ggtaccgctc tagagcgaat    2940
taattcactg gccgtcgttt tacaacgtcg tgactgggaa aaccctggcg ttacccaact    3000
taatcgcctt gcagcacatc cccctttcgc cagctggcgt aatagcgaag aggcccgcac    3060
cgatcgccct tcccaacagt tgcgcagcct gaatggcgaa tggcgcctga tgcggtattt    3120
tctccttacg catctgtgcg gtatttcaca ccgcatatgg tgcactctca gtacaatctg    3180
ctctgatgcc gcatagttaa gccagccccg acacccgcca cacccgctg acgcgccctg     3240 acgggcttgt ctgctcccgg catccgctta cagacaagct gtgaccgtct ccgggagctg    3300
catgtgtcag aggttttcac cgtcatcacc gaaacgcgcg agacgaaagg gcctcgtgat    3360
acgcctattt ttataggtta atgtcatgat aataatggtt tcttagacgt caggtggcac    3420
ttttcgggga atgtgcgcg gaaccccctat ttgtttattt ttctaaatac attcaaatat    3480
gtatccgctc atgagacaat aaccctgata aatgcttcaa taatattgaa aaaggaagag    3540
tatgagtatt caacatttcc gtgtcgccct tattcccttt tttgcggcat tttgccttcc    3600 tgttttgct cacccagaaa cgctggtgaa agtaaaagat gctgaagatc agttgggtgc     3660
acgagtgggt tacatcgaac tggatctcaa cagcggtaag atccttgaga gttttcgccc    3720
cgaagaacgt tttccaatga tgagcacttt taaagttctg ctatgtggcg cggtattatc    3780
ccgtattgac gccgggcaag agcaactcgg tcgccgcata cactattctc agaatgactt    3840
ggttgagtac tcaccagtca cagaaaagca tcttacggat ggcatgacag taagagaatt    3900
atgcagtgct gccataacca tgagtgataa cactgcggcc aacttacttc tgacaacgat    3960
cggaggaccg aaggagctaa ccgcttttttt gcacaacatg ggggatcatg taactcgcct    4020
tgatcgttgg gaaccggagc tgaatgaagc cataccaaac gacgagcgtg acaccacgat    4080
gcctgtagca atggcaacaa cgttgcgcaa actattaact ggcgaactac ttactctagc    4140
```

-continued

```
ttcccggcaa caattaatag actggatgga ggcggataaa gttgcaggac cacttctgcg    4200
ctcggccctt ccggctggct ggtttattgc tgataaatct ggagccggtg agcgtgggtc    4260
tcgcggtatc attgcagcac tggggccaga tggtaagccc tcccgtatcg tagttatcta    4320
cacgacgggg agtcaggcaa ctatggatga acgaaataga cagatcgctg agataggtgc    4380
ctcactgatt aagcattggt aactgtcaga ccaagtttac tcatatatac tttagattga    4440
tttaaaactt catttttaat ttaaaaggat ctaggtgaag atcctttttg ataatctcat    4500
gaccaaaatc ccttaacgtg agttttcgtt ccactgagcg tcagacccccg tagaaaagat    4560
caaaggatct tcttgagatc ctttttttct gcgcgtaatc tgctgcttgc aaacaaaaaa    4620
accaccgcta ccagcggtgg tttgtttgcc ggatcaagag ctaccaactc tttttccgaa    4680
ggtaactggc ttcagcagag cgcagatacc aaatactgtc cttctagtgt agccgtagtt    4740
aggccaccac ttcaagaact ctgtagcacc gcctacatac ctcgctctgc taatcctgtt    4800
accagtggct gctgccagtg gcgataagtc gtgtcttacc gggttggact caagacgata    4860
gttaccggat aaggcgcagc ggtcgggctg aacggggggt tcgtgcacac agcccagctt    4920
ggagcgaacg acctacaccg aactgagata cctacagcgt gagctatgag aaagcgccac    4980
gcttcccgaa gggagaaagg cggacaggta tccggtaagc ggcagggtcg aacaggaga    5040
gcgcacgagg gagcttccag ggggaaacgc ctggtatctt tatagtcctg tcgggtttcg    5100
ccacctctga cttgagcgtc gatttttgtg atgctcgtca gggggggcgga gcctatggaa    5160
aaacgccagc aacgcggcct ttttacggtt cctggccttt tgctggcctt ttgctcacat    5220
gttctttcct gcgttatccc ctgattctgt ggataaccgt attaccgcct ttgagtgagc    5280
tgataccgct cgccgcagcc gaacgaccga gcgcagcgag tcagtgagcg aggaagcgga    5340
agagcgccca atacgcaaac cgcctctccc cgcgcgttgg ccgattcatt aatgcagctg    5400
gcacgacagg tttcccgact ggaaagcggg cagtgagcgc aacgcaatta atgtgagtta    5460
gctcactcat taggcacccc aggctttaca ctttatgctt ccggctcgta tgttgtgtgg    5520
aattgtgagc ggataacaat ttcacacagg aaacagctat gaccatgatt acgccaagct    5580
ctctagagag cttgcatgcc tgcaggtcga                                     5610
```

<210> SEQ ID NO 7
<211> LENGTH: 10705
<212> TYPE: DNA
<213> ORGANISM: Artificial Sequence
<220> FEATURE:
<223> OTHER INFORMATION: vector pFGF8-hyg-s

<400> SEQUENCE: 7

```
cgcgttgaca ttgattattg actagttatt aatagtaatc aattacgggg tcattagttc      60
atagcccata tatggagttc cgcgttacat aacttacggt aaatggcccg cctggctgac     120
cgcccaacga cccccgccca ttgacgtcaa taatgacgta tgttcccata gtaacgccaa     180
tagggacttt ccattgacgt caatgggtgg agtatttacg gtaaactgcc cacttggcag     240
tacatcaagt gtatcatatg ccaagtacgc cccctattga cgtcaatgac ggtaaatggc     300
ccgcctggca ttatgcccag tacatgacct tatgggactt tcctacttgg cagtacatct     360
acgtattagt catcgctatt accatggtga tgcggttttg gcagtacatc aatgggcgtg     420
gatagcggtt tgactcacgg ggatttccaa gtctccaccc cattgacgtc aatgggagtt     480
tgttttggca ccaaaatcaa cgggactttc caaaatgtcg taacaactcc gccccattga     540
```

```
cgcaaatggg cggtaggcgt gtacggtggg aggtctatat aagcagagct ctctggctaa    600
ctagagaacc cactgcttac tggcttatcg aaattaatac gactcactat agggagaccc    660
aagcttgacc tcgagatgca aatagagctc tccacctgct tctttctgtg ccttttgcga    720
ttctgcttta gtgccaccag aagatactac ctgggtgcag tggaactgtc atgggactat    780
atgcaaagtg atctcggtga gctgcctgtg gacgcaagat ttcctcctag agtgccaaaa    840
tcttttccat tcaacacctc agtcgtgtac aaaaagactc tgtttgtaga attcacggat    900
cacctttcca acatcgctaa gccaaggcca ccctggatgg gtctgctagg tcctaccatc    960
caggctgagg tttatgatac agtggtcatt acacttaaga acatggcttc ccatcctgtc   1020
agtcttcatg ctgttggtgt atcctactgg aaagcttctg agggagctga atatgatgat   1080
cagaccagtc aaagggagaa agaagatgat aaagtcttcc ctggtggaag ccatacatat   1140
gtctggcagg tcctgaaaga gaatggtcca atggcctctg acccactgtg ccttacctac   1200
tcatatcttt ctcatgtgga cctggtaaaa gacttgaatt caggcctcat tggagcccta   1260
ctagtatgta gagaagggag tctggccaag gaaaagacac agaccttgca caaatttata   1320
ctacttttg ctgtatttga tgaagggaaa gttggcact cagaaacaaa gaactccttg     1380
atgcaggata gggatgctgc atctgctcgg gcctggccta aaatgcacac agtcaatggt   1440
tatgtaaaca ggtctctgcc aggtctgatt ggatgccaca ggaaatcagt ctattggcat   1500
gtgattgaa tgggcaccac tcctgaagtg cactcaatat tcctcgaagg tcacacattt   1560
cttgtgagga accatcgcca ggcgtccttg gaaatctcgc caataacttt ccttactgct   1620
caaacactct tgatggacct tggacagttt ctactgtttt gtcatatctc ttcccaccaa   1680
catgatggca tggaagctta tgtcaaagta gacagctgtc cagaggaacc ccaactacga   1740
atgaaaaata tgaagaagc ggaagactat gatgatgatc ttactgattc tgaaatggat    1800
gtggtcaggt ttgatgatga caactctcct tcctttatcc aaattcgctc agttgccaag   1860
aagcatccta aaacttgggt acattacatt gctgctgaag aggaggactg ggactatgct   1920
cccttagtcc tcgccccga tgacagaagt tataaaagtc aatatttgaa caatggccct    1980
cagcggattg gtaggaagta caaaaaagtc cgatttatgg catacacaga tgaaaccttt   2040
aagactcgtg aagctattca gcatgaatca ggaatcttgg gaccttact ttatggggaa    2100
gttggagaca cactgttgat tatatttaag aatcaagcaa gcagaccata taacatctac   2160
cctcacggaa tcactgatgt ccgtcctttg tattcaagga gattaccaaa aggtgtaaaa   2220
catttgaagg atttttccaat tctgccagga gaaatattca aatataaatg gacagtgact   2280
gtagaagatg ggccaactaa atcagatcct cggtgcctga cccgctatta ctctagtttc   2340
gttaatatgg agagagatct agcttcagga ctcattggcc ctctcctcat ctgctacaaa   2400
gaatctgtag atcaaagagg aaaccagata atgtcagaca agaggaatgt catcctgttt   2460
tctgtatttg atgagaaccg aagctggtac ctcacagaga atatacaacg ctttctcccc   2520
aatccagctg gagtgcagct tgaggatcca gagttccaag cctccaacat catgcacagc   2580
atcaatggct atgttttga tagtttgcag ttgtcagttt gtttgcatga ggtggcatac    2640
tggtacattc taagcattgg agcacagact gacttccttt ctgtcttctt ctctggatat   2700
accttcaaac acaaaatggt ctatgaagac acactcaccc tattcccatt ctcaggagaa   2760
actgtcttca gtcgatgga aaacccaggt ctatggattc tggggtgcca caactcagac   2820
tttcggaaca gaggcatgac cgccttactg aaggtttcta gttgtgacaa gaacactggt   2880
gattattacg aggacagtta tgaagatatt tcagcatact tgctgagtaa aaacaatgcc   2940
```

```
attgaaccaa gaagcttctc ccagaattca agacatcaag cttatcgata ccgtcgaggg   3000
gaaataactc gtactactct tcagtcagat caagaggaaa ttgactatga tgataccata   3060
tcagttgaaa tgaagaagga agattttgac atttatgatg aggatgaaaa tcagagcccc   3120
cgcagctttc aaaagaaaac acgacactat tttattgctg cagtggagag gctctgggat   3180
tatgggatga gtagctcccc acatgttcta agaaacaggg ctcagagtgg cagtgtccct   3240
cagttcaaga aagttgtttt ccaggaattt actgatggct cctttactca gcccttatac   3300
cgtggagaac taaatgaaca tttgggactc ctggggccat atataagagc agaagttgaa   3360
gataatatca tggtaacttt cagaaatcag gcctctcgtc cctattcctt ctattctagc   3420
cttatttctt atgaggaaga tcagaggcaa ggagcagaac tagaaaaaa ctttgtcaag   3480 cctaatgaaa ccaaaactta cttttggaaa gtgcaacatc atatggcacc cactaaagat   3540
gagtttgact gcaaagcctg ggcttatttc tctgatgttg acctggaaaa agatgtgcac   3600
tcaggcctga ttggacccct tctggtctgc cacactaaca cactgaaccc tgctcatggg   3660
agacaagtga cagtacagga atttgctctg tttttcacca tctttgatga gaccaaaagc   3720
tggtacttca ctgaaaatat ggaaagaaac tgcagggctc cctgcaatat ccagatggaa   3780
gatcccactt ttaaagagaa ttatcgcttc catgcaatca atggctacat aatggataca   3840
ctacctggct tagtaatggc tcaggatcaa aggattcgat ggtatctgct cagcatgggc   3900
agcaatgaaa acatccattc tattcatttc agtggacatg tgttcactgt acgaaaaaaa   3960
gaggagtata aaatggcact gtacaatctc tatccaggtg tttttgagac agtggaaatg   4020
ttaccatcca agctggaat ttggcgggtg gaatgcctta ttggcgagca tctacatgct   4080
gggatgagca cacttttctct ggtgtacagc aataagtgtc agactcccct gggaatggct   4140
tctggacaca ttagagattt tcagattaca gcttcaggac aatatggaca gtgggcccca   4200
aagctggcca gacttcatta ttccggatca atcaatgcct ggagcaccaa ggagcccttt   4260
tcttggatca aggtggatct gttggcacca atgattattc acggcatcaa gacccagggt   4320
gcccgtcaga agttctccag cctctacatc tctcagttta tcatcatgta tagtcttgat   4380
gggaagaagt ggcagactta tcgaggaaat tccactggaa ccttaatggt cttctttggc   4440
aatgtggatt catctgggat aaaaacacaat atttttaacc ctccaattat tgctcgatac   4500
atccgtttgc acccaactca ttatagcatt cgcagcactc ttcgcatgga gttgatgggc   4560
tgtgatttaa atagttgcag catgccattg ggaatggaga gtaaagcaat atcagatgca   4620
cagattactg cttcatccta cttaccaat atgtttgcca cctggtctcc ttcaaaagct   4680
cgacttcacc tccaagggag gagtaatgcc tggagacctc aggtgaataa tccaaaagag   4740
tggctgcaag tggacttcca gaagacaatg aaagtcacag gagtaactac tcagggagta   4800
aaatctctgc ttaccagcat gtatgtgaag gagttcctca tctccagcag tcaagatggc   4860
catcagtgga ccctcttttt tcagaatggc aaagtaaagg tttttcaggg aaatcaagac   4920
tccttcacac ctgtggtgaa ctctctagac ccaccgttac tgactcgcta ccttcgaatt   4980
cacccccaga gttgggtgca ccagattgcc ctgaggatgg aggttctggg ctgcgaggca   5040
caggacctct actgagcggc cgcgactcta ctagaggatc tttgtgaagg aaccttactt   5100
ctgtggtgtg acataattgg acaaactacc tacagagatt taaagctcta aggtaaatat   5160
aaaattttta agtgtataat gtgttaaact actgattcta attgtttgtg tattttagat   5220
tccaacctat ggaactgatg aatgggagca gtggtggaat gcctttaatg aggaaaacct   5280
```

```
gttttgctca gaagaaatgc catctagtga tgatgaggct actgctgact ctcaacattc      5340
tactcctcca aaaagaaga gaaaggtaga agaccccaag gactttcctt cagaattgct      5400
aagttttttg agtcatgctg tgtttagtaa tagaactctt gcttgctttg ctatttacac      5460
cacaaaggaa aaagctgcac tgctatacaa gaaaattatg gaaaaatatt ctgtaacctt      5520
tataagtagg cataacagtt ataatcataa catactgttt tttcttactc cacacaggca      5580
tagagtgtct gctattaata actatgctca aaaattgtgt accttttagct ttttaatttg      5640 taaaggggtt aataaggaat atttgatgta tagtgccttg actagagatc ataatcagcc      5700
ataccacatt tgtagaggtt ttacttgctt taaaaaacct cccacacctc cccctgaacc      5760
tgaaacataa aatgaatgca attgttgttg ttaacttgtt tattgcagct tataatggtt      5820
acaaataaag caatagcatc acaaatttca caaataaagc attttttttca ctgcattcta      5880 gttgtggttt gtccaaactc atcaatgtat cttatcatgt ctggatcccc cgaacgccag      5940
caagacgtag cccagcgcgt cggccccgag atgcgccgcg tgcggctgct ggagatggcg      6000
gacgcgatgg atatgttctg ccaagggttg gtttgcgcat tcacagttct ccgcaagaat      6060
tgattggctc caattcttgg agtggtgaat ccgttagcga ggtgccgccg ggctgcttca      6120
tccccgtggc ccgttgctcg cgtttgctgg cggtgtcccc ggaagaaata tatttgcatg      6180
tctttagttc tatgatgaca caaaccccgc ccagcgtctt gtcattggcg aattcgaaca      6240
cgcagatgca gtcggggcgg cgcggtccca ggtccacttc gcatattaag gtgacgcgtg      6300
tggcctcgaa caccgagcga ccctgcagcg acccgcttaa cagcgtcaac agcgtgccgc      6360
aagatcagct tgatatgaaa aagcctgaac tcaccgcgac gtctgtcgag aagtttctga      6420
tcgaaaagtt cgacagcgtc tccgacctga tgcagctctc ggagggcgaa gaatctcgtg      6480
ctttcagctt cgatgtagga gggcgtggat atgtcctgcg ggtaaatagc tgcgccgatg      6540
gtttctacaa agatcgttat gtttatcggc actttgcatc ggccgcgctc ccgattccgg      6600
aagtgcttga cattggggaa ttcagcgaga gcctgaccta ttgcatctcc cgccgtgcac      6660
agggtgtcac gttgcaagac ctgcctgaaa ccgaactgcc cgctgttctg cagccggtcg      6720
cggaggccat ggatgcgatc gctgcggccg atcttagcca cacgagcggg ttcggcccat      6780
tcggaccgca aggaatcggt caatacacta catggcgtga tttcatatgc gcgattgctg      6840
atccccatgt gtatcactgg caaactgtga tggacgacac cgtcagtgcg tccgtcgcgc      6900
aggctctcga tgagctgatg ctttgggccg aggactgccc cgaagtccgg cacctcgtgc      6960
acgcggattt cggctccaac aatgtcctga cggacaatgg ccgcataaca gcggtcattg      7020
actggagcga ggcgatgttc ggggattccc aatacgaggt cgccaacatc ttcttctgga      7080
ggccgtggtt ggcttgtatg gagcagcaga cgcgctactt cgagcggagg catccggagc      7140
ttgcaggatc gccgcggctc cgggcgtata tgctccgcat tggtcttgac caactctatc      7200
agagcttggt tgacggcaat ttcgatgatg cagcttgggc gcagggtcga tgcgacgcaa      7260
tcgtccgatc cggagccggg actgtcgggc gtacacaaat cgcccgcaga agcgcggccg      7320
tctggaccga tggctgtgta gaagtactcg ccgatagtgg aaaccgacgc cccagcactc      7380
gtggggatcg ggagatgggg gaggctaact gaaacacgga aggagacaat accggaagga      7440
acccgcgcta tgacggcaat aaaaagacag aataaaacgc acgggtgttg ggtcgtttgt      7500
tcataaacgc ggggttcggt cccagggctg gcactctgtc gataccccac cgagacccca      7560
ttggggccaa tacgcccgcg tttcttcctt ttccccaccc caaccccaa gttcgggtga      7620 aggcccaggg ctcgcagcca acgtcgggc ggcaagcccg ccatagccac gggccccgtg      7680
```

```
ggttagggac ggggtccccc atggggaatg gtttatggtt cgtggggtt attcttttgg      7740 gcgttgcgtg gggtcaggtc cacgactgga ctgagcagac agacccatgg tttttggatg      7800
gcctgggcat ggaccgcatg tactggcgcg acacgaacac cgggcgtctg tggctgccaa      7860
acacccccga cccccaaaaa ccaccgcgcg gattctggc gccagtgcca agctgggtac       7920
cctctagagc gaattaattc actggccgtc gttttacaac gtcgtgactg ggaaaaccct      7980
ggcgttaccc aacttaatcg ccttgcagca catccccctt tcgccagctg gcataatagc      8040
gaagaggccc gcaccgatcg cccttcccaa cagttgcgca gcctgaatgg cgaatggcgc      8100
ctgatgcggt attttctcct tacgcatctg tgcggtattt cacaccgcat atggtgcact      8160
ctcagtacaa tctgctctga tgccgcatag ttaagccagc cccgacaccc gccaacaccc      8220
gctgacgcgc cctgacgggc ttgtctgctc ccggcatccg cttacagaca agctgtgacc      8280
gtctccggga gctgcatgtg tcagaggttt tcaccgtcat caccgaaacg cgcgagacga      8340 aaggggggt accagcttcg tagctagaac atcatgttct gggatatcag cttcgtagct      8400
agaacatcat gttctggtac ccccctcgtg atacgcctat ttttataggt taatgtcatg      8460
ataataatgg tttcttagac gtcaggtggc acttttcggg gaaatgtgcg cggaacccct      8520
atttgtttat ttttctaaat acattcaaat atgtatccgc tcatgagaca taaccctga      8580 taaatgcttc aataatattg aaaaaggaag agtatgagta ttcaacattt ccgtgtcgcc      8640
cttattccct tttttgcggc attttgcctt cctgttttg ctcacccaga aacgctggtg       8700
aaagtaaaag atgctgaaga tcagttgggt gcacgagtgg gttacatcga actggatctc      8760
aacagcggta agatccttga gagttttcgc cccgaagaac gttttccaat gatgagcact      8820
tttaaagttc tgctatgtgg cgcggtatta tcccgtattg acgccgggca agagcaactc      8880
ggtcgccgca tacactattc tcagaatgac ttggttgagt actcaccagt cacagaaaag      8940
catcttacgg atggcatgac agtaagagaa ttatgcagtg ctgccataac catgagtgat      9000
aacactgcgg ccaacttact tctgacaacg atcggaggac cgaaggagct aaccgctttt      9060
ttgcacaaca tgggggatca tgtaactcgc cttgatcgtt gggaaccgga gctgaatgaa      9120
gccataccaa acgacgagcg tgacaccacg atgcctgtag caatggcaac aacgttgcgc      9180
aaactattaa ctggcgaact acttactcta gcttcccggc aacaattaat agactggatg      9240
gaggcggata aagttgcagg accacttctg cgctcggccc ttccggctgg ctggtttatt      9300
gctgataaat ctggagccgg tgagcgtggg tctcgcggta tcattgcagc actggggcca      9360
gatggtaagc cctcccgtat cgtagttatc tacacgacgg ggagtcaggc aactatggat      9420
gaacgaaata gacagatcgc tgagataggt gcctcactga ttaagcattg gtaactgtca      9480
gaccaagttt actcatatat actttagatt gatttaaaac ttcattttta atttaaaagg      9540
atctaggtga agatcctttt tgataatctc atgaccaaaa tcccttaacg tgagttttcg      9600
ttccactgag cgtcagaccc cgtagaaaag atcaaaggat cttcttgaga tccttttttt      9660
ctgcgcgtaa tctgctgctt gcaaacaaaa aaaccaccgc taccagcggt ggtttgtttg      9720
ccggatcaag agctaccaac tcttttttccg aaggtaactg gcttcagcag agcgcagata      9780
ccaaatactg ttcttctagt gtagccgtag ttaggccacc acttcaagaa ctctgtagca      9840
ccgcctacat acctcgctct gctaatcctg ttaccagtgg ctgctgccag tggcgataag      9900
tcgtgtctta ccgggttgga ctcaagacga tagttaccgg ataaggcgca gcggtcgggc      9960
tgaacggggg gttcgtgcac acagcccagc ttggagcgaa cgacctacac cgaactgaga     10020
```

```
tacctacagc gtgagctatg agaaagcgcc acgcttcccg aagggagaaa ggcggacagg    10080
tatccggtaa gcggcagggt cggaacagga gagcgcacga gggagcttcc agggggaaac    10140
gcctggtatc tttatagtcc tgtcgggttt cgccacctct gacttgagcg tcgatttttg    10200
tgatgctcgt caggggggcg gagcctatgg aaaaacgcca gcaacgcggc cttttttacgg   10260 ttcctggcct tttgctggcc ttttgctcac atgttctttc ctgcgttatc ccctgattct    10320
gtggataacc gtattaccgc ctttgagtga gctgataccg ctcgccgcag ccgaacgacc    10380
gagcgcagcg agtcagtgag cgaggaagcg gaagagcgcc caatacgcaa accgcctctc    10440
cccgcgcgtt ggccgattca ttaatgcagc tggcacgaca ggtttcccga ctggaaagcg    10500
ggcagtgagc gcaacgcaat taatgtgagt tagctcactc attaggcacc ccaggcttta    10560
cactttatgc ttccggctcg tatgttgtgt ggaattgtga gcggataaca atttcacaca    10620
ggaaacagct atgaccatga ttacgccaag ctctctagag ctctagagct ctagagctct    10680
agagagcttg catgcctgca ggtcg                                         10705

<210> SEQ ID NO 8
<211> LENGTH: 6996
<212> TYPE: DNA
<213> ORGANISM: Homo sapiens
<220> FEATURE:
<221> NAME/KEY: CDS
<222> LOCATION: (1)..(6996)

<400> SEQUENCE: 8 gcc acc aga aga tac tac ctg ggt gca gtg gaa ctg tca tgg gac tat    48
Ala Thr Arg Arg Tyr Tyr Leu Gly Ala Val Glu Leu Ser Trp Asp Tyr
1               5                  10                  15 atg caa agt gat ctc ggt gag ctg cct gtg gac gca aga ttt cct cct    96
Met Gln Ser Asp Leu Gly Glu Leu Pro Val Asp Ala Arg Phe Pro Pro
            20                  25                  30 aga gtg cca aaa tct ttt cca ttc aac acc tca gtc gtg tac aaa aag   144
Arg Val Pro Lys Ser Phe Pro Phe Asn Thr Ser Val Val Tyr Lys Lys
        35                  40                  45 act ctg ttt gta gaa ttc acg gtt cac ctt ttc aac atc gct aag cca   192
Thr Leu Phe Val Glu Phe Thr Val His Leu Phe Asn Ile Ala Lys Pro
    50                  55                  60 agg cca ccc tgg atg ggt ctg cta ggt cct acc atc cag gct gag gtt   240
Arg Pro Pro Trp Met Gly Leu Leu Gly Pro Thr Ile Gln Ala Glu Val
65                  70                  75                  80 tat gat aca gtg gtc att aca ctt aag aac atg gct tcc cat cct gtc   288
Tyr Asp Thr Val Val Ile Thr Leu Lys Asn Met Ala Ser His Pro Val
                85                  90                  95 agt ctt cat gct gtt ggt gta tcc tac tgg aaa gct tct gag gga gct   336
Ser Leu His Ala Val Gly Val Ser Tyr Trp Lys Ala Ser Glu Gly Ala
            100                 105                 110 gaa tat gat gat cag acc agt caa agg gag aaa gaa gat gat aaa gtc   384
Glu Tyr Asp Asp Gln Thr Ser Gln Arg Glu Lys Glu Asp Asp Lys Val
        115                 120                 125 ttc cct ggt gga agc cat aca tat gtc tgg cag gtc ctg aaa gag aat   432
Phe Pro Gly Gly Ser His Thr Tyr Val Trp Gln Val Leu Lys Glu Asn
    130                 135                 140 ggt cca atg gcc tct gac cca ctg tgc ctt acc tac tca tat ctt tct   480
Gly Pro Met Ala Ser Asp Pro Leu Cys Leu Thr Tyr Ser Tyr Leu Ser
145                 150                 155                 160 cat gtg gac ctg gta aaa gac ttg aat tca ggc ctc att gga gcc cta   528
His Val Asp Leu Val Lys Asp Leu Asn Ser Gly Leu Ile Gly Ala Leu
                165                 170                 175
```

-continued

| | | |
|---|---|---|
| cta gta tgt aga gaa ggg agt ctg gcc aag gaa aag aca cag acc ttg<br>Leu Val Cys Arg Glu Gly Ser Leu Ala Lys Glu Lys Thr Gln Thr Leu<br>            180                   185                  190 | 576 |
| cac aaa ttt ata cta ctt ttt gct gta ttt gat gaa ggg aaa agt tgg<br>His Lys Phe Ile Leu Leu Phe Ala Val Phe Asp Glu Gly Lys Ser Trp<br>        195                   200                   205 | 624 |
| cac tca gaa aca aag aac tcc ttg atg cag gat agg gat gct gca tct<br>His Ser Glu Thr Lys Asn Ser Leu Met Gln Asp Arg Asp Ala Ala Ser<br>210                   215                   220 | 672 |
| gct cgg gcc tgg cct aaa atg cac aca gtc aat ggt tat gta aac agg<br>Ala Arg Ala Trp Pro Lys Met His Thr Val Asn Gly Tyr Val Asn Arg<br>225                   230                   235                 240 | 720 |
| tct ctg cca ggt ctg att gga tgc cac agg aaa tca gtc tat tgg cat<br>Ser Leu Pro Gly Leu Ile Gly Cys His Arg Lys Ser Val Tyr Trp His<br>                  245                   250                  255 | 768 |
| gtg att gga atg ggc acc act cct gaa gtg cac tca ata ttc ctc gaa<br>Val Ile Gly Met Gly Thr Thr Pro Glu Val His Ser Ile Phe Leu Glu<br>                   260                   265                 270 | 816 |
| ggt cac aca ttt ctt gtg agg aac cat cgc cag gcg tcc ttg gaa atc<br>Gly His Thr Phe Leu Val Arg Asn His Arg Gln Ala Ser Leu Glu Ile<br>               275                   280                   285 | 864 |
| tcg cca ata act ttc ctt act gct caa aca ctc ttg atg gac ctt gga<br>Ser Pro Ile Thr Phe Leu Thr Ala Gln Thr Leu Leu Met Asp Leu Gly<br>290                   295                   300 | 912 |
| cag ttt cta ctg ttt tgt cat atc tct tcc cac caa cat gat ggc atg<br>Gln Phe Leu Leu Phe Cys His Ile Ser Ser His Gln His Asp Gly Met<br>305                   310                   315                 320 | 960 |
| gaa gct tat gtc aaa gta gac agc tgt cca gag gaa ccc caa cta cga<br>Glu Ala Tyr Val Lys Val Asp Ser Cys Pro Glu Glu Pro Gln Leu Arg<br>                   325                   330                 335 | 1008 |
| atg aaa aat aat gaa gaa gcg gaa gac tat gat gat gat ctt act gat<br>Met Lys Asn Asn Glu Glu Ala Glu Asp Tyr Asp Asp Asp Leu Thr Asp<br>        340                   345                   350 | 1056 |
| tct gaa atg gat gtg gtc agg ttt gat gat gac aac tct cct tcc ttt<br>Ser Glu Met Asp Val Val Arg Phe Asp Asp Asp Asn Ser Pro Ser Phe<br>                 355                   360                 365 | 1104 |
| atc caa att cgc tca gtt gcc aag aag cat cct aaa act tgg gta cat<br>Ile Gln Ile Arg Ser Val Ala Lys Lys His Pro Lys Thr Trp Val His<br>370                   375                   380 | 1152 |
| tac att gct gct gaa gag gag gac tgg gac tat gct ccc tta gtc ctc<br>Tyr Ile Ala Ala Glu Glu Glu Asp Trp Asp Tyr Ala Pro Leu Val Leu<br>385                   390                   395                 400 | 1200 |
| gcc ccc gat gac aga agt tat aaa agt caa tat ttg aac aat ggc cct<br>Ala Pro Asp Asp Arg Ser Tyr Lys Ser Gln Tyr Leu Asn Asn Gly Pro<br>                   405                   410                 415 | 1248 |
| cag cgg att ggt agg aag tac aaa aaa gtc cga ttt atg gca tac aca<br>Gln Arg Ile Gly Arg Lys Tyr Lys Lys Val Arg Phe Met Ala Tyr Thr<br>        420                   425                   430 | 1296 |
| gat gaa acc ttt aag act cgt gaa gct att cag cat gaa tca gga atc<br>Asp Glu Thr Phe Lys Thr Arg Glu Ala Ile Gln His Glu Ser Gly Ile<br>               435                   440                 445 | 1344 |
| ttg gga cct tta ctt tat ggg gaa gtt gga gac aca ctg ttg att ata<br>Leu Gly Pro Leu Leu Tyr Gly Glu Val Gly Asp Thr Leu Leu Ile Ile<br>450                 455                   460 | 1392 |
| ttt aag aat caa gca agc aga cca tat aac atc tac cct cac gga atc<br>Phe Lys Asn Gln Ala Ser Arg Pro Tyr Asn Ile Tyr Pro His Gly Ile<br>465                   470                   475                 480 | 1440 |
| act gat gtc cgt cct ttg tat tca agg aga tta cca aaa ggt gta aaa<br>Thr Asp Val Arg Pro Leu Tyr Ser Arg Arg Leu Pro Lys Gly Val Lys<br>                   485                   490                 495 | 1488 |

```
cat ttg aag gat ttt cca att ctg cca gga gaa ata ttc aaa tat aaa    1536
His Leu Lys Asp Phe Pro Ile Leu Pro Gly Glu Ile Phe Lys Tyr Lys
            500                 505                 510 tgg aca gtg act gta gaa gat ggg cca act aaa tca gat cct cgg tgc    1584
Trp Thr Val Thr Val Glu Asp Gly Pro Thr Lys Ser Asp Pro Arg Cys
        515                 520                 525 ctg acc cgc tat tac tct agt ttc gtt aat atg gag aga gat cta gct    1632
Leu Thr Arg Tyr Tyr Ser Ser Phe Val Asn Met Glu Arg Asp Leu Ala
    530                 535                 540 tca gga ctc att ggc cct ctc ctc atc tgc tac aaa gaa tct gta gat    1680
Ser Gly Leu Ile Gly Pro Leu Leu Ile Cys Tyr Lys Glu Ser Val Asp
545                 550                 555                 560 caa aga gga aac cag ata atg tca gac aag agg aat gtc atc ctg ttt    1728
Gln Arg Gly Asn Gln Ile Met Ser Asp Lys Arg Asn Val Ile Leu Phe
                565                 570                 575 tct gta ttt gat gag aac cga agc tgg tac ctc aca gag aat ata caa    1776
Ser Val Phe Asp Glu Asn Arg Ser Trp Tyr Leu Thr Glu Asn Ile Gln
            580                 585                 590 cgc ttt ctc ccc aat cca gct gga gtg cag ctt gag gat cca gag ttc    1824
Arg Phe Leu Pro Asn Pro Ala Gly Val Gln Leu Glu Asp Pro Glu Phe
        595                 600                 605 caa gcc tcc aac atc atg cac agc atc aat ggc tat gtt ttt gat agt    1872
Gln Ala Ser Asn Ile Met His Ser Ile Asn Gly Tyr Val Phe Asp Ser
    610                 615                 620 ttg cag ttg tca gtt tgt ttg cat gag gtg gca tac tgg tac att cta    1920
Leu Gln Leu Ser Val Cys Leu His Glu Val Ala Tyr Trp Tyr Ile Leu
625                 630                 635                 640 agc att gga gca cag act gac ttc ctt tct gtc ttc ttc tct gga tat    1968
Ser Ile Gly Ala Gln Thr Asp Phe Leu Ser Val Phe Phe Ser Gly Tyr
                645                 650                 655 acc ttc aaa cac aaa atg gtc tat gaa gac aca ctc acc cta ttc cca    2016
Thr Phe Lys His Lys Met Val Tyr Glu Asp Thr Leu Thr Leu Phe Pro
            660                 665                 670 ttc tca gga gaa act gtc ttc atg tcg atg gaa aac cca ggt cta tgg    2064
Phe Ser Gly Glu Thr Val Phe Met Ser Met Glu Asn Pro Gly Leu Trp
        675                 680                 685 att ctg ggg tgc cac aac tca gac ttt cgg aac aga ggc atg acc gcc    2112
Ile Leu Gly Cys His Asn Ser Asp Phe Arg Asn Arg Gly Met Thr Ala
    690                 695                 700 tta ctg aag gtt tct agt tgt gac aag aac act ggt gat tat tac gag    2160
Leu Leu Lys Val Ser Ser Cys Asp Lys Asn Thr Gly Asp Tyr Tyr Glu
705                 710                 715                 720 gac agt tat gaa gat att tca gca tac ttg ctg agt aaa aac aat gcc    2208
Asp Ser Tyr Glu Asp Ile Ser Ala Tyr Leu Leu Ser Lys Asn Asn Ala
                725                 730                 735 att gaa cca aga agc ttc tcc cag aat tca aga cac cct agc act agg    2256
Ile Glu Pro Arg Ser Phe Ser Gln Asn Ser Arg His Pro Ser Thr Arg
            740                 745                 750 caa aag caa ttt aat gcc acc aca att cca gaa aat gac ata gag aag    2304
Gln Lys Gln Phe Asn Ala Thr Thr Ile Pro Glu Asn Asp Ile Glu Lys
        755                 760                 765 act gac cct tgg ttt gca cac aga aca cct atg cct aaa ata caa aat    2352
Thr Asp Pro Trp Phe Ala His Arg Thr Pro Met Pro Lys Ile Gln Asn
    770                 775                 780 gtc tcc tct agt gat ttg ttg atg ctc ttg cga cag agt cct act cca    2400
Val Ser Ser Ser Asp Leu Leu Met Leu Leu Arg Gln Ser Pro Thr Pro
785                 790                 795                 800 cat ggg cta tcc tta tct gat ctc caa gaa gcc aaa tat gag act ttt    2448
His Gly Leu Ser Leu Ser Asp Leu Gln Glu Ala Lys Tyr Glu Thr Phe
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     | 805 |     |     |     | 810 |     |     |     | 815 |     |     |     |     |
| tct | gat | gat | cca | tca | cct | gga | gca | ata | gac | agt | aat | aac | agc | ctg | tct | 2496 |
| Ser | Asp | Asp | Pro | Ser | Pro | Gly | Ala | Ile | Asp | Ser | Asn | Asn | Ser | Leu | Ser |     |
|     |     |     | 820 |     |     |     | 825 |     |     |     | 830 |     |     |     |     |
| gaa | atg | aca | cac | ttc | agg | cca | cag | ctc | cat | cac | agt | ggg | gac | atg | gta | 2544 |
| Glu | Met | Thr | His | Phe | Arg | Pro | Gln | Leu | His | His | Ser | Gly | Asp | Met | Val |     |
|     |     |     |     |     | 835 |     |     |     | 840 |     |     |     | 845 |     |     |     |
| ttt | acc | cct | gag | tca | ggc | ctc | caa | tta | aga | tta | aat | gag | aaa | ctg | ggg | 2592 |
| Phe | Thr | Pro | Glu | Ser | Gly | Leu | Gln | Leu | Arg | Leu | Asn | Glu | Lys | Leu | Gly |     |
|     | 850 |     |     |     |     | 855 |     |     |     |     | 860 |     |     |     |     |     |
| aca | act | gca | gca | aca | gag | ttg | aag | aaa | ctt | gat | ttc | aaa | gtt | tct | agt | 2640 |
| Thr | Thr | Ala | Ala | Thr | Glu | Leu | Lys | Lys | Leu | Asp | Phe | Lys | Val | Ser | Ser |     |
| 865 |     |     |     |     | 870 |     |     |     |     | 875 |     |     |     |     | 880 |     |
| aca | tca | aat | aat | ctg | att | tca | aca | att | cca | tca | gac | aat | ttg | gca | gca | 2688 |
| Thr | Ser | Asn | Asn | Leu | Ile | Ser | Thr | Ile | Pro | Ser | Asp | Asn | Leu | Ala | Ala |     |
|     |     |     |     | 885 |     |     |     |     | 890 |     |     |     |     | 895 |     |     |
| ggt | act | gat | aat | aca | agt | tcc | tta | gga | ccc | cca | agt | atg | cca | gtt | cat | 2736 |
| Gly | Thr | Asp | Asn | Thr | Ser | Ser | Leu | Gly | Pro | Pro | Ser | Met | Pro | Val | His |     |
|     |     |     | 900 |     |     |     |     | 905 |     |     |     |     | 910 |     |     |     |
| tat | gat | agt | caa | tta | gat | acc | act | cta | ttt | ggc | aaa | aag | tca | tct | ccc | 2784 |
| Tyr | Asp | Ser | Gln | Leu | Asp | Thr | Thr | Leu | Phe | Gly | Lys | Lys | Ser | Ser | Pro |     |
|     |     | 915 |     |     |     |     | 920 |     |     |     |     | 925 |     |     |     |     |
| ctt | act | gag | tct | ggt | gga | cct | ctg | agc | ttg | agt | gaa | gaa | aat | aat | gat | 2832 |
| Leu | Thr | Glu | Ser | Gly | Gly | Pro | Leu | Ser | Leu | Ser | Glu | Glu | Asn | Asn | Asp |     |
|     | 930 |     |     |     |     | 935 |     |     |     |     | 940 |     |     |     |     |     |
| tca | aag | ttg | tta | gaa | tca | ggt | tta | atg | aat | agc | caa | gaa | agt | tca | tgg | 2880 |
| Ser | Lys | Leu | Leu | Glu | Ser | Gly | Leu | Met | Asn | Ser | Gln | Glu | Ser | Ser | Trp |     |
| 945 |     |     |     |     | 950 |     |     |     |     | 955 |     |     |     |     | 960 |     |
| gga | aaa | aat | gta | tcg | tca | aca | gag | agt | ggt | agg | tta | ttt | aaa | ggg | aaa | 2928 |
| Gly | Lys | Asn | Val | Ser | Ser | Thr | Glu | Ser | Gly | Arg | Leu | Phe | Lys | Gly | Lys |     |
|     |     |     |     | 965 |     |     |     |     | 970 |     |     |     |     | 975 |     |     |
| aga | gct | cat | gga | cct | gct | ttg | ttg | act | aaa | gat | aat | gcc | tta | ttc | aaa | 2976 |
| Arg | Ala | His | Gly | Pro | Ala | Leu | Leu | Thr | Lys | Asp | Asn | Ala | Leu | Phe | Lys |     |
|     |     |     | 980 |     |     |     |     | 985 |     |     |     |     | 990 |     |     |     |
| gtt | agc | atc | tct | ttg | tta | aag | aca | aac | aaa | act | tcc | aat | aat | tca | gca | 3024 |
| Val | Ser | Ile | Ser | Leu | Leu | Lys | Thr | Asn | Lys | Thr | Ser | Asn | Asn | Ser | Ala |     |
|     |     | 995 |     |     |     |     | 1000 |     |     |     |     | 1005 |     |     |     |     |
| act | aat | aga | aag | act | cac | att | gat | ggc | cca | tca | tta | tta | att | gag |     | 3069 |
| Thr | Asn | Arg | Lys | Thr | His | Ile | Asp | Gly | Pro | Ser | Leu | Leu | Ile | Glu |     |     |
|     | 1010 |     |     |     |     | 1015 |     |     |     |     | 1020 |     |     |     |     |     |
| aat | agt | cca | tca | gtc | tgg | caa | aat | ata | tta | gaa | agt | gac | act | gag |     | 3114 |
| Asn | Ser | Pro | Ser | Val | Trp | Gln | Asn | Ile | Leu | Glu | Ser | Asp | Thr | Glu |     |     |
| 1025 |     |     |     |     | 1030 |     |     |     |     | 1035 |     |     |     |     |     |     |
| ttt | aaa | aaa | gtg | aca | cct | ttg | att | cat | gac | aga | atg | ctt | atg | gac |     | 3159 |
| Phe | Lys | Lys | Val | Thr | Pro | Leu | Ile | His | Asp | Arg | Met | Leu | Met | Asp |     |     |
|     | 1040 |     |     |     |     | 1045 |     |     |     |     | 1050 |     |     |     |     |     |
| aaa | aat | gct | aca | gct | ttg | agg | cta | aat | cat | atg | tca | aat | aaa | act |     | 3204 |
| Lys | Asn | Ala | Thr | Ala | Leu | Arg | Leu | Asn | His | Met | Ser | Asn | Lys | Thr |     |     |
| 1055 |     |     |     |     | 1060 |     |     |     |     | 1065 |     |     |     |     |     |     |
| act | tca | tca | aaa | aac | atg | gaa | atg | gtc | caa | cag | aaa | aaa | gag | ggc |     | 3249 |
| Thr | Ser | Ser | Lys | Asn | Met | Glu | Met | Val | Gln | Gln | Lys | Lys | Glu | Gly |     |     |
|     | 1070 |     |     |     |     | 1075 |     |     |     |     | 1080 |     |     |     |     |     |
| ccc | att | cca | cca | gat | gca | caa | aat | cca | gat | atg | tcg | ttc | ttt | aag |     | 3294 |
| Pro | Ile | Pro | Pro | Asp | Ala | Gln | Asn | Pro | Asp | Met | Ser | Phe | Phe | Lys |     |     |
| 1085 |     |     |     |     | 1090 |     |     |     |     | 1095 |     |     |     |     |     |     |
| atg | cta | ttc | ttg | cca | gaa | tca | gca | agg | tgg | ata | caa | agg | act | cat |     | 3339 |
| Met | Leu | Phe | Leu | Pro | Glu | Ser | Ala | Arg | Trp | Ile | Gln | Arg | Thr | His |     |     |
|     | 1100 |     |     |     |     | 1105 |     |     |     |     | 1110 |     |     |     |     |     |
| gga | aag | aac | tct | ctg | aac | tct | ggg | caa | ggc | ccc | agt | cca | aag | caa |     | 3384 |

```
          Gly Lys Asn Ser Leu Asn Ser     Gly Gln Gly Pro Ser     Pro Lys Gln
              1115                1120                1125 tta gta tcc tta gga cca gaa aaa tct gtg gaa ggt cag aat ttc        3429
Leu Val Ser Leu Gly Pro Glu Lys Ser Val Glu Gly Gln Asn Phe
    1130                1135                1140 ttg tct gag aaa aac aaa gtg gta gta gga aag ggt gaa ttt aca        3474
Leu Ser Glu Lys Asn Lys Val Val Val Gly Lys Gly Glu Phe Thr
    1145                1150                1155 aag gac gta gga ctc aaa gag atg gtt ttt cca agc agc aga aac        3519
Lys Asp Val Gly Leu Lys Glu Met Val Phe Pro Ser Ser Arg Asn
    1160                1165                1170 cta ttt ctt act aac ttg gat aat tta cat gaa aat aat aca cac        3564
Leu Phe Leu Thr Asn Leu Asp Asn Leu His Glu Asn Asn Thr His
    1175                1180                1185 aat caa gaa aaa aaa att cag gaa gaa ata gaa aag aag gaa aca        3609
Asn Gln Glu Lys Lys Ile Gln Glu Glu Ile Glu Lys Lys Glu Thr
    1190                1195                1200 tta atc caa gag aat gta gtt ttg cct cag ata cat aca gtg act        3654
Leu Ile Gln Glu Asn Val Val Leu Pro Gln Ile His Thr Val Thr
    1205                1210                1215 ggc act aag aat ttc atg aag aac ctt ttc tta ctg agc act agg        3699
Gly Thr Lys Asn Phe Met Lys Asn Leu Phe Leu Leu Ser Thr Arg
    1220                1225                1230 caa aat gta gaa ggt tca tat gag ggg gca tat gct cca gta ctt        3744
Gln Asn Val Glu Gly Ser Tyr Glu Gly Ala Tyr Ala Pro Val Leu
    1235                1240                1245 caa gat ttt agg tca tta aat gat tca aca aat aga aca aag aaa        3789
Gln Asp Phe Arg Ser Leu Asn Asp Ser Thr Asn Arg Thr Lys Lys
    1250                1255                1260 cac aca gct cat ttc tca aaa aaa ggg gag gaa gaa aac ttg gaa        3834
His Thr Ala His Phe Ser Lys Lys Gly Glu Glu Glu Asn Leu Glu
    1265                1270                1275 ggc ttg gga aat caa acc aag caa att gta gag aaa tat gca tgc        3879
Gly Leu Gly Asn Gln Thr Lys Gln Ile Val Glu Lys Tyr Ala Cys
    1280                1285                1290 acc aca agg ata tct cct aat aca agc cag cag aat ttt gtc acg        3924
Thr Thr Arg Ile Ser Pro Asn Thr Ser Gln Gln Asn Phe Val Thr
    1295                1300                1305 caa cgt agt aag aga gct ttg aaa caa ttc aga ctc cca cta gaa        3969
Gln Arg Ser Lys Arg Ala Leu Lys Gln Phe Arg Leu Pro Leu Glu
    1310                1315                1320 gaa aca gaa ctt gaa aaa agg ata att gtg gat gac acc tca acc        4014
Glu Thr Glu Leu Glu Lys Arg Ile Ile Val Asp Asp Thr Ser Thr
    1325                1330                1335 cag tgg tcc aaa aac atg aaa cat ttg acc ccg agc acc ctc aca        4059
Gln Trp Ser Lys Asn Met Lys His Leu Thr Pro Ser Thr Leu Thr
    1340                1345                1350 cag ata gac tac aat gag aag gag aaa ggg gcc att act cag tct        4104
Gln Ile Asp Tyr Asn Glu Lys Glu Lys Gly Ala Ile Thr Gln Ser
    1355                1360                1365 ccc tta tca gat tgc ctt acg agg agt cat agc atc cct caa gca        4149
Pro Leu Ser Asp Cys Leu Thr Arg Ser His Ser Ile Pro Gln Ala
    1370                1375                1380 aat aga tct cca tta ccc att gca aag gta tca tca ttt cca tct        4194
Asn Arg Ser Pro Leu Pro Ile Ala Lys Val Ser Ser Phe Pro Ser
    1385                1390                1395 att aga cct ata tat ctg acc agg gtc cta ttc caa gac aac tct        4239
Ile Arg Pro Ile Tyr Leu Thr Arg Val Leu Phe Gln Asp Asn Ser
    1400                1405                1410
```

```
tct cat ctt cca gca gca tct tat aga aag aaa gat tct ggg gtc    4284
Ser His Leu Pro Ala Ala Ser Tyr Arg Lys Lys Asp Ser Gly Val
    1415                1420                1425 caa gaa agc agt cat ttc tta caa gga gcc aaa aaa aat aac ctt    4329
Gln Glu Ser Ser His Phe Leu Gln Gly Ala Lys Lys Asn Asn Leu
    1430                1435                1440 tct tta gcc att cta acc ttg gag atg act ggt gat caa aga gag    4374
Ser Leu Ala Ile Leu Thr Leu Glu Met Thr Gly Asp Gln Arg Glu
    1445                1450                1455 gtt ggc tcc ctg ggg aca agt gcc aca aat tca gtc aca tac aag    4419
Val Gly Ser Leu Gly Thr Ser Ala Thr Asn Ser Val Thr Tyr Lys
    1460                1465                1470 aaa gtt gag aac act gtt ctc ccg aaa cca gac ttg ccc aaa aca    4464
Lys Val Glu Asn Thr Val Leu Pro Lys Pro Asp Leu Pro Lys Thr
    1475                1480                1485 tct ggc aaa gtt gaa ttg ctt cca aaa gtt cac att tat cag aag    4509
Ser Gly Lys Val Glu Leu Leu Pro Lys Val His Ile Tyr Gln Lys
    1490                1495                1500 gac cta ttc cct acg gaa act agc aat ggg tct cct ggc cat ctg    4554
Asp Leu Phe Pro Thr Glu Thr Ser Asn Gly Ser Pro Gly His Leu
    1505                1510                1515 gat ctc gtg gaa ggg agc ctt ctt cag gga aca gag gga gcg att    4599
Asp Leu Val Glu Gly Ser Leu Leu Gln Gly Thr Glu Gly Ala Ile
    1520                1525                1530 aag tgg aat gaa gca aac aga cct gga aaa gtt ccc ttt ctg aga    4644
Lys Trp Asn Glu Ala Asn Arg Pro Gly Lys Val Pro Phe Leu Arg
    1535                1540                1545 gta gca aca gaa agc tct gca aag act ccc tcc aag cta ttg gat    4689
Val Ala Thr Glu Ser Ser Ala Lys Thr Pro Ser Lys Leu Leu Asp
    1550                1555                1560 cct ctt gct tgg gat aac cac tat ggt act cag ata cca aaa gaa    4734
Pro Leu Ala Trp Asp Asn His Tyr Gly Thr Gln Ile Pro Lys Glu
    1565                1570                1575 gag tgg aaa tcc caa gag aag tca cca gaa aaa aca gct ttt aag    4779
Glu Trp Lys Ser Gln Glu Lys Ser Pro Glu Lys Thr Ala Phe Lys
    1580                1585                1590 aaa aag gat acc att ttg tcc ctg aac gct tgt gaa agc aat cat    4824
Lys Lys Asp Thr Ile Leu Ser Leu Asn Ala Cys Glu Ser Asn His
    1595                1600                1605 gca ata gca gca ata aat gag gga caa aat aag ccc gaa ata gaa    4869
Ala Ile Ala Ala Ile Asn Glu Gly Gln Asn Lys Pro Glu Ile Glu
    1610                1615                1620 gtc acc tgg gca aag caa ggt agg act gaa agg ctg tgc tct caa    4914
Val Thr Trp Ala Lys Gln Gly Arg Thr Glu Arg Leu Cys Ser Gln
    1625                1630                1635 aac cca cca gtc ttg aaa cgc cat caa cgg gaa ata act cgt act    4959
Asn Pro Pro Val Leu Lys Arg His Gln Arg Glu Ile Thr Arg Thr
    1640                1645                1650 act ctt cag tca gat caa gag gaa att gac tat gat gat acc ata    5004
Thr Leu Gln Ser Asp Gln Glu Glu Ile Asp Tyr Asp Asp Thr Ile
    1655                1660                1665 tca gtt gaa atg aag aag gaa gat ttt gac att tat gat gag gat    5049
Ser Val Glu Met Lys Lys Glu Asp Phe Asp Ile Tyr Asp Glu Asp
    1670                1675                1680 gaa aat cag agc ccc cgc agc ttt caa aag aaa aca cga cac tat    5094
Glu Asn Gln Ser Pro Arg Ser Phe Gln Lys Lys Thr Arg His Tyr
    1685                1690                1695 ttt att gct gca gtg gag agg ctc tgg gat tat ggg atg agt agc    5139
Phe Ile Ala Ala Val Glu Arg Leu Trp Asp Tyr Gly Met Ser Ser
    1700                1705                1710
```

```
                                                 -continued tcc cca cat gtt cta aga aac agg gct cag agt ggc agt gtc cct         5184
Ser Pro His Val Leu Arg Asn Arg Ala Gln Ser Gly Ser Val Pro
    1715            1720                1725 cag ttc aag aaa gtt gtt ttc cag gaa ttt act gat ggc tcc ttt         5229
Gln Phe Lys Lys Val Val Phe Gln Glu Phe Thr Asp Gly Ser Phe
1730                1735                1740 act cag ccc tta tac cgt gga gaa cta aat gaa cat ttg gga ctc         5274
Thr Gln Pro Leu Tyr Arg Gly Glu Leu Asn Glu His Leu Gly Leu
    1745            1750                1755 ctg ggg cca tat ata aga gca gaa gtt gaa gat aat atc atg gta         5319
Leu Gly Pro Tyr Ile Arg Ala Glu Val Glu Asp Asn Ile Met Val
1760                1765                1770 act ttc aga aat cag gcc tct cgt ccc tat tcc ttc tat tct agc         5364
Thr Phe Arg Asn Gln Ala Ser Arg Pro Tyr Ser Phe Tyr Ser Ser
    1775            1780                1785 ctt att tct tat gag gaa gat cag agg caa gga gca gaa cct aga         5409
Leu Ile Ser Tyr Glu Glu Asp Gln Arg Gln Gly Ala Glu Pro Arg
1790                1795                1800 aaa aac ttt gtc aag cct aat gaa acc aaa act tac ttt tgg aaa         5454
Lys Asn Phe Val Lys Pro Asn Glu Thr Lys Thr Tyr Phe Trp Lys
    1805            1810                1815 gtg caa cat cat atg gca ccc act aaa gat gag ttt gac tgc aaa         5499
Val Gln His His Met Ala Pro Thr Lys Asp Glu Phe Asp Cys Lys
1820                1825                1830 gcc tgg gct tat ttc tct gat gtt gac ctg gaa aaa gat gtg cac         5544
Ala Trp Ala Tyr Phe Ser Asp Val Asp Leu Glu Lys Asp Val His
    1835            1840                1845 tca ggc ctg att gga ccc ctt ctg gtc tgc cac act aac aca ctg         5589
Ser Gly Leu Ile Gly Pro Leu Leu Val Cys His Thr Asn Thr Leu
1850                1855                1860 aac cct gct cat ggg aga caa gtg aca gta cag gaa ttt gct ctg         5634
Asn Pro Ala His Gly Arg Gln Val Thr Val Gln Glu Phe Ala Leu
    1865            1870                1875 ttt ttc acc atc ttt gat gag acc aaa agc tgg tac ttc act gaa         5679
Phe Phe Thr Ile Phe Asp Glu Thr Lys Ser Trp Tyr Phe Thr Glu
1880                1885                1890 aat atg gaa aga aac tgc agg gct ccc tgc aat atc cag atg gaa         5724
Asn Met Glu Arg Asn Cys Arg Ala Pro Cys Asn Ile Gln Met Glu
    1895            1900                1905 gat ccc act ttt aaa gag aat tat cgc ttc cat gca atc aat ggc         5769
Asp Pro Thr Phe Lys Glu Asn Tyr Arg Phe His Ala Ile Asn Gly
1910                1915                1920 tac ata atg gat aca cta cct ggc tta gta atg gct cag gat caa         5814
Tyr Ile Met Asp Thr Leu Pro Gly Leu Val Met Ala Gln Asp Gln
    1925            1930                1935 agg att cga tgg tat ctg ctc agc atg ggc agc aat gaa aac atc         5859
Arg Ile Arg Trp Tyr Leu Leu Ser Met Gly Ser Asn Glu Asn Ile
1940                1945                1950 cat tct att cat ttc agt gga cat gtg ttc act gta cga aaa aaa         5904
His Ser Ile His Phe Ser Gly His Val Phe Thr Val Arg Lys Lys
    1955            1960                1965 gag gag tat aaa atg gca ctg tac aat ctc tat cca ggt gtt ttt         5949
Glu Glu Tyr Lys Met Ala Leu Tyr Asn Leu Tyr Pro Gly Val Phe
1970                1975                1980 gag aca gtg gaa atg tta cca tcc aaa gct gga att tgg cgg gtg         5994
Glu Thr Val Glu Met Leu Pro Ser Lys Ala Gly Ile Trp Arg Val
    1985            1990                1995 gaa tgc ctt att ggc gag cat cta cat gct ggg atg agc aca ctt         6039
Glu Cys Leu Ile Gly Glu His Leu His Ala Gly Met Ser Thr Leu
```

-continued

|  |  |  |  |  |
|---|---|---|---|---|
| ttt ctg gtg tac agc aat aag tgt cag act ccc ctg gga atg gct | | | | 6084 |
| Phe Leu Val Tyr Ser Asn Lys Cys Gln Thr Pro Leu Gly Met Ala | | | | |
| 2015 2020 2025 | | | | |
| tct gga cac att aga gat ttt cag att aca gct tca gga caa tat | | | | 6129 |
| Ser Gly His Ile Arg Asp Phe Gln Ile Thr Ala Ser Gly Gln Tyr | | | | |
| 2030 2035 2040 | | | | |
| gga cag tgg gcc cca aag ctg gcc aga ctt cat tat tcc gga tca | | | | 6174 |
| Gly Gln Trp Ala Pro Lys Leu Ala Arg Leu His Tyr Ser Gly Ser | | | | |
| 2045 2050 2055 | | | | |
| atc aat gcc tgg agc acc aag gag ccc ttt tct tgg atc aag gtg | | | | 6219 |
| Ile Asn Ala Trp Ser Thr Lys Glu Pro Phe Ser Trp Ile Lys Val | | | | |
| 2060 2065 2070 | | | | |
| gat ctg ttg gca cca atg att att cac ggc atc aag acc cag ggt | | | | 6264 |
| Asp Leu Leu Ala Pro Met Ile Ile His Gly Ile Lys Thr Gln Gly | | | | |
| 2075 2080 2085 | | | | |
| gcc cgt cag aag ttc tcc agc ctc tac atc tct cag ttt atc atc | | | | 6309 |
| Ala Arg Gln Lys Phe Ser Ser Leu Tyr Ile Ser Gln Phe Ile Ile | | | | |
| 2090 2095 2100 | | | | |
| atg tat agt ctt gat ggg aag aag tgg cag act tat cga gga aat | | | | 6354 |
| Met Tyr Ser Leu Asp Gly Lys Lys Trp Gln Thr Tyr Arg Gly Asn | | | | |
| 2105 2110 2115 | | | | |
| tcc act gga acc tta atg gtc ttc ttt ggc aat gtg gat tca tct | | | | 6399 |
| Ser Thr Gly Thr Leu Met Val Phe Phe Gly Asn Val Asp Ser Ser | | | | |
| 2120 2125 2130 | | | | |
| ggg ata aaa cac aat att ttt aac cct cca att att gct cga tac | | | | 6444 |
| Gly Ile Lys His Asn Ile Phe Asn Pro Pro Ile Ile Ala Arg Tyr | | | | |
| 2135 2140 2145 | | | | |
| atc cgt ttg cac cca act cat tat agc att cgc agc act ctt cgc | | | | 6489 |
| Ile Arg Leu His Pro Thr His Tyr Ser Ile Arg Ser Thr Leu Arg | | | | |
| 2150 2155 2160 | | | | |
| atg gag ttg atg ggc tgt gat tta aat agt tgc agc atg cca ttg | | | | 6534 |
| Met Glu Leu Met Gly Cys Asp Leu Asn Ser Cys Ser Met Pro Leu | | | | |
| 2165 2170 2175 | | | | |
| gga atg gag agt aaa gca ata tca gat gca cag att act gct tca | | | | 6579 |
| Gly Met Glu Ser Lys Ala Ile Ser Asp Ala Gln Ile Thr Ala Ser | | | | |
| 2180 2185 2190 | | | | |
| tcc tac ttt acc aat atg ttt gcc acc tgg tct cct tca aaa gct | | | | 6624 |
| Ser Tyr Phe Thr Asn Met Phe Ala Thr Trp Ser Pro Ser Lys Ala | | | | |
| 2195 2200 2205 | | | | |
| cga ctt cac ctc caa ggg agg agt aat gcc tgg aga cct cag gtg | | | | 6669 |
| Arg Leu His Leu Gln Gly Arg Ser Asn Ala Trp Arg Pro Gln Val | | | | |
| 2210 2215 2220 | | | | |
| aat aat cca aaa gag tgg ctg caa gtg gac ttc cag aag aca atg | | | | 6714 |
| Asn Asn Pro Lys Glu Trp Leu Gln Val Asp Phe Gln Lys Thr Met | | | | |
| 2225 2230 2235 | | | | |
| aaa gtc aca gga gta act act cag gga gta aaa tct ctg ctt acc | | | | 6759 |
| Lys Val Thr Gly Val Thr Thr Gln Gly Val Lys Ser Leu Leu Thr | | | | |
| 2240 2245 2250 | | | | |
| agc atg tat gtg aag gag ttc ctc atc tcc agc agt caa gat ggc | | | | 6804 |
| Ser Met Tyr Val Lys Glu Phe Leu Ile Ser Ser Ser Gln Asp Gly | | | | |
| 2255 2260 2265 | | | | |
| cat cag tgg act ctc ttt ttt cag aat ggc aaa gta aag gtt ttt | | | | 6849 |
| His Gln Trp Thr Leu Phe Phe Gln Asn Gly Lys Val Lys Val Phe | | | | |
| 2270 2275 2280 | | | | |
| cag gga aat caa gac tcc ttc aca cct gtg gtg aac tct cta gac | | | | 6894 |
| Gln Gly Asn Gln Asp Ser Phe Thr Pro Val Val Asn Ser Leu Asp | | | | |
| 2285 2290 2295 | | | | |
| cca ccg tta ctg act cgc tac ctt cga att cac ccc cag agt tgg | | | | 6939 |

```
Pro Pro Leu Leu Thr Arg Tyr Leu Arg Ile His Pro Gln Ser Trp
    2300                2305                2310 gtg cac cag att gcc ctg agg atg gag gtt ctg ggc tgc gag gca       6984
Val His Gln Ile Ala Leu Arg Met Glu Val Leu Gly Cys Glu Ala
    2315                2320                2325 cag gac ctc tac                                                    6996
Gln Asp Leu Tyr
    2330

<210> SEQ ID NO 9
<211> LENGTH: 2332
<212> TYPE: PRT
<213> ORGANISM: Homo sapiens

<400> SEQUENCE: 9

Ala Thr Arg Arg Tyr Tyr Leu Gly Ala Val Glu Leu Ser Trp Asp Tyr
 1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320
```

-continued

Glu Ala Tyr Val Lys Val Asp Ser Cys Pro Glu Pro Gln Leu Arg
            325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Pro Ser Thr Arg

-continued

```
                740                 745                 750
Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
            805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
            930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
        1010                1015                1020

Asn Ser Pro Ser Val Trp Gln Asn Ile Leu Glu Ser Asp Thr Glu
        1025                1030                1035

Phe Lys Lys Val Thr Pro Leu Ile His Asp Arg Met Leu Met Asp
        1040                1045                1050

Lys Asn Ala Thr Ala Leu Arg Leu Asn His Met Ser Asn Lys Thr
        1055                1060                1065

Thr Ser Ser Lys Asn Met Glu Met Val Gln Gln Lys Lys Glu Gly
        1070                1075                1080

Pro Ile Pro Pro Asp Ala Gln Asn Pro Asp Met Ser Phe Phe Lys
        1085                1090                1095

Met Leu Phe Leu Pro Glu Ser Ala Arg Trp Ile Gln Arg Thr His
        1100                1105                1110

Gly Lys Asn Ser Leu Asn Ser Gly Gln Gly Pro Ser Pro Lys Gln
        1115                1120                1125

Leu Val Ser Leu Gly Pro Glu Lys Ser Val Glu Gly Gln Asn Phe
        1130                1135                1140

Leu Ser Glu Lys Asn Lys Val Val Val Gly Lys Gly Glu Phe Thr
        1145                1150                1155
```

```
Lys Asp Val Gly Leu Lys Glu Met Val Phe Pro Ser Ser Arg Asn
    1160            1165            1170

Leu Phe Leu Thr Asn Leu Asp Asn Leu His Glu Asn Asn Thr His
    1175            1180            1185

Asn Gln Glu Lys Lys Ile Gln Glu Glu Ile Glu Lys Lys Glu Thr
    1190            1195            1200

Leu Ile Gln Glu Asn Val Val Leu Pro Gln Ile His Thr Val Thr
    1205            1210            1215

Gly Thr Lys Asn Phe Met Lys Asn Leu Phe Leu Leu Ser Thr Arg
    1220            1225            1230

Gln Asn Val Glu Gly Ser Tyr Glu Gly Ala Tyr Ala Pro Val Leu
    1235            1240            1245

Gln Asp Phe Arg Ser Leu Asn Asp Ser Thr Asn Arg Thr Lys Lys
    1250            1255            1260

His Thr Ala His Phe Ser Lys Lys Gly Glu Glu Asn Leu Glu
    1265            1270            1275

Gly Leu Gly Asn Gln Thr Lys Gln Ile Val Glu Lys Tyr Ala Cys
    1280            1285            1290

Thr Thr Arg Ile Ser Pro Asn Thr Ser Gln Gln Asn Phe Val Thr
    1295            1300            1305

Gln Arg Ser Lys Arg Ala Leu Lys Gln Phe Arg Leu Pro Leu Glu
    1310            1315            1320

Glu Thr Glu Leu Glu Lys Arg Ile Ile Val Asp Asp Thr Ser Thr
    1325            1330            1335

Gln Trp Ser Lys Asn Met Lys His Leu Thr Pro Ser Thr Leu Thr
    1340            1345            1350

Gln Ile Asp Tyr Asn Glu Lys Glu Lys Gly Ala Ile Thr Gln Ser
    1355            1360            1365

Pro Leu Ser Asp Cys Leu Thr Arg Ser His Ser Ile Pro Gln Ala
    1370            1375            1380

Asn Arg Ser Pro Leu Pro Ile Ala Lys Val Ser Ser Phe Pro Ser
    1385            1390            1395

Ile Arg Pro Ile Tyr Leu Thr Arg Val Leu Phe Gln Asp Asn Ser
    1400            1405            1410

Ser His Leu Pro Ala Ala Ser Tyr Arg Lys Lys Asp Ser Gly Val
    1415            1420            1425

Gln Glu Ser Ser His Phe Leu Gln Gly Ala Lys Lys Asn Asn Leu
    1430            1435            1440

Ser Leu Ala Ile Leu Thr Leu Glu Met Thr Gly Asp Gln Arg Glu
    1445            1450            1455

Val Gly Ser Leu Gly Thr Ser Ala Thr Asn Ser Val Thr Tyr Lys
    1460            1465            1470

Lys Val Glu Asn Thr Val Leu Pro Lys Pro Asp Leu Pro Lys Thr
    1475            1480            1485

Ser Gly Lys Val Glu Leu Leu Pro Lys Val His Ile Tyr Gln Lys
    1490            1495            1500

Asp Leu Phe Pro Thr Glu Thr Ser Asn Gly Ser Pro Gly His Leu
    1505            1510            1515

Asp Leu Val Glu Gly Ser Leu Leu Gln Gly Thr Glu Gly Ala Ile
    1520            1525            1530

Lys Trp Asn Glu Ala Asn Arg Pro Gly Lys Val Pro Phe Leu Arg
    1535            1540            1545
```

```
Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
```

-continued

```
              1940                1945                1950
His Ser Ile His Phe Ser Gly His Val Phe Thr Val Arg Lys Lys
      1955                1960                1965

Glu Glu Tyr Lys Met Ala Leu Tyr Asn Leu Tyr Pro Gly Val Phe
      1970                1975                1980

Glu Thr Val Glu Met Leu Pro Ser Lys Ala Gly Ile Trp Arg Val
      1985                1990                1995

Glu Cys Leu Ile Gly Glu His Leu His Ala Gly Met Ser Thr Leu
      2000                2005                2010

Phe Leu Val Tyr Ser Asn Lys Cys Gln Thr Pro Leu Gly Met Ala
      2015                2020                2025

Ser Gly His Ile Arg Asp Phe Gln Ile Thr Ala Ser Gly Gln Tyr
      2030                2035                2040

Gly Gln Trp Ala Pro Lys Leu Ala Arg Leu His Tyr Ser Gly Ser
      2045                2050                2055

Ile Asn Ala Trp Ser Thr Lys Glu Pro Phe Ser Trp Ile Lys Val
      2060                2065                2070

Asp Leu Leu Ala Pro Met Ile Ile His Gly Ile Lys Thr Gln Gly
      2075                2080                2085

Ala Arg Gln Lys Phe Ser Ser Leu Tyr Ile Ser Gln Phe Ile Ile
      2090                2095                2100

Met Tyr Ser Leu Asp Gly Lys Lys Trp Gln Thr Tyr Arg Gly Asn
      2105                2110                2115

Ser Thr Gly Thr Leu Met Val Phe Phe Gly Asn Val Asp Ser Ser
      2120                2125                2130

Gly Ile Lys His Asn Ile Phe Asn Pro Pro Ile Ile Ala Arg Tyr
      2135                2140                2145

Ile Arg Leu His Pro Thr His Tyr Ser Ile Arg Ser Thr Leu Arg
      2150                2155                2160

Met Glu Leu Met Gly Cys Asp Leu Asn Ser Cys Ser Met Pro Leu
      2165                2170                2175

Gly Met Glu Ser Lys Ala Ile Ser Asp Ala Gln Ile Thr Ala Ser
      2180                2185                2190

Ser Tyr Phe Thr Asn Met Phe Ala Thr Trp Ser Pro Ser Lys Ala
      2195                2200                2205

Arg Leu His Leu Gln Gly Arg Ser Asn Ala Trp Arg Pro Gln Val
      2210                2215                2220

Asn Asn Pro Lys Glu Trp Leu Gln Val Asp Phe Gln Lys Thr Met
      2225                2230                2235

Lys Val Thr Gly Val Thr Thr Gln Gly Val Lys Ser Leu Leu Thr
      2240                2245                2250

Ser Met Tyr Val Lys Glu Phe Leu Ile Ser Ser Ser Gln Asp Gly
      2255                2260                2265

His Gln Trp Thr Leu Phe Phe Gln Asn Gly Lys Val Lys Val Phe
      2270                2275                2280

Gln Gly Asn Gln Asp Ser Phe Thr Pro Val Val Asn Ser Leu Asp
      2285                2290                2295

Pro Pro Leu Leu Thr Arg Tyr Leu Arg Ile His Pro Gln Ser Trp
      2300                2305                2310

Val His Gln Ile Ala Leu Arg Met Glu Val Leu Gly Cys Glu Ala
      2315                2320                2325

Gln Asp Leu Tyr
      2330
```

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: B-domain
      linker peptide

<400> SEQUENCE: 10

Ser Phe Ser Gln Asn Ser Arg His
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: B-domain
      linker peptide

<400> SEQUENCE: 11

Gln Ala Tyr Arg Tyr Arg Arg Gly
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: B-domain
      linker peptide

<400> SEQUENCE: 12

Ser Phe Ser Gln Asn Ser Arg His Gln Ala Tyr Arg Tyr Arg Arg Gly
1               5                   10                  15

<210> SEQ ID NO 13
<211> LENGTH: 2478
<212> TYPE: DNA
<213> ORGANISM: Homo sapiens

<400> SEQUENCE: 13
agtcccatgg ggaatgtcaa caggcagggg cagcactgca gagatttcat catggtctcc      60
caggccctca ggctcctctg ccttctgctt gggcttcagg gctgcctggc tgcaggcggg     120
gtcgctaagg cctcaggagg agaaacacgg gacatgccgt ggaagccggg gcctcacaga     180
gtcttcgtaa cccaggagga agcccacggc gtcctgcacc ggcgccggcg cgccaacgcg     240
ttcctggagg agctgcggcc gggctccctg gagagggagt gcaaggagga gcagtgctcc     300
ttcgaggagc ccgggagatc ttcaaggacg cggagaggac gaagctgttc tggatttct     360 tacagtgatg gggaccagtg tgcctcaagt ccatgccaga atgggggctc ctgcaaggac     420
cagctccagt cctatatctg cttctgcctc cctgccttcg agggccggaa ctgtgagacg     480
cacaaggatg accagctgat ctgtgtgaac gagaacggcg gctgtgagca gtactgcagt     540
gaccacacgg gcaccaagcg ctcctgtcgg tgccacgagg ggtactctct gctggcagac     600
ggggtgtcct gcacccacg agttgaatat ccatgtggaa aaataccat tctagaaaaa      660 agaaatgcca gcaaacccca aggccgaatt gtgggggca agtgtgccc caaggggag       720 tgtccatggc aggtcctgtt gttggtgaat ggagctcagt tgtgtggggg accctgatc     780 aacaccatct gggtggtctc cgcggcccac tgtttcgaca aaatcaagaa ctggaggaac     840

-continued

| | |
|---|---|
| ctgatcgcgg tgctgggcga gcacgacctc agcgagcacg acggggatga gcagagccgg | 900 |
| cgggtggcgc aggtcatcat ccccagcacg tacgtcccgg gcaccaccaa ccacgacatc | 960 |
| gcgctgctcc gcctgcacca gcccgtggtc ctcactgacc atgtggtgcc cctctgcctg | 1020 |
| cccgaacgga cgttctctga gaggacgctg gccttcgtgc gcttctcatt ggtcagcggc | 1080 |
| tggggccagc tgctggaccg tggcgccacg gccctggagc tcatggtgct caacgtgccc | 1140 |
| cggctgatga cccaggactg cctgcagcag tcacggaagg tgggagactc ccaaaatatc | 1200 |
| acggagtaca tgttctgtgc cggctactcg gatggcagca aggactcctg caagggggac | 1260 |
| agtggaggcc cacatgccac ccactaccgg ggcacgtggt acctgacggg catcgtcagc | 1320 |
| tggggccagg gctgcgcaac cgtgggccac tttggggtgt acaccagggt ctcccagtac | 1380 |
| atcgagtggc tgcaaaagct catgcgctca gagccacgcc caggagtcct cctgcgagcc | 1440 |
| ccatttccct agcccagcag ccctggcctg tggagagaaa gccaaggctg cgtcgaactg | 1500 |
| tcctggcacc aaatcccata tattcttctg cagttaatgg ggtagaggag ggcatgggag | 1560 |
| ggagggagag gtggggaggg agacagagac agaaacagag agacagagag acagagagag | 1620 |
| actgagggag agactctgag gacatggaga gagactcaaa gagactccaa gattcaaaga | 1680 |
| gactaataga gacacagaga tggaatagaa aagatgagag gcagaggcag acaggcgctg | 1740 |
| gacagagggg caggggagtg ccaaggttgt cctggaggca gacagcccag ctgagcctcc | 1800 |
| ttacctccct tcagccaagc cccacctgca cgtgatctgc tggccctcag gctgctgctc | 1860 |
| tgccttcatt gctggagaca gtagaggcat gaacacacat ggatgcacac acacacacgc | 1920 |
| caatgcacac acacagagat atgcacacac acgggatgcac acacagatgg tcacacagag | 1980 |
| atacgcaaac acccgatgc acacgcacat agagatatgc acacagat gcacacacag | 2040 |
| atatacacat ggatgcacgc acatgccaat gcacgcacac atcagtgcac acggatgcac | 2100 |
| agagatatgc acaccgat gtgcgcacac acagatatgc acacatgg atgagcacac | 2160 |
| acacaccaag tgcgcacaca caccgatgta cacacacaga tgcacacaca gatgcacaca | 2220 |
| caccgatgct gactccatgt gtgctgtcct ctgaaggcgg ttgtttagct ctcacttttc | 2280 |
| tggttcttat ccattatcat cttcacttca gacaattcag aagcatcacc atgcatggtg | 2340 |
| gcgaatgccc ccaaactctc ccccaaatgt atttctccct tcgctgggtg ccgggctgca | 2400 |
| cagactattc cccacctgct tcccagcttc acaataaacg gctgcgtctc ctccgcacac | 2460 |
| ctgtggtgcc tgccaccc | 2478 |

<210> SEQ ID NO 14
<211> LENGTH: 2412
<212> TYPE: DNA
<213> ORGANISM: Homo sapiens

<400> SEQUENCE: 14

| | |
|---|---|
| agtcccatgg ggaatgtcaa caggcagggg cagcactgca gagatttcat catggtctcc | 60 |
| caggccctca ggctcctctg ccttctgctt gggcttcagg gctgcctggc tgcagtcttc | 120 |
| gtaacccagg aggaagccca cggcgtcctg caccggcgcc ggcgcgccaa cgcgttcctg | 180 |
| gaggagctgc ggccgggctc cctggagagg gagtgcaagg aggagcagtg ctccttcgag | 240 |
| gaggcccggg agatcttcaa ggacgcggag aggacgaagc tgttctggat ttcttacagt | 300 |
| gatggggacc agtgtgcctc aagtccatgc cagaatgggg ctcctgcaa ggaccagctc | 360 |
| cagtcctata tctgcttctg cctccctgcc ttcgagggcc ggaactgtga gacgcacaag | 420 |
| gatgaccagc tgatctgtgt gaacgagaac ggcggctgtg agcagtactg cagtgaccac | 480 |

```
acgggcacca agcgctcctg tcggtgccac gaggggtact ctctgctggc agacggggtg      540
tcctgcacac ccacagttga atatccatgt ggaaaaatac ctattctaga aaaagaaat       600 gccagcaaac cccaaggccg aattgtgggg ggcaaggtgt gccccaaagg ggagtgtcca      660
tggcaggtcc tgttgttggt gaatggagct cagttgtgtg gggggaccct gatcaacacc      720
atctgggtgg tctccgcggc ccactgtttc gacaaaatca agaactggag gaacctgatc      780
gcggtgctgg cgagcacga cctcagcgag cacgacgggg atgagcagag ccggcgggtg       840
gcgcaggtca tcatccccag cacgtacgtc ccgggcacca ccaaccacga catcgcgctg      900
ctccgcctgc accagcccgt ggtcctcact gaccatgtgg tgcccctctg cctgcccgaa      960
cggacgttct ctgagaggac gctggccttc gtgcgcttct cattggtcag cggctggggc      1020
cagctgctgg accgtggcgc cacggccctg gagctcatgg tgctcaacgt gccccggctg      1080
atgacccagg actgcctgca gcagtcacgg aaggtgggag actccccaaa tatcacggag      1140
tacatgttct gtgccggcta ctcggatggc agcaaggact cctgcaaggg ggacagtgga      1200
ggcccacatg ccacccacta ccggggcacg tggtacctga cgggcatcgt cagctggggc      1260
cagggctgcg caaccgtggg ccactttggg gtgtacacca gggtctccca gtacatcgag      1320
tggctgcaaa agctcatgcg ctcagagcca cgcccaggag tcctcctgcg agccccattt      1380
ccctagccca gcagccctgg cctgtggaga gaaagccaag gctgcgtcga actgtcctgg      1440
caccaaatcc catatattct tctgcagtta atggggtaga ggagggcatg ggagggaggg      1500
agaggtgggg agggagacag agacagaaac agagagagac agagacagag agagactgag      1560
ggagagactc tgaggacatg gagagagact caaagagact ccaagattca aagagactaa      1620
tagagacaca gagatggaat agaaaagatg agaggcagag gcagacaggc gctggacaga      1680
ggggcagggg agtgccaagg ttgtcctgga ggcagacagc ccagctgagc ctccttacct      1740
cccttcagcc aagccccacc tgcacgtgat ctgctggccc tcaggctgct gctctgcctt      1800
cattgctgga gacagtagag gcatgaacac acatggatgc acacacacac acgccaatgc      1860
acacacacag agatatgcac acacacggat gcacacacag atggtcacac agagatacgc      1920
aaacacaccg atgcacacgc acatagagat atgcacacac agatgcacac acagatatac      1980
acatggatgc acgcacatgc caatgcacgc acacatcagt gcacgggat gcacagagat       2040 atgcacacac cgatgtgcgc acacacagat atgcacacac atggatgagc acacacacac      2100
caagtgcgca cacaccga tgtacacaca cagatgcaca cacagatgca cacacaccga       2160
tgctgactcc atgtgtgctg tcctctgaag gcggttgttt agctctcact tttctggttc      2220
ttatccatta tcatcttcac ttcagacaat tcagaagcat caccatgcat ggtggcgaat      2280
gcccccaaac tctcccccaa atgtatttct cccttcgctg ggtgccgggc tgcacagact      2340
attccccacc tgcttcccag cttcacaata aacggctgcg tctcctccgc acacctgtgg      2400
tgcctgccac cc                                                         2412
```

<210> SEQ ID NO 15
<211> LENGTH: 1518
<212> TYPE: DNA
<213> ORGANISM: Homo sapiens

<400> SEQUENCE: 15

```
aaaacagccc ggagcctgca gcccagcccc acccagaccc atggctggac ctgccaccca       60
gagccccatg aagctgatgg ccctgcagct gctgctgtgg cacagtgcac tctggacagt      120
```

```
gcaggaagcc accccctgg gccctgccag ctccctgccc cagagcttcc tgctcaagtg    180
cttagagcaa gtgaggaaga tccagggcga tggcgcagcg ctccaggaga agctggtgag    240
tgagtgtgcc acctacaagc tgtgccaccc cgaggagctg gtgctgctcg acactctct    300
gggcatcccc tgggctcccc tgagcagctg ccccagccag gccctgcagc tggcaggctg    360
cttgagccaa ctccatagcg gccttttcct ctaccagggg ctcctgcagg ccctggaagg    420
gatctccccc gagttgggtc ccaccttgga cacactgcag ctggacgtcg ccgactttgc    480
caccaccatc tggcagcaga tggaagaact gggaatggcc cctgccctgc agcccaccca    540
gggtgccatg ccggccttcg cctctgcttt ccagcgccgg caggagggg tcctggttgc    600
ctcccatctg cagagcttcc tggaggtgtc gtaccgcgtt tacgccacc ttgcccagcc    660
ctgagccaag ccctccccat cccatgtatt tatctctatt taatatttat gtctatttaa    720
gcctcatatt taaagacagg gaagagcaga acggagcccc aggcctctgt gtccttccct    780
gcatttctga gtttcattct cctgcctgta gcagtgagaa aaagctcctg tcctcccatc    840
ccctggactg ggaggtagat aggtaaatac caagtattta ttactatgac tgctccccag    900
ccctggctct gcaatgggca ctgggatgag ccgctgtgag ccctggtcc tgagggtccc    960
cacctgggac ccttgagagt atcaggtctc ccacgtggga gacaagaaat ccctgtttaa    1020
tatttaaaca gcagtgttcc ccatctgggt ccttgcaccc ctcactctgg cctcagccga    1080
ctgcacagcg gccctgcat ccccttggct gtgaggcccc tggacaagca gaggtggcca    1140
gagctgggag gcatggccct ggggtcccac gaatttgctg gggaatctcg ttttcttct    1200
taagactttt gggacatggt ttgactcccg aacatcaccg acgtgtctcc tgttttctg    1260
ggtggcctcg ggacacctgc cctgccccca cgagggtcag gactgtgact cttttagg    1320
ccaggcaggt gcctggacat ttgccttgct ggacggggac tggggatgtg ggagggagca    1380
gacaggagga atcatgtcag gcctgtgtgt gaaaggaagc tccactgtca ccctccacct    1440
cttcaccccc cactcaccag tgtccccctcc actgtcacat tgtaactgaa cttcaggata    1500
ataaagtgtt tgcctcca                                                  1518

<210> SEQ ID NO 16
<211> LENGTH: 1509
<212> TYPE: DNA
<213> ORGANISM: Homo sapiens

<400> SEQUENCE: 16
aaaacagccc ggagcctgca gcccagcccc acccagaccc atggctggac ctgccaccca     60
gagccccatg aagctgatgg ccctgcagct gctgctgtgg cacagtgcac tctggacagt    120
gcaggaagcc accccctgg gccctgccag ctccctgccc cagagcttcc tgctcaagtg    180
cttagagcaa gtgaggaaga tccagggcga tggcgcagcg ctccaggaga agctgtgtgc    240
cacctacaag ctgtgccacc ccgaggagct ggtgctgctc ggacactctc tgggcatccc    300
ctgggctccc ctgagcagct gccccagcca ggccctgcag ctggcaggct gcttgagcca    360
actccatagc ggccttttcc tctaccaggg gctcctgcag gccctggaag ggatctcccc    420
cgagttgggt cccaccttgg acacactgca gctggacgtc gccgactttg ccaccaccat    480
ctggcagcag atggaagaac tgggaatggc ccctgccctg cagcccaccc agggtgccat    540
gccggccttc gcctctgctt tccagcgccg gcagggg gtcctggttg cctcccatct    600
gcagagcttc ctggaggtgt cgtaccgcgt tctacgccac cttgcccagc cctgagccaa    660
gccctcccca tcccatgtat ttatctctat ttaatattta tgtctattta gcctcatat    720
```

```
ttaaagacag ggaagagcag aacggagccc caggcctctg tgtccttccc tgcatttctg      780
agtttcattc tcctgcctgt agcagtgaga aaaagctcct gtcctccat cccctggact       840 gggaggtaga taggtaaata ccaagtattt attactatga ctgctcccca gccctggctc      900
tgcaatgggc actgggatga gccgctgtga gcccctggtc ctgagggtcc ccacctggga      960
cccttgagag tatcaggtct cccacgtggg agacaagaaa tccctgttta atatttaaac     1020
agcagtgttc cccatctggg tccttgcacc cctcactctg gcctcagccg actgcacagc     1080
ggcccctgca tccccttggc tgtgaggccc ctggacaagc agaggtggcc agagctggga     1140
ggcatggccc tggggtccca cgaatttgct ggggaatctc gttttcttc ttaagacttt      1200 tgggacatgg tttgactccc gaacatcacc gacgtgtctc ctgttttct gggtggcctc      1260 gggacacctg ccctgccccc acgagggtca ggactgtgac tctttttagg gccaggcagg     1320
tgcctggaca tttgccttgc tggacgggga ctggggatgt gggagggagc agacaggagg     1380
aatcatgtca ggcctgtgtg tgaaaggaag ctccactgtc accctccacc tcttcaccc      1440 ccactcacca gtgtcccctc cactgtcaca ttgtaactga acttcaggat aataaagtgt     1500
ttgcctcca                                                             1509

<210> SEQ ID NO 17
<211> LENGTH: 1703
<212> TYPE: DNA
<213> ORGANISM: Homo sapiens

<400> SEQUENCE: 17
aaaacagccc ggagcctgca gcccagcccc acccagaccc atggctggac ctgccaccca       60
gagccccatg aagctgatgg gtgagtgtct tggcccagga tgggagagcc gcctgccctg      120
gcatgggagg gaggctggtg tgacagaggg gctggggatc cccgttctgg gaatggggat      180
taaaggcacc cagtgtcccc gagagggcct caggtggtag ggaacagcat gtctcctgag      240
cccgctctgt ccccagccct gcagctgctg ctgtggcaca gtgcactctg gacagtgcag      300
gaagccaccc cctgggccc tgccagctcc ctgccccaga gcttcctgct caagtgctta      360
gagcaagtga ggaagatcca gggcgatggc gcagcgctcc aggagaagct gtgtgccacc      420
tacaagctgt gccaccccga ggagctggtg ctgctcggac actctctggg catcccctgg      480
gctcccctga gcagctgccc cagccaggcc ctgcagctgg caggctgctt gagccaactc      540
catagcggcc ttttcctcta ccaggggctc ctgcaggccc tggaagggat ctcccccgag      600
ttgggtccca ccttggacac actgcagctg gacgtcgccg actttgccac caccatctgg      660
cagcagatgg aagaactggg aatggcccct gccctgcagc ccacccaggg tgccatgccg      720
gccttcgcct ctgctttcca gcgccgggca ggagggtgtcc tggttgcctc ccatctgcag      780
agcttcctgg aggtgtcgta ccgcgttcta cgccaccttg cccagccctg agccaagccc      840
tccccatccc atgtatttat ctctatttaa tatttatgtc tatttaagcc tcatatttaa      900
agacagggaa gagcagaacg gagccccagg cctctgtgtc cttccctgca tttctgagtt      960
tcattctcct gcctgtagca gtgagaaaaa gctcctgtcc tccatcccc tggactggga     1020 ggtagatagg taaataccaa gtatttatta ctatgactgc tccccagccc tggctctgca     1080
atgggcactg ggatgagccg ctgtgagccc ctggtcctga gggtcccac ctgggaccct     1140 tgagagtatc aggtctccca cgtgggagac aagaaatccc tgtttaatat ttaaacagca     1200
gtgttcccca tctgggtcct tgcacccctc actctggcct cagccgactg cacagcggcc     1260
```

```
cctgcatccc cttggctgtg aggcccctgg acaagcagag gtggccagag ctgggaggca    1320
tggccctggg gtcccacgaa tttgctgggg aatctcgttt ttcttcttaa gacttttggg    1380
acatggtttg actcccgaac atcaccgacg tgtctcctgt ttttctgggt ggcctcggga    1440
cacctgccct gcccccacga gggtcaggac tgtgactctt tttagggcca ggcaggtgcc    1500
tggacatttg ccttgctgga cggggactgg ggatgtggga gggagcagac aggaggaatc    1560
atgtcaggcc tgtgtgtgaa aggaagctcc actgtcaccc tccacctctt caccccccac    1620
tcaccagtgt cccctccact gtcacattgt aactgaactt caggataata agtgtttgc     1680 ctccaaaaaa aaaaaaaaaa aaa                                            1703

<210> SEQ ID NO 18
<211> LENGTH: 8923
<212> TYPE: DNA
<213> ORGANISM: Homo sapiens

<400> SEQUENCE: 18
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240
gcaggggaag gcaccattgt ccagcagctg agtttcccag ggaccttgga gatagccgca     300
gccctcattt atgattcctg ccagatttgc cggggtgctg cttgctctgg ccctcatttt     360
gccagggacc ctttgtgcag aaggaactcg cggcaggtca tccacggccc gatgcagcct     420
tttcggaagt gacttcgtca acacctttga tgggagcatg tacagctttg cgggatactg     480
cagttacctc ctggcagggg gctgccagaa acgctcctcc tcgattattg gggacttcca     540
gaatggcaag agagtgagcc tctccgtgta tcttgggaa ttttttgaca tccatttgtt     600
tgtcaatggt accgtgacac aggggggacca aagagtctcc atgccctatg cctccaaagg     660
gctgtatcta gaaactgagg ctgggtacta caagctgtcc ggtgaggcct atggctttgt     720
ggccaggatc gatggcagcg gcaacttttca agtcctgctg tcagacagat acttcaacaa     780
gacctgcggg ctgtgtggca actttaacat cttttgctgaa gatgacttta tgacccaaga     840
agggaccttg acctcggacc cttatgactt tgccaactca tgggctctga gcagtggaga     900
acagtggtgt gaacgggcat ctcctcccag cagctcatgc aacatctcct ctggggaaat     960
gcagaagggc ctgtgggagc agtgccagct tctgaagagc acctcggtgt ttgcccgctg    1020
ccaccctctg gtggacccccg agccttttgt ggccctgtgt gagaagactt tgtgtgagtg    1080
tgctgggggg ctggagtgcg cctgccctgc cctcctggag tacgcccgga cctgtgccca    1140
ggagggaatg gtgctgtacg gctggaccga ccacagcgcg tgcagcccag tgtgccctgc    1200
tggtatggag tataggcagt gtgtgtcccc ttgcgccagg acctgccaga gcctgcacat    1260
caatgaaatg tgtcaggagc gatgcgtgga tggctgcagc tgccctgagg acagctcct    1320 ggatgaaggc ctctgcgtgg agagcaccga gtgtccctgc gtgcattccg gaaagcgcta    1380 ccctccccggc acctccctct ctcgagactg caacacctgc atttgccgaa acagccagtg    1440
gatctgcagc aatgaagaat gtccaggga gtgccttgtc actggtcaat cccacttcaa    1500
gagctttgac aacagatact tcaccttcag tgggatctgc cagtacctgc tggcccggga    1560
ttgccaggac cactccttct ccattgtcat tgagactgtc cagtgtgctg atgaccgcga    1620
cgctgtgtgc acccgctccg tcaccgtccg gctgcctggc ctgcacaaca gccttgtgaa    1680
```

```
actgaagcat ggggcaggag ttgccatgga tggccaggac atccagctcc ccctcctgaa   1740
aggtgacctc cgcatccagc atacagtgac ggcctccgtg cgcctcagct acggggagga   1800
cctgcagatg gactgggatg ccgcggag gctgctggtg aagctgtccc ccgtctacgc     1860
cgggaagacc tgcggcctgt gtgggaatta caatggcaac cagggcgacg acttccttac   1920
cccctctggg ctggcagagc cccgggtgga ggacttcggg aacgcctgga agctgcacgg   1980
ggactgccag gacctgcaga agcagcacag cgatccctgc gccctcaacc cgcgcatgac   2040
caggttctcc gaggaggcgt gcgcggtcct gacgtccccc acattcgagg cctgccatcg   2100
tgccgtcagc ccgctgccct acctgcggaa ctgccgctac gacgtgtgct cctgctcgga   2160
cggccgcgag tgcctgtgcg gcgccctggc cagctatgcc gcggcctgcg cggggagagg   2220
cgtgcgcgtc gcgtggcgcg agccaggccg ctgtgagctg aactgcccga aggccaggt   2280
gtacctgcag tgcgggaccc cctgcaacct gacctgccgc tctctctctt acccggatga   2340
ggaatgcaat gaggcctgcc tggagggctg cttctgcccc ccagggctct acatggatga   2400
gagggggggac tgcgtgccca aggccagtg cccctgttac tatgacggtg agatcttcca   2460
gccagaagac atcttctcag accatcacac catgtgctac tgtgaggatg gcttcatgca   2520
ctgtaccatg agtggagtcc ccggaagctt gctgcctgac gctgtcctca gcagtcccct   2580
gtctcatcgc agcaaaagga gcctatcctg tcggccccc atggtcaagc tggtgtgtcc   2640
cgctgacaac ctgcgggctg aagggctcga gtgtaccaaa acgtgccaga actatgacct   2700
ggagtgcatg agcatgggct gtgtctctgg ctgcctctgc ccccgggca tggtccggca   2760
tgagaacaga tgtgtggccc tggaaaggtg tccctgcttc catcagggca aggagtatgc   2820
ccctggagaa acagtgaaga ttggctgcaa cacttgtgtc tgtcgggacc ggaagtggaa   2880
ctgcacagac catgtgtgtg atgccacgtg ctccacgatc ggcatggccc actacctcac   2940
cttcgacggg ctcaaatacc tgttccccgg ggagtgccag tacgttctgg tgcaggatta   3000
ctgcggcagt aaccctggga cctttcggat cctagtgggg aataagggat gcagccaccc   3060
ctcagtgaaa tgcaagaaac gggtcaccat cctggtggag ggaggagaga ttgagctgtt   3120
tgacggggag gtgaatgtga agaggcccat gaaggatgag actcactttg aggtggtgga   3180
gtctggccgg tacatcattc tgctgctggg caaagccctc tccgtggtct gggaccgcca   3240
cctgagcatc tccgtggtcc tgaagcagac ataccaggaa aaagtgtgtg gcctgtgtgg   3300
gaatttt gat ggcatccaga acaatgacct caccagcagc aacctccaag tggaggaaga   3360
ccctgtggac tttgggaact cctggaaagt gagctcgcag tgtgctgaca ccagaaaagt   3420
gcctctggac tcatcccctg ccacctgcca taacaacatc atgaagcaga cgatggtgga   3480
ttcctcctgt agaatcctta ccagtgacgt cttccaggac tgcaacaagc tggtggaccc   3540
cgagccatat ctggatgtct gcatttacga caccgctcc tgtgagtcca ttggggactg   3600
cgcctgcttc tgcgacacca ttgctgccta tgccacgtg tgtgcccagc atggcaaggt   3660
ggtgacctgg aggacggcca cattgtgccc ccagagctgc gaggagagga atctccggga   3720
gaacgggtat gagtgtgagt ggcgctataa cagctgtgca cctgcctgtc aagtcacgtg   3780
tcagcaccct gagccactgg cctgccctgt gcagtgtgtg gagggctgcc atgcccactg   3840
ccctccaggg aaaatcctgg atgagctttt gcagacctgc gttgaccctg aagactgtcc   3900
agtgtgtgag gtgctggccg gcgtttttgc ctcaggaaag aaagtcacct tgaatcccag   3960
tgaccctgag cactgccaga tttgccactg tgatgttgtc aaccctacct gtgaagcctg   4020
```

```
ccaggagccg ggaggcctgg tggtgcctcc cacagatgcc ccggtgagcc ccaccactct   4080
gtatgtggag acatctcgg aaccgccgtt gcacgatttc tactgcagca ggctactgga   4140
cctggtcttc ctgctggatg ctcctccag gctgtccgag gctgagtttg aagtgctgaa   4200
ggcctttgtg gtggacatga tggagcggct gcgcatctcc cagaagtggg tccgcgtggc   4260
cgtggtggag taccacgacg gctcccacgc ctacatcggg ctcaaggacc ggaagcgacc   4320
gtcagagctg cggcgcattg ccagccaggt gaagtatgcg ggcagccagg tggcctccac   4380
cagcgaggtc ttgaaataca cactgttcca aatcttcagc aagatcgacc gccctgaagc   4440
ctcccgcatc gccctgctcc tgatggccag ccaggagccc aacggatgt cccgaacctt    4500
tgtccgctac gtccagggcc tgaagaagaa gaaggtcatt gtgatcccgg tgggcattgg   4560
gccccatgcc aacctcaagc agatccgcct catcgagaag caggccctg agaacaaggc    4620
cttcgtgctg agcagtgtgg atgagctgga gcagcaaagg gacgagatcg ttagctacct   4680
ctgtgacctt gccctgaag ccctcctcc tactctgccc cccacatgg cacaagtcac     4740
tgtgggcccg gggctcttgg ggtttcgac cctgggcc aagaggaact ccatggttct      4800
ggatgtggcg ttcgtcctgg aaggatcgga caaaattggt gaagccgact tcaacaggag   4860
caaggagttc atggaggagg tgattcagcg gatggatgtg ggccaggaca gcatccacgt   4920
cacggtgctg cagtactcct acatggtgac cgtggagtac cccttcagcg aggcacagtc   4980
caaaggggac atcctgcagc gggtgcgaga gatccgctac cagggcggca acaggaccaa   5040
cactgggctg gccctgcggt acctctctga ccacagcttc ttggtcagcc agggtgaccg   5100
ggagcaggcg cccaacctgg tctacatggt caccggaaat cctgcctctg atgagatcaa   5160
gaggctgcct ggagacatcc aggtggtgcc cattggagtg ggccctaatg ccaacgtgca   5220
ggagctggag aggattggct ggcccaatgc ccctatcctc atccaggact ttgagacgct   5280
cccccgagag gctcctgacc tggtgctgca gaggtgctgc tccggagagg ggctgcagat   5340
ccccaccctc tccctgcac ctgactgcag ccagccctg gacgtgatcc ttctcctgga    5400
tggctcctcc agtttcccag cttcttattt tgatgaaatg aagagtttcg ccaaggcttt   5460
catttcaaaa gccaatatag ggcctcgtct cactcaggtg tcagtgctgc agtatggaag   5520
catcaccacc attgacgtgc catggaacgt ggtcccggag aaagcccatt gctgagcct    5580
tgtggacgtc atgcagcggg agggaggccc cagccaaatc ggggatgcct gggctttgc    5640
tgtgcgatac ttgacttcag aaatgcatgg tgccaggccg ggagcctcaa aggcggtggt   5700
catcctggtc acggacgtct ctgtggattc agtggatgca gcagctgatg ccgccaggtc   5760
caacagagtg acagtgttcc ctattggaat tggagatcgc tacgatgcag cccagctacg   5820
gatcttggca ggcccagcag gcgactccaa cgtggtgaag ctccagcgaa tcgaagacct   5880
ccctaccatg gtcaccttgg gcaattcctt cctccacaaa ctgtgctctg gatttgttag   5940
gatttgcatg gatgaggatg ggaatgagaa gaggcccggg gacgtctgga ccttgccaga   6000
ccagtgccac accgtgactt gccagccaga tggccagacc ttgctgaaga gtcatcgggt   6060
caactgtgac cggggggctga ggccttcgtg ccctaacagc cagtccccctg ttaaagtgga  6120
agagacctgt ggctgccgct ggaccctgccc ctgcgtgtgc acaggcagct ccactcggca  6180
catcgtgacc tttgatgggc agaatttcaa gctgactggc agctgttctt atgtcctatt   6240
tcaaaacaag gagcaggacc tggaggtgat tctccataat ggtgcctgca gccctggagc   6300
aaggcagggc tgcatgaaat ccatcgaggt gaagcacagt gccctctccg tcgagctgca   6360
cagtgacatg gaggtgacgg tgaatgggag actggtctct gttccttacg tgggtgggaa   6420
```

```
catggaagtc aacgtttatg gtgccatcat gcatgaggtc agattcaatc accttggtca    6480
catcttcaca ttcactccac aaaacaatga gttccaactg cagctcagcc ccaagacttt    6540
tgcttcaaag acgtatggtc tgtgtgggat ctgtgatgag aacggagcca atgacttcat    6600
gctgagggat ggcacagtca ccacagactg gaaaacactt gttcaggaat ggactgtgca    6660
gcggccaggg cagacgtgcc agcccatcct ggaggagcag tgtcttgtcc ccgacagctc    6720
ccactgccag gtcctcctct taccactgtt tgctgaatgc acaaggtcc tggctccagc     6780
cacattctat gccatctgcc agcaggacag ttgccaccag gagcaagtgt gtgaggtgat    6840
cgcctcttat gcccacctct gtcggaccaa cggggtctgc gttgactgga ggacacctga    6900
tttctgtgct atgtcatgcc caccatctct ggtctacaac cactgtgagc atggctgtcc    6960
ccggcactgt gatggcaacg tgagctcctg tggggaccat ccctccgaag ctgtttctg     7020
ccctccagat aaagtcatgt tggaaggcag ctgtgtccct gaagaggcct gcactcagtg    7080
cattggtgag gatggagtcc agcaccagtt cctggaagcc tgggtcccgg accaccagcc    7140
ctgtcagatc tgcacatgcc tcagcgggcg gaaggtcaac tgcacaacgc agccctgccc    7200
cacggccaaa gctcccacgt gtggcctgtg tgaagtagcc cgcctccgcc agaatgcaga    7260
ccagtgctgc cccgagtatg agtgtgtgtg tgacccagtg agctgtgacc tgcccccagt    7320
gcctcactgt gaacgtggcc tccagcccac actgaccaac cctggcgagt gcagacccaa    7380
cttcacctgc gcctgcagga aggaggagtg caaaagagtg tccccaccct cctgccccc    7440
gcaccgtttg cccacccttc ggaagaccca gtgctgtgat gagtatgagt gtgcctgcaa    7500
ctgtgtcaac tccacagtga gctgtcccct tgggtacttg gcctcaaccg ccaccaatga    7560
ctgtggctgt accacaacca cctgccttcc cgacaaggtg tgtgtccacc gaagcaccat    7620
ctaccctgtg ggccagttct gggaggaggg ctgcgatgtg tgcacctgca ccgacatgga    7680
ggatgccgtg atgggcctcc gcgtggccca gtgctcccag aagccctgtg aggacagctg    7740
tcggtcgggc ttcacttacg ttctgcatga aggcgagtgc tgtggaaggt gcctgccatc    7800
tgcctgtgag gtggtgactg gctcaccgcg gggggactcc cagtcttcct ggaagagtgt    7860
cggctcccag tgggcctccc cggagaaccc ctgcctcatc aatgagtgtg tccgagtgaa    7920
ggaggaggtc tttatacaac aaaggaacgt ctcctgcccc cagctggagg tccctgtctg    7980
cccctcgggc tttcagctga ctgtaagac ctcagcgtgc tgcccaagct gtcgctgtga    8040
gcgcatggag gcctgcatgc tcaatggcac tgtcattggg cccgggaaga ctgtgatgat    8100
cgatgtgtgc acgacctgcc gctgcatggt gcaggtgggg gtcatctctg gattcaagct    8160
ggagtgcagg aagaccacct gcaacccctg cccctgggt tacaaggaag aaaataacac     8220
aggtgaatgt tgtgggagat gtttgcctac ggccttcacc attcagctaa gaggaggaca   8280
gatcatgaca ctgaagcgtg atgagacgct ccaggatggc tgtgatactc acttctgcaa    8340
ggtcaatgag agaggagagt acttctggga agagggtc acaggctgcc cacccttga     8400
tgaacacaag tgtctggctg agggaggtaa aattatgaaa attccaggca cctgctgtga    8460
cacatgtgag gagcctgagt gcaacgacat cactgccagg ctgcagtatg tcaaggtggg    8520
aagctgtaag tctgaagtag aggtggatat ccactactgc cagggcaaat gtccagcaa     8580
agccatgtac tccattgaca tcaacgatgt gcaggaccag tgctcctgct gctctccgac    8640
acggacggag cccatgcagg tggccctgca ctgcaccaat ggctctgttg tgtaccatga    8700
ggttctcaat gccatggagt gcaaatgctc ccccaggaag tgcagcaagt gaggctgctg    8760
```

| | | |
|---|---|---|
| cagctgcatg ggtgcctgct gctgcctgcc ttggcctgat ggccaggcca gagtgctgcc | 8820 | |
| agtcctctgc atgttctgct cttgtgccct tctgagccca caataaaggc tgagctctta | 8880 | |
| tcttgctgca tgttctgctc ttgtgccctt ctgagccac aat | 8923 | |

<210> SEQ ID NO 19
<211> LENGTH: 24
<212> TYPE: DNA
<213> ORGANISM: artificial
<220> FEATURE:
<223> OTHER INFORMATION: primer

<400> SEQUENCE: 19
atggctggac ctgccaccca gagc            24

<210> SEQ ID NO 20
<211> LENGTH: 24
<212> TYPE: DNA
<213> ORGANISM: artificial
<220> FEATURE:
<223> OTHER INFORMATION: primer

<400> SEQUENCE: 20
tcagggctgg gcaaggtggc gtag            24

<210> SEQ ID NO 21
<211> LENGTH: 4542
<212> TYPE: DNA
<213> ORGANISM: artificial
<220> FEATURE:
<223> OTHER INFORMATION: vector PCR2.1d2-GCSFb

<400> SEQUENCE: 21

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagcttg | 240 |
| gtaccgagct cggatccact agtaacggcc gccagtgtgc tggaattcgg ctatggctgg | 300 |
| acctgccacc cagagcccca tgaagctgat ggccctgcag ctgctgctgt ggcacagtgc | 360 |
| actctggaca gtgcaggaag ccaccccct gggcctgcc agctccctgc ccagagctt | 420 |
| cctgctcaag tgcttagagc aagtgaggaa gatccagggc gatggcgcag cgctccagga | 480 |
| gaagctgtgt gccacctaca agctgtgcca ccccgaggag ctggtgctgc tcggacactc | 540 |
| tctgggcatc ccctgggctc ccctgagcag ctgcccagc caggccctgc agctggcagg | 600 |
| ctgcttgagc caactccata gcggcctttt cctctaccag gggctcctgc aggccctgga | 660 |
| agggatctcc cccgagttgg gtcccacctt ggacacactg cagctggacg tcgccgactt | 720 |
| tgccaccacc atctggcagc agatggaaga ctgggaatg ccctgccc tgcagcccac | 780 |
| ccagggtgcc atgccggcct tcgcctctgc ttccagcgc cgggcaggag gggtcctggt | 840 |
| tgcctcccat ctgcagagct tcctggaggt gtcgtaccgc gttctacgcc accttgccca | 900 |
| gccctgaagc cgaattctgc agatatccat cacactggcg gccgctcgag catgcatcta | 960 |
| gagggcccaa ttcgccctat agtgagtcgt attacaattc actggccgtc gttttacaac | 1020 |
| gtcgtgactg ggaaaaccct ggcgttaccc aacttaatcg ccttgcagca catccccctt | 1080 |
| tcgccagctg gcgtaatagc gaagaggccc gcaccgatcg cccttcccaa cagttgcgca | 1140 |
| gcctgaatgg cgaatggacg cgccctgtag cggcgcatta agcgcggcgg gtgtggtggt | 1200 |

```
tacgcgcagc gtgaccgcta cacttgccag cgccctagcg cccgctcctt tcgctttctt    1260
cccttccttt ctcgccacgt tcgccggctt tccccgtcaa gctctaaatc gggggctccc    1320
tttagggttc cgatttagtg ctttacggca cctcgacccc aaaaaacttg attagggtga    1380
tggttcacgt agtgggccat cgccctgata gacggttttt cgccctttga cgttggagtc    1440
cacgttcttt aatagtggac tcttgttcca aactggaaca acactcaacc ctatctcggt    1500
ctattctttt gatttataag ggattttgcc gatttcggcc tattggttaa aaaatgagct    1560
gatttaacaa aaatttaacg cgaattttaa caaaattcag ggcgcaaggg ctgctaaagg    1620
aagcggaaca cgtagaaagc cagtccgcag aaacggtgct gaccccggat gaatgtcagc    1680
tactgggcta tctggacaag ggaaaacgca agcgcaaaga gaaagcaggt agcttgcagt    1740
gggcttacat ggcgatagct agactgggcg gttttatgga cagcaagcga accggaattg    1800
ccagctgggg cgccctctgg taaggttggg aagccctgca agtaaactg gatggctttc     1860 ttgccgccaa ggatctgatg gcgcagggga tcaagatctg atcaagagac aggatgagga    1920
tcgtttcgca tgattgaaca agatggattg cacgcaggtt ctccggccgc ttgggtggag    1980
aggctattcg gctatgactg ggcacaacag acaatcggct gctctgatgc cgccgtgttc    2040
cggctgtcag cgcaggggcg cccggttctt tttgtcaaga ccgacctgtc cggtgccctg    2100
aatgaactgc aggacgaggc agcgcggcta tcgtggctgg ccacgacggg cgttccttgc    2160
gcagctgtgc tcgacgttgt cactgaagcg ggaagggact ggctgctatt gggcgaagtg    2220
ccggggcagg atctcctgtc atcccacctt gctcctgccg agaaagtatc catcatggct    2280
gatgcaatgc ggcggctgca tacgcttgat ccggctacct gcccattcga ccaccaagcg    2340
aaacatcgca tcgagcgagc acgtactcgg atggaagccg gtcttgtcga tcaggatgat    2400
ctggacgaag agcatcaggg gctcgcgcca gccgaactgt tcgccaggct caaggcgcgc    2460
atgcccgacg gcgaggatct cgtcgtgacc catggcgatg cctgcttgcc gaatatcatg    2520
gtggaaaatg gccgcttttc tggattcatc gactgtggcc ggctgggtgt ggcggaccgc    2580
tatcaggaca tagcgttggc tacccgtgat attgctgaag agcttggcgg cgaatgggct    2640
gaccgcttcc tcgtgcttta cggtatcgcc gctcccgatt cgcagcgcat cgccttctat    2700
cgccttcttg acgagttctt ctgaattgaa aaaggaagag tatgagtatt caacatttcc    2760
gtgtcgccct tattcccttt tttgcggcat tttgccttcc tgttttgct cacccagaaa     2820 cgctggtgaa agtaaaagat gctgaagatc agttgggtgc acgagtgggt tacatcgaac    2880
tggatctcaa cagcggtaag atccttgaga gttttcgccc cgaagaacgt tttccaatga    2940
tgagcacttt taaagttctg ctatgtggcg cggtattatc ccgtattgac gccgggcaag    3000
agcaactcgg tcgccgcata cactattctc agaatgactt ggttgagtac tcaccagtca    3060
cagaaaagca tcttacggat ggcatgacag taagagaatt atgcagtgct gccataacca    3120
tgagtgataa cactgcggcc aacttacttc tgacaacgat cggaggaccg aaggagctaa    3180 ccgcttttt gcacaacatg ggggatcatg taactcgcct tgatcgttgg gaaccggagc    3240
tgaatgaagc cataccaaac gacgagcgtg acaccacgat gcctgtagca atggcaacaa    3300
cgttgcgcaa actattaact ggcgaactac ttactctagc ttcccggcaa caattaatag    3360
actggatgga ggcggataaa gttgcaggac cacttctgcg ctcggccctt ccggctggct    3420
ggtttattgc tgataaatct ggagccggtg agcgtgggtc tcgcggtatc attgcagcac    3480
tggggccaga tggtaagccc tcccgtatcg tagttatcta cacgacgggg agtcaggcaa    3540
```

-continued

| | |
|---|---|
| ctatggatga acgaaataga cagatcgctg agataggtgc ctcactgatt aagcattggt | 3600 |
| aactgtcaga ccaagtttac tcatatatac tttagattga tttaaaactt cattttaat | 3660 |
| ttaaaaggat ctaggtgaag atcctttttg ataatctcat gaccaaaatc ccttaacgtg | 3720 |
| agttttcgtt ccactgagcg tcagaccccg tagaaaagat caaaggatct tcttgagatc | 3780 |
| cttttttct gcgcgtaatc tgctgcttgc aaacaaaaaa accaccgcta ccagcggtgg | 3840 |
| tttgtttgcc ggatcaagag ctaccaactc tttttccgaa ggtaactggc ttcagcagag | 3900 |
| cgcagatacc aaatactgtt cttctagtgt agccgtagtt aggccaccac ttcaagaact | 3960 |
| ctgtagcacc gcctacatac ctcgctctgc taatcctgtt accagtggct gctgccagtg | 4020 |
| gcgataagtc gtgtcttacc gggttggact caagacgata gttaccggat aaggcgcagc | 4080 |
| ggtcgggctg aacggggggt tcgtgcacac agcccagctt ggagcgaacg acctacaccg | 4140 |
| aactgagata cctacagcgt gagctatgag aaagcgccac gcttcccgaa gggagaaagg | 4200 |
| cggacaggta tccggtaagc ggcagggtcg gaacaggaga gcgcacgagg gagcttccag | 4260 |
| ggggaaacgc ctggtatctt tatagtcctg tcgggtttcg ccacctctga cttgagcgtc | 4320 |
| gatttttgtg atgctcgtca ggggggcgga gcctatggaa aaacgccagc aacgcggcct | 4380 |
| ttttacggtt cctggccttt tgctggcctt ttgctcacat gttctttcct gcgttatccc | 4440 |
| ctgattctgt ggataaccgt attaccgcct ttgagtgagc tgataccgct cgccgcagcc | 4500 |
| gaacgaccga gcgcagcgag tcagtgagcg aggaagcgga ag | 4542 |

<210> SEQ ID NO 22
<211> LENGTH: 6237
<212> TYPE: DNA
<213> ORGANISM: artificial
<220> FEATURE:
<223> OTHER INFORMATION: vector pcDNA3.1-hyg(+)-GCSFb

<400> SEQUENCE: 22

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccactagt aacggccgcc agtgtgctgg | 960 |
| aattcggcta tggctggacc tgccaccag agccccatga agctgatggc cctgcagctg | 1020 |
| ctgctgtggc acagtgcact ctggacagtg caggaagcca cccccctggg ccctgccagc | 1080 |

```
tccctgcccc agagcttcct gctcaagtgc ttagagcaag tgaggaagat ccagggcgat    1140
ggcgcagcgc tccaggagaa gctgtgtgcc acctacaagc tgtgccaccc cgaggagctg    1200
gtgctgctcg acactctct gggcatcccc tgggctcccc tgagcagctg ccccagccag     1260
gccctgcagc tggcaggctg cttgagccaa ctccatagcg gccttttcct ctaccagggg    1320
ctcctgcagg ccctggaagg gatctccccc gagttgggtc ccaccttgga cacactgcag    1380
ctggacgtcg ccgactttgc caccaccatc tggcagcaga tggaagaact gggaatggcc    1440
cctgccctgc agcccaccca gggtgccatg ccggccttcg cctctgcttt ccagcgccgg    1500
gcaggagggg tcctggttgc ctcccatctg cagagcttcc tggaggtgtc gtaccgcgtt    1560
ctacgccacc ttgcccagcc ctgaagccga attctgcaga tatccatcac actggcggcc    1620
gctcgagtct agagggcccg tttaaacccg ctgatcagcc tcgactgtgc cttctagttg    1680
ccagccatct gttgtttgcc cctccccgt gccttccttg accctggaag gtgccactcc     1740
cactgtcctt tcctaataaa atgaggaaat tgcatcgcat tgtctgagta ggtgtcattc    1800
tattctgggg ggtgggtgg ggcaggacag caaggggag gattgggaag acaatagcag      1860
gcatgctggg gatgcggtgg gctctatggc ttctgaggcg gaaagaacca gctgggctc     1920 taggggtat ccccacgcgc cctgtagcgg cgcattaagc gcggcgggtg tggtggttac     1980
gcgcagcgtg accgctacac ttgccagcgc cctagcgccc gctccttcg ctttcttccc     2040 ttcctttctc gccacgttcg ccggctttcc ccgtcaagct ctaaatcggg ggctcccttt    2100
agggttccga tttagtgctt tacggcacct cgaccccaaa aaacttgatt agggtgatgg    2160
ttcacgtagt gggccatcgc cctgatagac ggttttcgc cctttgacgt tggagtccac    2220
gttctttaat agtggactct tgttccaaac tggaacaaca ctcaaccta tctcggtcta     2280 ttcttttgat ttataaggga ttttgccgat ttcggcctat tggttaaaaa atgagctgat    2340
ttaacaaaaa tttaacgcga attaattctg tggaatgtgt gtcagttagg gtgtggaaag    2400
tccccaggct ccccagcagg cagaagtatg caaagcatgc atctcaatta gtcagcaacc    2460
aggtgtggaa agtccccagg ctccccagca ggcagaagta tgcaaagcat gcatctcaat    2520
tagtcagcaa ccatagtccc gcccctaact ccgcccatcc cgcccctaac tccgccagt     2580 tccgccatt ctccgcccca tggctgacta ttttttttta tttatgcaga ggccgaggcc     2640
gcctctgcct ctgagctatt ccagaagtag tgaggaggct tttttggagg cctaggcttt    2700
tgcaaaaagc tcccgggagc ttgtatatcc attttcggat ctgatcagca cgtgatgaaa    2760
aagcctgaac tcaccgcgac gtctgtcgag aagtttctga tcgaaaagtt cgacagcgtc    2820
tccgacctga tgcagctctc ggagggcgaa gaatctcgtg ctttcagctt cgatgtagga    2880
gggcgtggat atgtcctgcg ggtaaatagc tgcgccgatg gtttctacaa agatcgttat    2940
gtttatcggc actttgcatc ggccgcgctc ccgattccgg aagtgcttga cattggggaa    3000
ttcagcgaga gcctgaccta ttgcatctcc cgccgtgcac agggtgtcac gttgcaagac    3060
ctgcctgaaa ccgaactgcc cgctgttctg cagccggtcg cggaggccat ggatgcgatc    3120
gctgcggccg atcttagcca dacgagcggg ttcggcccat tcggaccgca aggaatcggt    3180
caatacacta catggcgtga tttcatatgc gcgattgctg atccccatgt gtatcactgg    3240
caaactgtga tggacgacac cgtcagtgcg tccgtcgcgc aggctctcga tgagctgatg    3300
ctttgggccg aggactgccc cgaagtccgg cacctcgtgc acgcggattt cggctccaac    3360
aatgtcctga cggacaatgg ccgcataaca gcggtcattg actggagcga ggcgatgttc    3420
```

```
gggggattccc aatacgaggt cgccaacatc ttcttctgga ggccgtggtt ggcttgtatg    3480
gagcagcaga cgcgctactt cgagcggagg catccggagc ttgcaggatc gccgcggctc    3540
cgggcgtata tgctccgcat tggtcttgac caactctatc agagcttggt tgacggcaat    3600
ttcgatgatg cagcttgggc gcagggtcga tgcgacgcaa tcgtccgatc cggagccggg    3660
actgtcgggc gtacacaaat cgcccgcaga agcgcggccg tctggaccga tggctgtgta    3720
gaagtactcg ccgatagtgg aaaccgacgc cccagcactc gtccgagggc aaaggaatag    3780
cacgtgctac gagatttcga ttccaccgcc gccttctatg aaaggttggg cttcggaatc    3840
gttttccggg acgccggctg gatgatcctc cagcgcgggg atctcatgct ggagttcttc    3900
gcccacccca acttgtttat tgcagcttat aatggttaca aataaagcaa tagcatcaca    3960
aatttcacaa ataaagcatt tttttcactg cattctagtt gtggtttgtc caaactcatc    4020
aatgtatctt atcatgtctg tataccgtcg acctctagct agagcttggc gtaatcatgg    4080
tcatagctgt ttcctgtgtg aaattgttat ccgctcacaa ttccacacaa catacgagcc    4140
ggaagcataa agtgtaaagc ctggggtgcc taatgagtga gctaactcac attaattgcg    4200
ttgcgctcac tgcccgcttt ccagtcggga acctgtcgt gccagctgca ttaatgaatc    4260
ggccaacgcg cggggagagg cggtttgcgt attgggcgct cttccgcttc ctcgctcact    4320
gactcgctgc gctcggtcgt tcggctgcgg cgagcggtat cagctcactc aaaggcggta    4380
atacggttat ccacagaatc aggggataac gcaggaaaga acatgtgagc aaaaggccag    4440
caaaaggcca ggaaccgtaa aaaggccgcg ttgctggcgt ttttccatag gctccgcccc    4500
cctgacgagc atcacaaaaa tcgacgctca agtcagaggt ggcgaaaccc gacaggacta    4560
taaagatacc aggcgtttcc ccctggaagc tccctcgtgc gctctcctgt tccgaccctg    4620
ccgcttaccg gatacctgtc cgcctttctc ccttcgggaa gcgtggcgct ttctcatagc    4680
tcacgctgta ggtatctcag ttcggtgtag gtcgttcgct ccaagctggg ctgtgtgcac    4740
gaaccccccg ttcagcccga ccgctgcgcc ttatccggta actatcgtct tgagtccaac    4800
ccggtaagac acgacttatc gccactggca gcagccactg gtaacaggat tagcagagcg    4860
aggtatgtag gcggtgctac agagttcttg aagtggtggc ctaactacgg ctacactaga    4920
agaacagtat ttggtatctg cgctctgctg aagccagtta ccttcggaaa aagagttggt    4980
agctcttgat ccggcaaaca aaccaccgct ggtagcggtg gtttttttgt ttgcaagcag    5040
cagattacgc gcagaaaaaa aggatctcaa gaagatcctt tgatcttttc tacggggtct    5100
gacgctcagt ggaacgaaaa ctcacgttaa gggattttgg tcatgagatt atcaaaaagg    5160
atcttcacct agatcctttt aaattaaaaa tgaagtttta aatcaatcta agtatatat    5220 gagtaaactt ggtctgacag ttaccaatgc ttaatcagtg aggcacctat ctcagcgatc    5280
tgtctatttc gttcatccat agttgcctga ctccccgtcg tgtagataac tacgatacgg    5340
gagggcttac catctggccc cagtgctgca atgataccgc gagacccacg ctcaccggct    5400
ccagatttat cagcaataaa ccagccagcc ggaagggccg agcgcagaag tggtcctgca    5460
actttatccg cctccatcca gtctattaat tgttgccggg aagctagagt aagtagttcg    5520
ccagttaata gtttgcgcaa cgttgttgcc attgctacag gcatcgtggt gtcacgctcg    5580
tcgtttggta tggcttcatt cagctccggt tcccaacgat caaggcgagt tacatgatcc    5640
cccatgttgt gcaaaaaagc ggttagctcc ttcggtcctc cgatcgttgt cagaagtaag    5700
ttggccgcag tgttatcact catggttatg gcagcactgc ataattctct tactgtcatg    5760
ccatccgtaa gatgcttttc tgtgactggt gagtactcaa ccaagtcatt ctgagaatag    5820
```

```
tgtatgcggc gaccgagttg ctcttgcccg gcgtcaatac gggataatac cgcgccacat    5880
agcagaactt taaaagtgct catcattgga aaacgttctt cggggcgaaa actctcaagg    5940
atcttaccgc tgttgagatc cagttcgatg taacccactc gtgcacccaa ctgatcttca    6000
gcatctttta ctttcaccag cgtttctggg tgagcaaaaa caggaaggca aaatgccgca    6060
aaaaagggaa taagggcgac acggaaatgt tgaatactca tactcttcct ttttcaatat    6120
tattgaagca tttatcaggg ttattgtctc atgagcggat acatatttga atgtatttag    6180
aaaaataaac aatagggggt tccgcgcaca tttccccgaa aagtgccacc tgacgtc       6237
```

<210> SEQ ID NO 23
<211> LENGTH: 6101
<212> TYPE: DNA
<213> ORGANISM: artificial
<220> FEATURE:
<223> OTHER INFORMATION: vector pCINeo-GCSFb

<400> SEQUENCE: 23

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cggctatggc tggacctgcc acccagagcc ccatgaagct   1140
gatggccctg cagctgctgc tgtggcacag tgcactctgg acagtgcagg aagccacccc   1200
cctgggccct gccagctccc tgccccagag cttcctgctc aagtgcttag agcaagtgag   1260
gaagatccag ggcgatggcg cagcgctcca ggagaagctg tgtgccacct acaagctgtg   1320
ccaccccgag gagctggtgc tgctcggaca ctctctgggc atcccctggg ctcccctgag   1380
cagctgcccc agccaggccc tgcagctggc aggctgcttg agccaactcc atagcggcct   1440
tttcctctac caggggctcc tgcaggccct ggaaggatc tcccccgagt gggtcccac    1500 cttggacaca ctgcagctgg acgtcgccga ctttgccacc accatctggc agcagatgga   1560
agaactggga atggcccctg ccctgcagcc cacccagggt gccatgccgg ccttcgcctc   1620
```

```
tgctttccag cgccgggcag gaggggtcct ggttgcctcc catctgcaga gcttcctgga   1680
ggtgtcgtac cgccgttctac gccaccttgc ccagccctga agccgaattc acgcgtggta   1740
cctctagagt cgacccgggc ggccgcttcc ctttagtgag ggttaatgct tcgagcagac   1800
atgataagat acattgatga gtttggacaa accacaacta gaatgcagtg aaaaaaatgc   1860
tttatttgtg aaatttgtga tgctattgct ttatttgtaa ccattataag ctgcaataaa   1920
caagttaaca acaacaattg cattcatttt atgtttcagg ttcagggggga gatgtgggag   1980 gttttttaaa gcaagtaaaa cctctacaaa tgtggtaaaa tccgataagg atcgatccgg   2040
gctggcgtaa tagcgaagag gcccgcaccg atcgcccttc ccaacagttg cgcagcctga   2100
atggcgaatg gacgcgccct gtagcggcgc attaagcgcg gcgggtgtgg tggttacgcg   2160
cagcgtgacc gctacacttg ccagcgccct agcgcccgct cctttcgctt tcttcccttc   2220
ctttctcgcc acgttcgccg gctttccccg tcaagctcta atcgggggc tccctttagg   2280 gttccgattt agtgctttac ggcacctcga ccccaaaaaa cttgattagg gtgatggttc   2340
acgtagtggg ccatcgccct gatagacggt ttttcgccct tgacgttgg agtccacgtt   2400 ctttaatagt ggactcttgt tccaaactgg aacaacactc aaccctatct cggtctattc   2460
ttttgattta tagggatttt tgccgatttc ggcctattgg ttaaaaaatg agctgattta   2520
acaaaaattt aacgcgaatt ttaacaaaat attaacgctt acaatttcct gatgcggtat   2580
tttctcctta cgcatctgtg cggtatttca caccgcatac gcggatctgc gcagcaccat   2640
ggcctgaaat aacctctgaa agaggaactt ggttaggtac cttctgaggc ggaaagaacc   2700
agctgtggaa tgtgtgtcag ttagggtgtg gaaagtcccc aggctcccca gcaggcagaa   2760
gtatgcaaag catgcatctc aattagtcag caaccaggtg tggaaagtcc ccaggctccc   2820
cagcaggcag aagtatgcaa agcatgcatc tcaattagtc agcaaccata gtcccgcccc   2880
taactccgcc catcccgccc ctaactccgc ccagttccgc ccattctccg ccccatggct   2940
gactaatttt ttttatttat gcagaggccg aggccgcctc ggcctctgag ctattccaga   3000
agtagtgagg aggcttttt ggaggcctag gcttttgcaa aaagcttgat tcttctgaca   3060
caacagtctc gaacttaagg ctagagccac catgattgaa caagatggat tgcacgcagg   3120
ttctccggcc gcttgggtgg agaggctatt cggctatgac tgggcacaac agacaatcgg   3180
ctgctctgat gccgccgtgt tccggctgtc agcgcagggg cgcccggttc ttttttgtcaa   3240 gaccgacctg tccggtgccc tgaatgaact gcaggacgag gcagcgcggc tatcgtggct   3300
ggccacgacg ggcgttcctt gcgcagctgt gctcgacgtt gtcactgaag cgggaaggga   3360
ctggctgcta ttgggcgaag tgccggggca ggatctcctg tcatctcacc ttgctcctgc   3420
cgagaaagta tccatcatgg ctgatgcaat gcggcggctg catacgcttg atccggctac   3480
ctgcccattc gaccaccaag cgaaacatcg catcgagcga gcacgtactc ggatggaagc   3540
cggtcttgtc gatcaggatg atctggacga agagcatcag gggctcgcgc cagccgaact   3600
gttcgccagg ctcaaggcgc gcatgcccga cggcgaggat ctcgtcgtga cccatggcga   3660
tgcctgcttg ccgaatatca tggtggaaaa tggccgcttt tctggattca tcgactgtgg   3720
ccggctgggt gtggcggacc gctatcagga catagcgttg gctacccgtg atattgctga   3780
agagcttggc ggcgaatggg ctgaccgctt cctcgtgctt tacggtatcg ccgctcccga   3840
ttcgcagcgc atcgccttct atcgccttct tgacgagttc ttctgagcgg gactctgggg   3900
ttcgaaatga ccgaccaagc gacgcccaac ctgccatcac gatggccgca ataaaatatc   3960 tttatttca ttacatctgt gtgttggttt tttgtgtgaa tcgatagcga taaggatccg   4020
```

```
cgtatggtgc actctcagta caatctgctc tgatgccgca tagttaagcc agccccgaca    4080
cccgccaaca cccgctgacg cgccctgacg ggcttgtctg ctcccggcat ccgcttacag    4140
acaagctgtg accgtctccg ggagctgcat gtgtcagagg ttttcaccgt catcaccgaa    4200
acgcgcgaga cgaaagggcc tcgtgatacg cctattttta taggttaatg tcatgataat    4260
aatggtttct tagacgtcag gtggcacttt tcggggaaat gtgcgcggaa cccctatttg    4320
tttatttttc taaatacatt caaatatgta tccgctcatg agacaataac cctgataaat    4380
gcttcaataa tattgaaaaa ggaagagtat gagtattcaa catttccgtg tcgcccttat    4440
tcccttttt gcggcatttt gccttcctgt ttttgctcac ccagaaacgc tggtgaaagt    4500
aaaagatgct gaagatcagt tgggtgcacg agtgggttac atcgaactgg atctcaacag    4560
cggtaagatc cttgagagtt ttcgccccga agaacgtttt ccaatgatga gcacttttaa    4620
agttctgcta tgtggcgcgg tattatcccg tattgacgcc gggcaagagc aactcggtcg    4680
ccgcatacac tattctcaga atgacttggt tgagtactca ccagtcacag aaaagcatct    4740
tacggatggc atgacagtaa gagaattatg cagtgctgcc ataaccatga gtgataacac    4800
tgcggccaac ttacttctga caacgatcgg aggaccgaag gagctaaccg cttttttgca    4860
caacatgggg gatcatgtaa ctcgccttga tcgttgggaa ccggagctga atgaagccat    4920
accaaacgac gagcgtgaca ccacgatgcc tgtagcaatg gcaacaacgt tgcgcaaact    4980
attaactggc gaactactta ctctagcttc ccggcaacaa ttaatagact ggatggaggc    5040
ggataaagtt gcaggaccac ttctgcgctc ggcccttccg gctggctggt ttattgctga    5100
taaatctgga gccggtgagc gtgggtctcg cggtatcatt gcagcactgg ggccagatgg    5160
taagccctcc cgtatcgtag ttatctacac gacgggagt caggcaacta tggatgaacg    5220
aaatagacag atcgctgaga taggtgcctc actgattaag cattggtaac tgtcagacca    5280
agtttactca tatatacttt agattgattt aaaacttcat ttttaattta aaaggatcta    5340
ggtgaagatc ctttttgata atctcatgac caaaatccct aacgtgagt tttcgttcca    5400
ctgagcgtca gaccccgtag aaaagatcaa aggatcttct tgagatcctt ttttctgcg    5460
cgtaatctgc tgcttgcaaa caaaaaaacc accgctacca gcggtggttt gtttgccgga    5520
tcaagagcta ccaactcttt ttccgaaggt aactggcttc agcagagcgc agataccaaa    5580
tactgttctt ctagtgtagc cgtagttagg ccaccacttc aagaactctg tagcaccgcc    5640
tacatacctc gctctgctaa tcctgttacc agtggctgct gccagtggcg ataagtcgtg    5700
tcttaccggg ttggactcaa gacgatagtt accggataag gcgcagcggt cgggctgaac    5760
ggggggttcg tgcacacagc ccagcttgga gcgaacgacc tacaccgaac tgagatacct    5820
acagcgtgag ctatgagaaa gcgccacgct tcccgaaggg agaaaggcgg acaggtatcc    5880
ggtaagcggc agggtcggaa caggagagcg cacgagggag cttccagggg gaaacgcctg    5940
gtatctttat agtcctgtcg ggtttcgcca cctctgactt gagcgtcgat ttttgtgatg    6000
ctcgtcaggg gggcggagcc tatggaaaaa cgccagcaac gcggcctttt tacggttcct    6060
ggccttttgc tggccttttg ctcacatggc tcgacagatc t                       6101
```

<210> SEQ ID NO 24
<211> LENGTH: 4920
<212> TYPE: DNA
<213> ORGANISM: artificial
<220> FEATURE:
<223> OTHER INFORMATION: vector pCMVScript_GCSFb

```
<400> SEQUENCE: 24
atgcattagt tattaatagt aatcaattac ggggtcatta gttcatagcc catatatgga      60
gttccgcgtt acataactta cggtaaatgg cccgcctggc tgaccgccca acgaccccg     120 cccattgacg tcaataatga cgtatgttcc catagtaacg ccaatagggra ctttccattg    180 acgtcaatgg gtggagtatt tacggtaaac tgcccacttg gcagtacatc aagtgtatca    240
tatgccaagt acgcccccta ttgacgtcaa tgacggtaaa tggcccgcct ggcattatgc    300
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agatccgcta    600
gcgattacgc caagctcgaa attaaccctc actaaaggga acaaaagctg gagctccacc    660
gcggtggcgg ccgctctagc ccgggcggat ccactagtaa cggccgccag tgtgctggaa    720
ttcggctatg gctggacctg ccacccagag ccccatgaag ctgatggccc tgcagctgct    780
gctgtggcac agtgcactct ggacagtgca ggaagccacc cccctgggcc ctgccagctc    840
cctgccccag agcttcctgc tcaagtgctt agagcaagtg aggaagatcc agggcgatgg    900
cgcagcgctc aggagaaagc tgtgtgccac ctacaagctg tgccaccccg aggagctggt    960
gctgctcgga cactctctgg catcccctg gctcccctg agcagctgcc ccagccaggc   1020
cctgcagctg gcaggctgct tgagccaact ccatagcggc cttttcctct accaggggct   1080
cctgcaggcc ctggaaggga tctcccccga gttgggtccc accttggaca cactgcagct   1140
ggacgtcgcc gactttgcca ccaccatctg gcagcagatg gaaagactgg gaatggcccc   1200
tgccctgcag cccacccagg gtgccatgcc ggccttcgcc tctgctttcc agcgccgggc   1260
aggaggggtc ctggttgcct cccatctgca gagcttcctg gaggtgtcgt accgcgttct   1320
acgccacctt gcccagccct gaagccgaat tctgcagata tccatcacac tggcggccgc   1380 tcgaggggggg gcccggtacc aggtaagtgt acccaattcg ccctatagtg agtcgtatta   1440
caattcactc gatcgcccct cccaacagtt gcgcagcctg aatggcgaat ggagatccaa   1500
tttttaagtg tataatgtgt taaactactg attctaattg tttgtgtatt ttagattcac   1560
agtcccaagg ctcatttcag gcccctcagt cctcacagtc tgttcatgat cataatcagc   1620
cataccacat ttgtagaggt tttacttgct ttaaaaaacc tcccacacct cccctgaac    1680 ctgaaacata aaatgaatgc aattgttgtt gttaacttgt ttattgcagc ttataatggt   1740
tacaaataaa gcaatagcat cacaaatttc acaaataaag cattttttc actgcattct    1800 agttgtggtt tgtccaaact catcaatgta tcttaacgcg taaattgtaa gcgttaatat   1860
tttgttaaaa ttcgcgttaa atttttgtta atcagctca ttttttaacc aataggccga    1920
aatcggcaaa atcccttata atcaaaaga atagaccgag atagggttga gtgttgttcc   1980
agtttggaac aagagtccac tattaaagaa cgtggactcc aacgtcaaag ggcgaaaaac   2040
cgtctatcag ggcgatggcc cactacgtga accatcaccc taatcaagtt ttttggggtc   2100
gaggtgccgt aaagcactaa atcggaaccc taaagggagc cccgatttta gcttgacg    2160 gggaaagccg cgaacgtgg cgagaaagga agggaagaa gcgaaggag cgggcgctag     2220 ggcgctggca agtgtagcgg tcacgctgcg cgtaaccacc acaccgcg cgcttaatgc    2280 gccgctacag ggcgcgtcag gtggcacttt tcggggaaat gtgcgcggaa ccctatttg    2340
```

```
tttattttc  taaatacatt  caaatatgta  tccgctcatg  agacaataac  cctgataaat   2400
gcttcaataa  tattgaaaaa  ggaagaatcc  tgaggcggaa  agaaccagct  gtggaatgtg   2460
tgtcagttag  ggtgtggaaa  gtccccaggc  tccccagcag  gcagaagtat  gcaaagcatg   2520
catctcaatt  agtcagcaac  caggtgtgga  aagtccccag  gctccccagc  aggcagaagt   2580
atgcaaagca  tgcatctcaa  ttagtcagca  accatagtcc  cgcccctaac  tccgcccatc   2640
ccgcccctaa  ctccgcccag  ttccgcccat  tctccgcccc  atggctgact  aattttttt   2700 atttatgcag  aggccgaggc  cgcctcggcc  tctgagctat  tccagaagta  gtgaggaggc   2760
ttttttggag  gcctaggctt  ttgcaaagat  cgatcaagag  acaggatgag  gatcgtttcg   2820
catgattgaa  caagatggat  tgcacgcagg  ttctccggcc  gcttgggtgg  agaggctatt   2880
cggctatgac  tgggcacaac  agacaatcgg  ctgctctgat  gccgccgtgt  tccgctgtc    2940 agcgcagggg  cgcccggttc  tttttgtcaa  gaccgacctg  tccggtgccc  tgaatgaact   3000
gcaagacgag  gcagcgcggc  tatcgtggct  ggccacgacg  ggcgttcctt  gcgcagctgt   3060
gctcgacgtt  gtcactgaag  cgggaaggga  ctggctgcta  ttgggcgaag  tgccggggca   3120
ggatctcctg  tcatctcacc  ttgctcctgc  cgagaaagta  tccatcatgg  ctgatgcaat   3180
gcggcggctg  catacgcttg  atccggctac  ctgcccattc  gaccaccaag  cgaaacatcg   3240
catcgagcga  gcacgtactc  ggatggaagc  cggtcttgtc  gatcaggatg  atctggacga   3300
agaacatcag  gggctcgcgc  cagccgaact  gttcgccagg  ctcaaggcga  gcatgcccga   3360
cggcgaggat  ctcgtcgtga  cccatggcga  tgcctgcttg  ccgaatatca  tggtggaaaa   3420
tggccgcttt  tctggattca  tcgactgtgg  ccggctgggt  gtggcggacc  gctatcagga   3480
catagcgttg  gctacccgtg  atattgctga  agaacttggc  ggcgaatggg  ctgaccgctt   3540
cctcgtgctt  tacggtatcg  ccgctcccga  ttcgcagcgc  atcgccttct  atcgccttct   3600
tgacgagttc  ttctgagcgg  gactctgggg  ttcgaaatga  ccgaccaagc  gacgcccaac   3660
ctgccatcac  gagatttcga  ttccaccgcc  gccttctatg  aaaggttggg  cttcggaatc   3720
gttttccggg  acgccggctg  gatgatcctc  cagcgcgggg  atctcatgct  ggagttcttc   3780
gcccacccta  gggggaggct  aactgaaaca  cggaaggaga  caataccgga  aggaacccgc   3840
gctatgacgg  caataaaaag  acagaataaa  acgcacggtg  ttgggtcgtt  tgttcataaa   3900
cgcggggttc  ggtcccaggg  ctggcactct  gtcgataccc  caccgagacc  ccattgggggc  3960 caatacgccc  gcgtttcttc  cttttcccca  ccccacccccc  caagttcggg  tgaaggccca   4020
gggctcgcag  ccaacgtcgg  ggcggcaggc  cctgccatag  cctcaggtta  ctcatatata   4080
ctttagattg  atttaaaact  tcattttta  tttaaaagga  tctaggtgaa  gatccttttt   4140
gataatctca  tgaccaaaat  cccttaacgt  gagttttcgt  tccactgagc  gtcagacccc   4200
gtagaaaaga  tcaaaggatc  ttcttgagat  ccttttttc  tgcgcgtaat  ctgctgcttg   4260
caaacaaaaa  aaccaccgct  accagcggtg  gtttgtttgc  cggatcaaga  gctaccaact   4320 cttttttccga  aggtaactgg  cttcagcaga  gcgcagatac  caaatactgt  ccttctagtg   4380
tagccgtagt  taggccacca  cttcaagaac  tctgtagcac  cgcctacata  cctcgctctg   4440
ctaatcctgt  taccagtggc  tgctgccagt  ggcgataagt  cgtgtcttac  cgggttggac   4500
tcaagacgat  agttaccgga  taaggcgcag  cggtcgggct  gaacggggggg  ttcgtgcaca   4560 cagcccagct  tggagcgaac  gacctacacc  gaactgagat  acctacagcg  tgagctatga   4620
gaaagcgcca  cgcttcccga  agggagaaag  gcggacaggt  atccggtaag  cggcagggtc   4680
```

```
ggaacaggag agcgcacgag ggagcttcca gggggaaacg cctggtatct ttatagtcct    4740
gtcgggtttc gccacctctg acttgagcgt cgattttttgt gatgctcgtc aggggggcgg    4800
agcctatgga aaacgccag caacgcggcc ttttttacggt tcctggcctt ttgctggcct    4860
tttgctcaca tgttctttcc tgcgttatcc cctgattctg tggataaccg tattaccgcc    4920
```

<210> SEQ ID NO 25
<211> LENGTH: 6917
<212> TYPE: DNA
<213> ORGANISM: artificial
<220> FEATURE:
<223> OTHER INFORMATION: vector pTG2-GCSFb-hyg-as

<400> SEQUENCE: 25

```
cgcgttgaca ttgattattg actagttatt aatagtaatc aattacgggg tcattagttc      60
atagcccata tatggagttc cgcgttacat aacttacggt aaatggcccg cctggctgac     120
cgcccaacga cccccgccca ttgacgtcaa taatgacgta tgttcccata gtaacgccaa     180
tagggacttt ccattgacgt caatgggtgg actatttacg gtaaactgcc cacttggcag     240
tacatcaagt gtatcatatg ccaagtacgc ccctattga cgtcaatgac ggtaaatggc      300
ccgcctggca ttatgcccag tacatgacct tatgggactt tcctacttgg cagtacatct     360
acgtattagt catcgctatt accatggtga tgcggttttg gcagtacatc aatgggcgtg     420
gatagcggtt tgactcacgg ggatttccaa gtctccaccc cattgacgtc aatgggagtt     480
tgttttggca ccaaaatcaa cgggactttc caaaatgtcg taacaactcc gccccattga     540
cgcaaatggg cggtaggcgt gtacggtggg aggtctatat aagcagagct ctctggctaa     600
ctagagaacc cactgcttaa ctggcttatc gaaattaata cgactcacta tagggagacc     660
ggaagcttgg taccgagctc ggatccacta gtaacggccg ccagtgtgct ggaattcggc     720
tatggctgga cctgccaccc agagccccat gaagctgatg gccctgcagc tgctgctgtg     780
gcacagtgca ctctggacag tgcaggaagc accccccctg ggccctgcca gctccctgcc     840
ccagagcttc ctgctcaagt gcttagagca agtgaggaag atccagggcg atggcgcagc     900
gctccaggag aagctgtgtg ccacctacaa gctgtgccac cccgaggagc tggtgctgct     960
cggacactct ctgggcatcc cctgggctcc cctgagcagc tgccccagcc aggccctgca    1020
gctggcaggc tgcttgagcc aactccatag cggccttttc tctaccagg ggctcctgca     1080 ggccctggaa gggatctccc ccgagttggg tcccaccttg gacacactgc agctggacgt    1140
cgccgacttt gccaccacca tctggcagca gatggaagaa ctgggaatgg cccctgccct    1200
gcagcccacc cagggtgcca tgccggcctt cgcctctgct ttccagcgcc gggcaggagg    1260
ggtcctggtt gctcccatc tgcagagctt cctggaggtg tcgtaccgcg ttctacgcca    1320
ccttgcccag ccctgaagcc gaattctgca gatatccatc acactggcgg ccgcgactct    1380
agctagagga tctttgtgaa ggaaccttac ttctgtggtg tgacataatt ggacaaacta    1440
cctacagaga tttaaagctc taaggtaaat ataaaatttt taagtgtata atgtgttaaa    1500
ctactgattc taattgtttg tgtatttag attccaacct atggaactga tgaatgggag    1560
cagtggtgga atgcctttaa tgaggaaaac ctgttttgct cagaagaaat gccatctagt    1620
gatgatgagg ctactgctga ctctcaacat tctactcctc caaaaaagaa gagaaaggta    1680
gaagacccca aggactttcc ttcagaattg ctaagttttt tgagtcatgc tgtgtttagt    1740
aatagaactc ttgcttgctt tgctatttac accacaaagg aaaaagctgc actgctatac    1800
aagaaaatta tggaaaaata ttctgtaacc tttataagta ggcataacag ttataatcat    1860
```

```
aacatactgt tttttcttac tccacacagg catagagtgt ctgctattaa taactatgct    1920
caaaaattgt gtacctttag cttttaatt tgtaaagggg ttaataagga atatttgatg    1980
tatagtgcct tgactagaga tcataatcag ccataccaca tttgtagagg ttttacttgc    2040
tttaaaaaac ctcccacacc tccccctgaa cctgaaacat aaaatgaatg caattgttgt    2100
tgttaacttg tttattgcag cttataatgg ttacaaataa agcaatagca tcacaaattt    2160
cacaaataaa gcatttttt cactgcattc tagttgtggt ttgtccaaac tcatcaatgt    2220
atcttatcat gtctggatcc ccagcttggc actggcgcca gaaatccgcg cggtggtttt    2280
tgggggtcgg gggtgtttgg cagccacaga cgcccggtgt tcgtgtcgcg ccagtacatg    2340
cggtccatgc ccaggccatc caaaaaccat gggtctgtct gctcagtcca gtcgtggacc    2400
tgaccccacg caacgcccaa aagaataacc cccacgaacc ataaaccatt ccccatgggg    2460
gaccccgtcc ctaacccacg gggcccgtgg ctatggcggg cttgccgccc gacgttggc    2520 tgcgagccct gggccttcac ccgaacttgg gggttgggt ggggaaaagg aagaaacgcg    2580
ggcgtattgg ccccaatggg gtctcggtgg ggtatcgaca gagtgccagc cctgggaccg    2640
aaccccgcgt ttatgaacaa acgacccaac acccgtgcgt tttattctgt cttttttatg    2700
ccgtcatagc gcgggttcct tccggtattg tctccttccg tgtttcagtt agcctccccc    2760
atctcccgat ccccacgagt gctggggcgt cggtttccac tatcggcgag tacttctaca    2820
cagccatcgg tccagacggc cgcgcttctg cgggcgattt tgtacgccc gacagtcccg    2880 gctccggatc ggacgattgc gtcgcatcga ccctgcgccc aagctgcatc atcgaaattg    2940
ccgtcaacca agctctgata gagttggtca agaccaatgc ggagcatata cgcccggagc    3000
cgcggcgatc ctgcaagctc cggatgcctc cgctcgaagt agcgcgtctg ctgctccata    3060
caagccaacc acggcctcca gaagaagatg ttggcgacct cgtattggga atccccgaac    3120
atcgcctcgc tccagtcaat gaccgctgtt atgcggccat tgtccgtcag gacattgttg    3180
gagccgaaat ccgcgtgcac gaggtgccgg acttcggggc agtcctcggc ccaaagcatc    3240
agctcatcga gagcctgcgc gacggacgca ctgacggtgt cgtccatcac agtttgccag    3300
tgatacacat ggggatcagc aatcgcgcat atgaaatcac gccatgtagt gtattgaccg    3360
attccttgcg gtccgaatgg gccgaacccg ctcgtctggc taagatcggc cgcagcgatc    3420
gcatccatgg cctccgcgac cggctgcaga acagcgggca gttcggtttc aggcaggtct    3480
tgcaacgtga caccctgtgc acggcgggag atgcaatagg tcaggctctc gctgaattcc    3540
ccaatgtcaa gcacttccgg aatcgggagc gcggccgatg caaagtgccg ataaacataa    3600
cgatctttgt agaaaccatc ggcgcagcta tttacccgca ggacatatcc acgccctcct    3660
acatcgaagc tgaaagcacg agattcttcg ccctccgaga gctgcatcag gtcggagacg    3720
ctgtcgaact tttcgatcag aaacttctcg acagacgtcg cggtgagttc aggcttttc    3780 atatcaagct gatcttgcgg cacgctgttg acgctgttaa gcgggtcgct gcagggtcgc    3840
tcggtgttcg aggccacacg cgtcaccta atatgcgaag tggacctggg accgcgccgc    3900
cccgactgca tctgcgtgtt cgaattcgcc aatgacaaga cgctgggcgg ggtttgtgtc    3960
atcatagaac taaagacatg caaatatatt tcttccgggg acaccgccag caaacgcgag    4020
caacgggcca cggggatgaa gcagcccggc ggcacctcgc taacggattc accactccaa    4080
gaattggagc caatcaattc ttgcggagaa ctgtgaatgc gcaaaccaac ccttggcaga    4140
acatatccat cgcgtccgcc atctccagca gccgcacgcg gcgcatctcg gggccgacgc    4200
```

```
gctgggctac gtcttgctgg cgttcggggt accgctctag agcgaattaa ttcactggcc    4260
gtcgttttac aacgtcgtga ctgggaaaac cctggcgtta cccaacttaa tcgccttgca    4320
gcacatcccc ctttcgccag ctggcgtaat agcgaagagg cccgcaccga tcgcccttcc    4380
caacagttgc gcagcctgaa tggcgaatgg cgcctgatgc ggtattttct ccttacgcat    4440
ctgtgcggta tttcacaccg catatggtgc actctcagta caatctgctc tgatgccgca    4500
tagttaagcc agccccgaca cccgccaaca cccgctgacg cgccctgacg ggcttgtctg    4560
ctcccggcat ccgcttacag acaagctgtg accgtctccg ggagctgcat gtgtcagagg    4620
ttttcaccgt catcaccgaa acgcgcgaga cgaaagggcc tcgtgatacg cctatttttta   4680
taggttaatg tcatgataat aatggtttct tagacgtcag gtggcacttt tcggggaaat    4740
gtgcgcggaa cccctatttg tttatttttc taaatacatt caaatatgta tccgctcatg    4800
agacaataac cctgataaat gcttcaataa tattgaaaaa ggaagagtat gagtattcaa    4860
catttccgtg tcgcccttat ccctttttt gcggcatttt gccttcctgt ttttgctcac    4920
ccagaaacgc tggtgaaagt aaaagatgct gaagatcagt tgggtgcacg agtgggttac    4980
atcgaactgg atctcaacag cggtaagatc cttgagagtt ttcgccccga gaacgttttt   5040
ccaatgatga gcacttttaa agttctgcta tgtggcgcgg tattatcccg tattgacgcc    5100
gggcaagagc aactcggtcg ccgcatacac tattctcaga atgacttggt tgagtactca    5160
ccagtcacag aaaagcatct tacgatggca tgacagtaa gagaattatg cagtgctgcc    5220
ataaccatga gtgataacac tgcggccaac ttacttctga caacgatcgg aggaccgaag    5280
gagctaaccg cttttttgca caacatgggg gatcatgtaa ctcgccttga tcgttgggaa    5340
ccggagctga atgaagccat accaaacgac gagcgtgaca ccacgatgcc tgtagcaatg    5400
gcaacaacgt tgcgcaaact attaactggc gaactactta ctctagcttc ccggcaacaa    5460
ttaatagact ggatggaggc ggataaagtt gcaggaccac ttctgcgctc ggcccttccg    5520
gctggctggt ttattgctga taaatctgga gccggtgagc gtgggtctcg cggtatcatt    5580
gcagcactgg ggccagatgg taagccctcc cgtatcgtag ttatctacac gacggggagt    5640
caggcaacta tggatgaacg aaatagacag atcgctgaga taggtgcctc actgattaag    5700
cattggtaac tgtcagacca agtttactca tatatacttt agattgattt aaaacttcat    5760
ttttaattta aaaggatcta ggtgaagatc ctttttgata atctcatgac caaaatccct    5820
taacgtgagt tttcgttcca ctgagcgtca gaccccgtag aaaagatcaa aggatcttct    5880
tgagatcctt ttttttctgcg cgtaatctgc tgcttgcaaa caaaaaaacc accgctacca    5940
gcggtggttt gtttgccgga tcaagagcta ccaactcttt ttccgaaggt aactggcttc    6000
agcagagcgc agataccaaa tactgtcctt ctagtgtagc cgtagttagg ccaccacttc    6060
aagaactctg tagcaccgcc tacatacctc gctctgctaa tcctgttacc agtggctgct    6120
gccagtggcg ataagtcgtg tcttaccggg ttggactcaa gacgatagtt accggataag    6180
gcgcagcggt cgggctgaac ggggggttcg tgcacacagc ccagcttgga gcgaacgacc    6240
tacaccgaac tgagatacct acagcgtgag ctatgagaaa gcgccacgct tcccgaaggg    6300
agaaaggcgg acaggtatcc ggtaagcggc agggtcggaa caggagagcg cacgagggag    6360
cttccagggg gaaacgcctg gtatctttat agtcctgtcg ggtttcgcca cctctgactt    6420
gagcgtcgat ttttgtgatg ctcgtcaggg gggcggagcc tatggaaaaa cgccagcaac    6480
gcggcctttt tacggttcct ggccttttgc tggccttttg ctcacatgtt ctttcctgcg    6540
ttatccctg attctgtgga taaccgtatt accgcctttg agtgagctga taccgctcgc    6600
```

```
cgcagccgaa cgaccgagcg cagcgagtca gtgagcgagg aagcggaaga gcgcccaata      6660
cgcaaaccgc ctctccccgc gcgttggccg attcattaat gcagctggca cgacaggttt      6720
cccgactgga aagcgggcag tgagcgcaac gcaattaatg tgagttagct cactcattag      6780
gcaccccagg ctttacactt tatgcttccg gctcgtatgt tgtgtggaat tgtgagcgga      6840
taacaatttc acacaggaaa cagctatgac catgattacg ccaagctctc tagagagctt      6900
gcatgcctgc aggtcga                                                     6917

<210> SEQ ID NO 26
<211> LENGTH: 615
<212> TYPE: DNA
<213> ORGANISM: Homo sapiens
<220> FEATURE:
<221> NAME/KEY: CDS
<222> LOCATION: (1)..(612)

<400> SEQUENCE: 26 atg gct gga cct gcc acc cag agc ccc atg aag ctg atg gcc ctg cag        48
Met Ala Gly Pro Ala Thr Gln Ser Pro Met Lys Leu Met Ala Leu Gln
1               5                  10                  15 ctg ctg ctg tgg cac agt gca ctc tgg aca gtg cag gaa gcc acc ccc        96
Leu Leu Leu Trp His Ser Ala Leu Trp Thr Val Gln Glu Ala Thr Pro
            20                  25                  30 ctg ggc cct gcc agc tcc ctg ccc cag agc ttc ctc ctc aag tgc tta       144
Leu Gly Pro Ala Ser Ser Leu Pro Gln Ser Phe Leu Leu Lys Cys Leu
        35                  40                  45 gag caa gtg agg aag atc cag ggc gat ggc gca gcg ctc cag gag aag       192
Glu Gln Val Arg Lys Ile Gln Gly Asp Gly Ala Ala Leu Gln Glu Lys
    50                  55                  60 ctg tgt gcc acc tac aag ctg tgc cac ccc gag gag ctg gtg ctg ctc       240
Leu Cys Ala Thr Tyr Lys Leu Cys His Pro Glu Glu Leu Val Leu Leu
65                  70                  75                  80 gga cac tct ctg ggc atc ccc tgg gct ccc ctg agc agc tgc ccc agc       288
Gly His Ser Leu Gly Ile Pro Trp Ala Pro Leu Ser Ser Cys Pro Ser
                85                  90                  95 cag gcc ctg cag ctg gca ggc tgc ttg agc caa ctc cat agc ggc ctt       336
Gln Ala Leu Gln Leu Ala Gly Cys Leu Ser Gln Leu His Ser Gly Leu
            100                 105                 110 ttc ctc tac cag ggg ctc ctg cag gcc ctg gaa ggg atc tcc ccc gag       384
Phe Leu Tyr Gln Gly Leu Leu Gln Ala Leu Glu Gly Ile Ser Pro Glu
        115                 120                 125 ttg ggt ccc acc ttg gac aca ctg cag ctg gac gtc gcc gac ttt gcc       432
Leu Gly Pro Thr Leu Asp Thr Leu Gln Leu Asp Val Ala Asp Phe Ala
    130                 135                 140 acc acc atc tgg cag cag atg gaa gaa ctg gga atg gcc cct gcc ctg       480
Thr Thr Ile Trp Gln Gln Met Glu Glu Leu Gly Met Ala Pro Ala Leu
145                 150                 155                 160 cag ccc acc cag ggt gcc atg ccg gcc ttc gcc tct gct ttc cag cgc       528
Gln Pro Thr Gln Gly Ala Met Pro Ala Phe Ala Ser Ala Phe Gln Arg
                165                 170                 175 cgg gca gga ggg gtc ctg gtt gcc tcc cat ctg cag agc ttc ctg gag       576
Arg Ala Gly Gly Val Leu Val Ala Ser His Leu Gln Ser Phe Leu Glu
            180                 185                 190 gtg tcg tac cgc gtt cta cgc cac ctt gcc cag ccc tga                   615
Val Ser Tyr Arg Val Leu Arg His Leu Ala Gln Pro
        195                 200

<210> SEQ ID NO 27
<211> LENGTH: 204
```

```
<212> TYPE: PRT
<213> ORGANISM: Homo sapiens

<400> SEQUENCE: 27

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
        130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
            195                 200
```